United States Patent
Berkman et al.

(10) Patent No.: US 11,554,183 B2
(45) Date of Patent: Jan. 17, 2023

(54) 18F-LABELED PSMA-TARGETED PET IMAGING AGENTS

(71) Applicants: Cancer Targeted Technology LLC, Woodinville, WA (US); Washington State University, Pullman, WA (US)

(72) Inventors: Clifford Berkman, Pullman, WA (US); Svetlana A. Stekhova, Lynnwood, WA (US)

(73) Assignees: CANCER TARGETED TECHNOLOGY LLC, Woodinville, WA (US); WASHINGTON STATE UNIVERSITY, Pullman, WA (US)

( * ) Notice: Subject to any disclaimer, the term of this patent is extended or adjusted under 35 U.S.C. 154(b) by 189 days.

(21) Appl. No.: 14/774,371

(22) PCT Filed: Mar. 14, 2014

(86) PCT No.: PCT/US2014/027820
§ 371 (c)(1),
(2) Date: Sep. 10, 2015

(87) PCT Pub. No.: WO2014/143736
PCT Pub. Date: Sep. 18, 2014

(65) Prior Publication Data
US 2016/0030605 A1    Feb. 4, 2016

Related U.S. Application Data

(60) Provisional application No. 61/798,108, filed on Mar. 15, 2013.

(51) Int. Cl.
*A61K 51/00* (2006.01)
*A61M 36/14* (2006.01)
(Continued)

(52) U.S. Cl.
CPC ...... *A61K 51/0489* (2013.01); *A61K 51/0402* (2013.01); *C07F 9/2404* (2013.01);
(Continued)

(58) Field of Classification Search
CPC . A61K 51/0489; C07F 9/2404; C07F 9/2416; C07F 9/2458
(Continued)

(56) References Cited

U.S. PATENT DOCUMENTS 7,696,185 B2 *   4/2010  Berkman ............... C07F 9/091
                                                            514/114
8,293,725 B2 *  10/2012  Berkman ............... C07F 9/091
                                                            514/100
(Continued)

FOREIGN PATENT DOCUMENTS

WO   WO-2008028688 A2 *  3/2008  ......... A61K 51/0491
WO   WO 2012/064914        5/2012
(Continued)

OTHER PUBLICATIONS

Lapri et al. J Nucl. Med. 2009, 50, 2042-2048.*
(Continued)

*Primary Examiner* — Michael G. Hartley
*Assistant Examiner* — Sean R Donohue
(74) *Attorney, Agent, or Firm* — McDonnell Boehnen Hulbert & Berghoff LLP

(57) ABSTRACT

Compounds of Marlush formula (I) described in the claims are useful in diagnostic methods for detecting and/or identifying cells presenting PSMA. Disclosed are also methods for preparing the compounds. Representative compounds according to the application are:

(Continued)

-continued

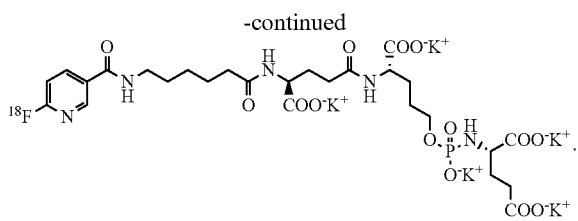

18 Claims, 15 Drawing Sheets

(51) Int. Cl.
*A61K 51/04* (2006.01)
*C07F 9/24* (2006.01)
*C07F 9/58* (2006.01)

(52) U.S. Cl.
CPC .......... *C07F 9/2416* (2013.01); *C07F 9/2458* (2013.01); *C07F 9/58* (2013.01)

(58) Field of Classification Search
USPC ........................................................ 424/1.89
See application file for complete search history.

(56) References Cited

U.S. PATENT DOCUMENTS

| | | | | |
|---|---|---|---|---|
| 9,328,129 | B2* | 5/2016 | Berkman | C07F 9/2408 |
| 9,446,157 | B2* | 9/2016 | Berkman | A61K 51/0497 |
| 9,974,869 | B2* | 5/2018 | Berkman | A61K 51/0497 |
| 10,166,301 | B2* | 1/2019 | Berkman | A61K 51/0497 |
| 2007/0219165 | A1* | 9/2007 | Berkman | C07F 9/091 |
| | | | | 514/114 |
| 2011/0142760 | A1* | 6/2011 | Pomper | A61K 9/127 |
| | | | | 424/1.89 |

FOREIGN PATENT DOCUMENTS

| | | |
|---|---|---|
| WO | WO 2012/174136 | 12/2012 |
| WO | WO 2013/173583 | 11/2013 |
| WO | WO 2013/173630 | 11/2013 |

OTHER PUBLICATIONS

Banerjee et al. J. Med. Chem. 2008, 51, 4504-4517.*
Lasne et al. Top. Curr. Chem. 2002, 201-258.*
Liu et al. Bioorg. Med. Chem. Lett. 21 (2011) 7012-7016.*
Regino, C.A., et al., "Preclinical evaluation of a monoclonal antibody (3C6) specific for prostate-specific membrane antigen" Curr Radiopharm, 2009. 2(1): pp. 9-17.
Zhang, A.X., et al., "A remote arene-binding site on prostate specific membrane antigen revealed by antibody-recruiting small molecules" J. Am. Chem. Soc., 2010, 132(36), 12711-12716.

* cited by examiner

CTT1055

CTT1057

A)

B)

18F-LABELED PSMA-TARGETED PET IMAGING AGENTS

CROSS-REFERENCE TO RELATED APPLICATIONS

This application is a US national phase application of International Patent Application No. PCT/US2014/027820 filed on 14 Mar. 2014, which claims the benefit of the filing date of U.S. Provisional Application Ser. No. 61/798,108 filed 15 Mar. 2013, which is hereby incorporated by reference in its entirety.

STATEMENT AS TO FEDERALLY SPONSORED RESEARCH

This invention was made with government support under R01CA140617 awarded by National Institutes of Health and with government support under R44CA192451 awarded by National Institutes of Health. The government has certain rights in the invention.

BACKGROUND OF THE INVENTION

1. Field of the Invention

The present invention relates to small molecules having high affinity and specificity to prostrate-specific membrane antigen (PSMA), methods for making the molecules, and their use for diagnostic purposes.

2. Summary of the Related Art

Prostate-specific membrane antigen (PSMA) is uniquely overexpressed on the surface of prostate cancer cells as well as in the neovasculature of a variety of solid tumors. As a result, PSMA has attracted attention as a clinical biomarker for detection and management of prostate cancer. Generally, these approaches utilize an antibody specifically targeted at PSMA to direct imaging or therapeutic agents. For example, ProstaScint (Cytogen, Philadelphia, Pa.), which has been approved by the FDA for the detection and imaging of prostate cancer, utilizes an antibody to deliver a chelated radioisotope (Indium-111). However, it is now recognized that the ProstaScint technology is limited to the detection of dead cells and therefore its clinical relevance is questionable.

The success of cancer diagnosis and therapy using antibodies is limited by challenges such as immunogenicity and poor vascular permeability. In addition, large antibodies bound to cell-surface targets present a barrier for subsequent binding of additional antibodies at neighboring cell-surface sites resulting in a decreased cell-surface labeling.

In addition to serving as a cell-surface target for antibodies delivering diagnostic or therapeutic agents, a largely overlooked and unique property of PSMA is its enzymatic activity. That is, PSMA is capable of recognizing and processing molecules as small as dipeptides. Despite the existence of this property, it has been largely unexplored in terms of the development of novel diagnostic and therapeutic strategies. There are a few recent examples in the literature that have described results in detecting prostate cancer cells using labeled small-molecule inhibitors of PSMA.

Certain phosphoramidate PSMA inhibitors have been described in U.S. Pat. Nos. RE42,275 and 8,293,725. And one $^{18}$F-labeled PMSA inhibitor is disclosed in Lapi, S. E., et al., *J. Nucl. Med.* 2009, 50(12), 2042. Other PSMA inhibitors, including radionuclide-chelated analogs, are disclosed in WO 2012/174136.

SUMMARY OF THE INVENTION

Provided herein are diagnostic compounds and methods for detecting PSMA presenting cells, such as prostate cancer cells, that capitalize on the potency and specific affinity of small-molecule inhibitors. The diagnostic agents can be used to monitor and stratify patients for treatment with appropriate therapeutic agents.

In one aspect, the invention comprises compounds that are in the form of formula (I),

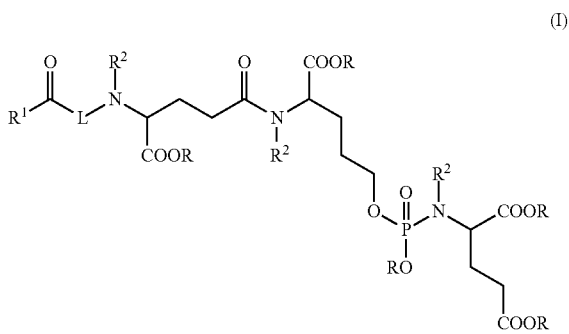

(I)

or a pharmaceutically acceptable salt thereof, wherein

L is a linker comprising a moiety such as one of the formula —NH—CH$_2$CH$_2$—(OCH$_2$CH$_2$—)$_y$—C(O)— or a group of the formula

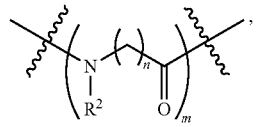

,

R$^1$ is an $^{18}$F-labeled phenyl or pyridyl, and the remaining moieties are defined herein below.

In other aspects, the invention comprises compounds and methods for making compounds of formula (I) and methods of using compounds of formula (I) for detection and imaging of PSMA presenting cells and tissues comprising them.

The foregoing merely summarizes certain aspects of the present invention and is not intended to be limiting. A more expansive and complete description of the various aspects and embodiments of the present invention is provided below. All patents, patent applications, and publications are hereby incorporated by reference in their entirety with the caveat that the present disclosure shall supersede or take precedence over that of prior patents, patent applications, and publications incorporated herein by reference in the event of any conflict or inconsistency.

DETAILED DESCRIPTION OF THE INVENTION

Figure 1:
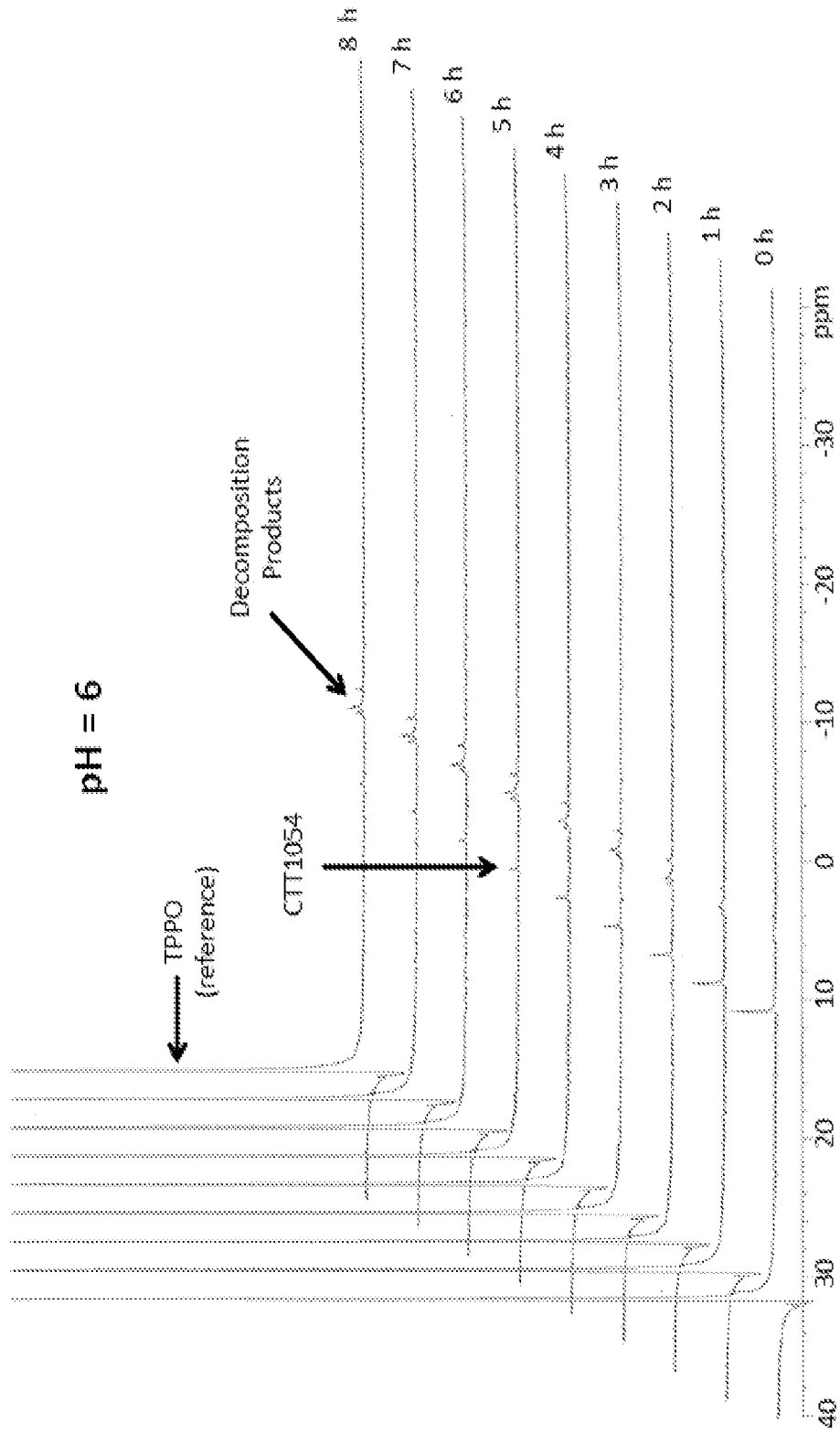
FIG. 1 shows $^{31}$P NMR spectra of a pH 6 solution of CTT1054 at hourly time intervals from 0-8 h.
Figure 2:
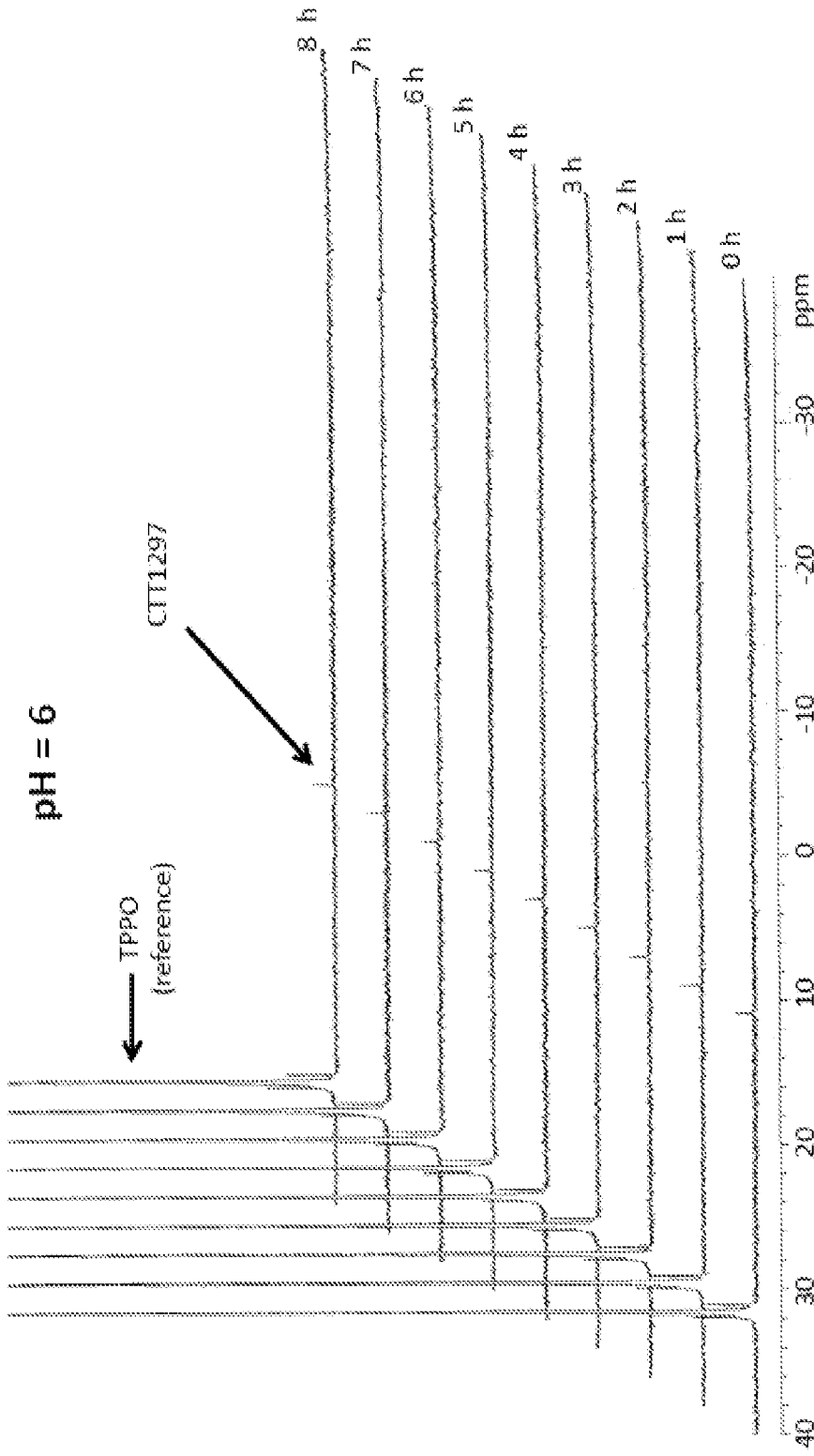
FIG. 2 shows $^{31}$P NMR spectra of a pH 6 solution of CTT1297 at hourly time intervals from 0-8 h.
Figure 3:
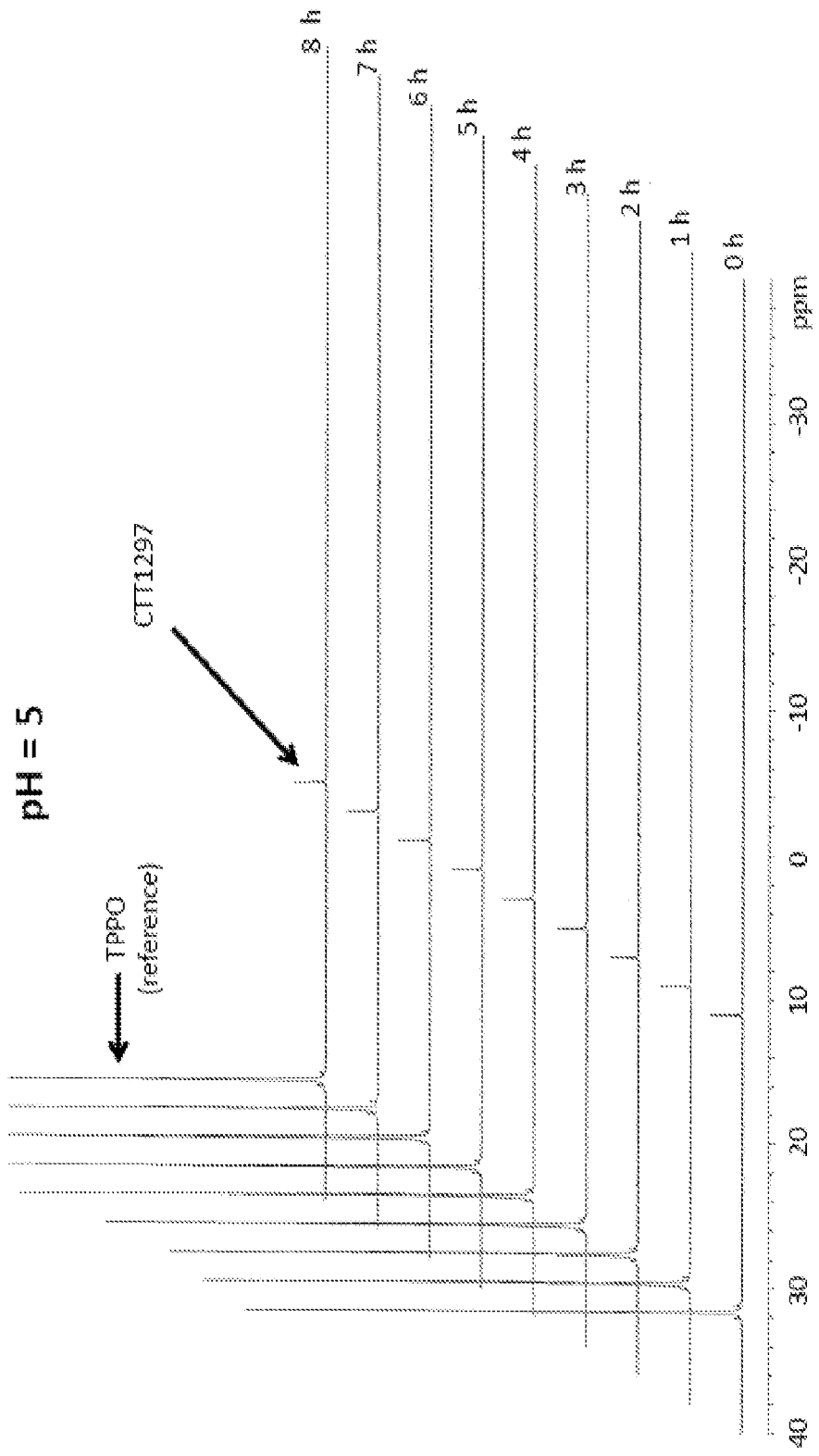
FIG. 3 shows $^{31}$P NMR spectra of a pH 5 solution of CTT1297 at hourly time intervals from 0-8 h.
Figure 4:
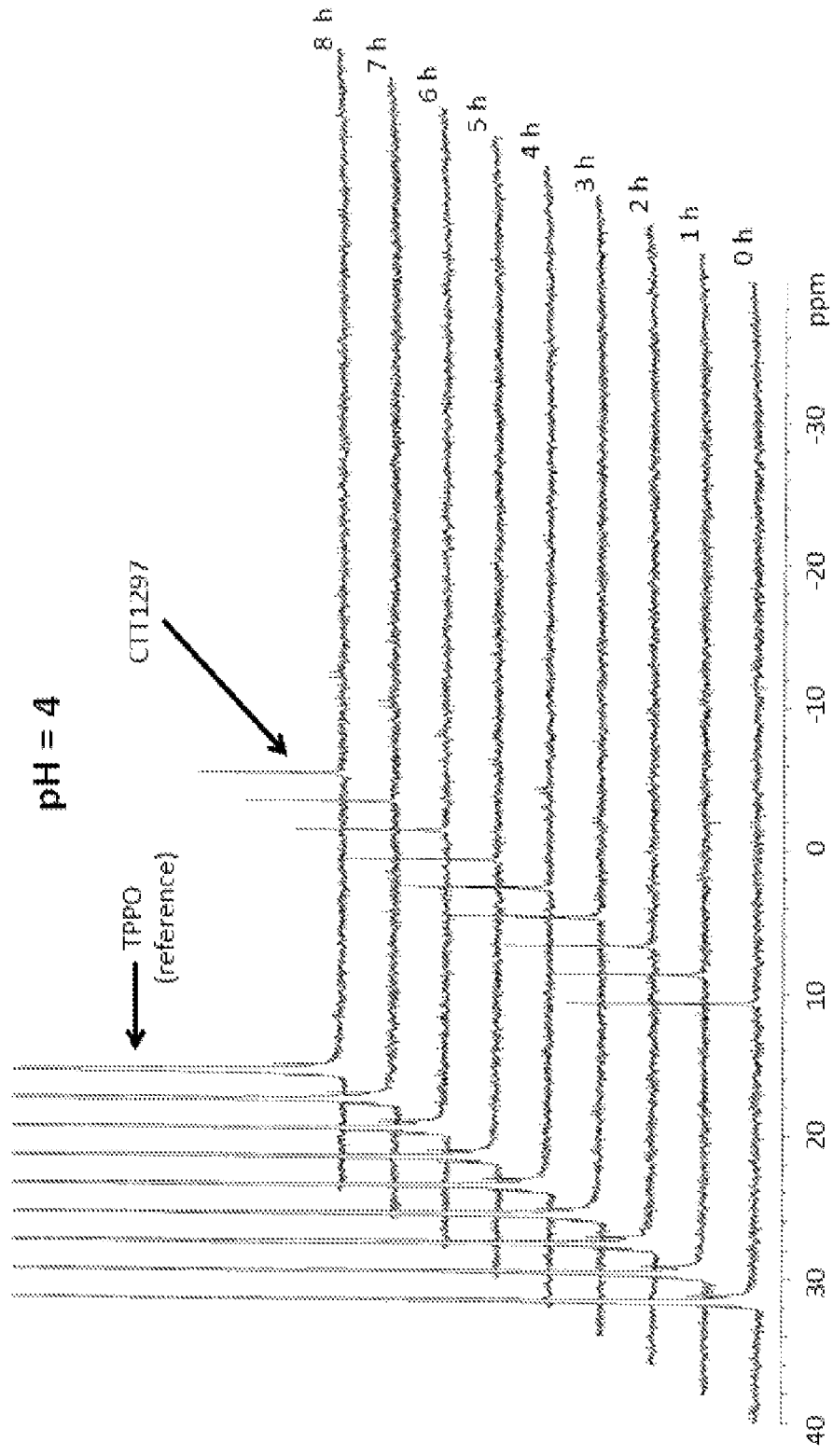
FIG. 4 shows $^{31}$P NMR spectra of a pH 4 solution of CTT1297 at hourly time intervals from 0-8 h.
Figure 5:
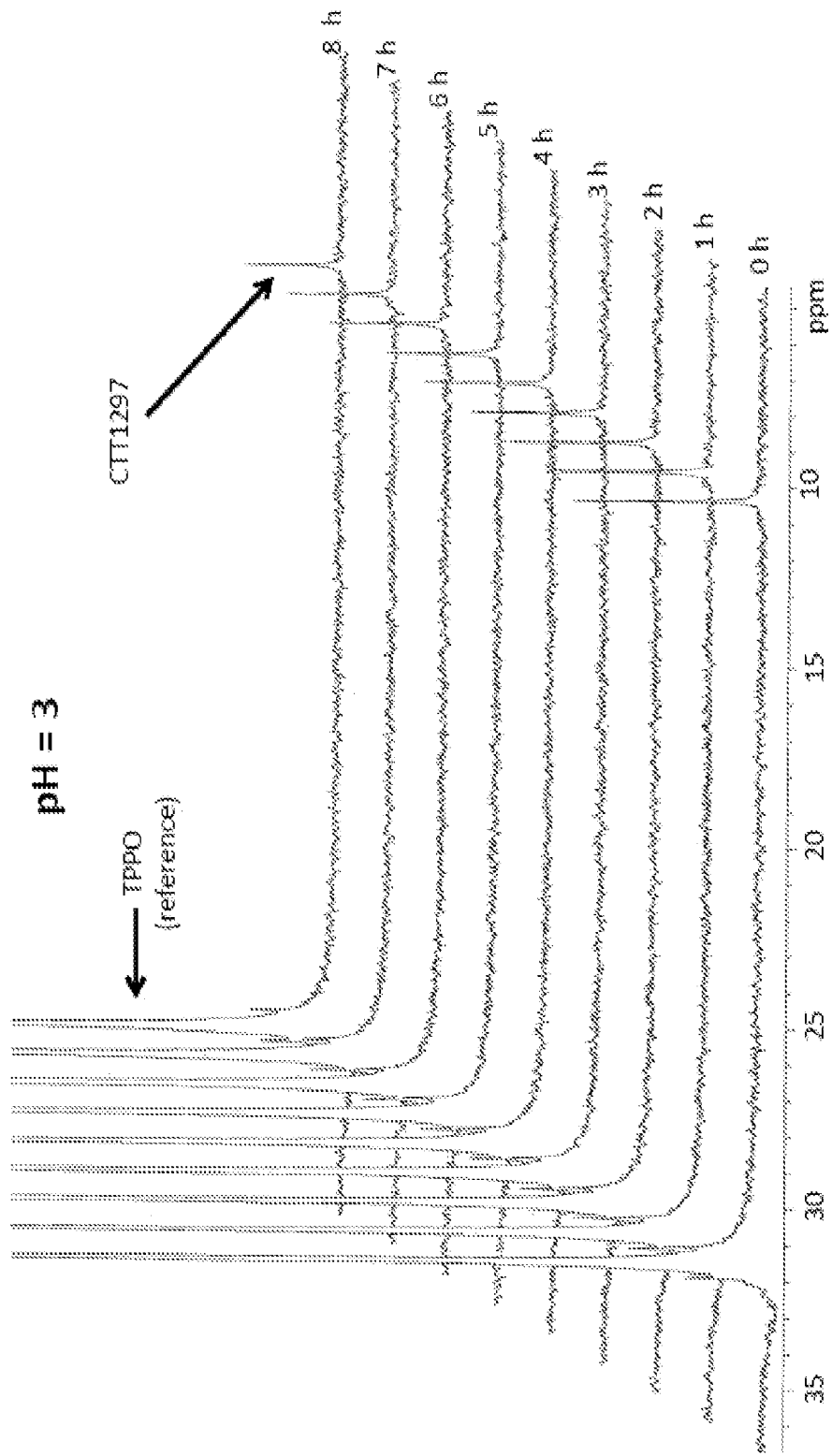
FIG. 5 shows $^{31}$P NMR spectra of a pH 3 solution of CTT1297 at hourly time intervals from 0-8 h.
Figure 6:
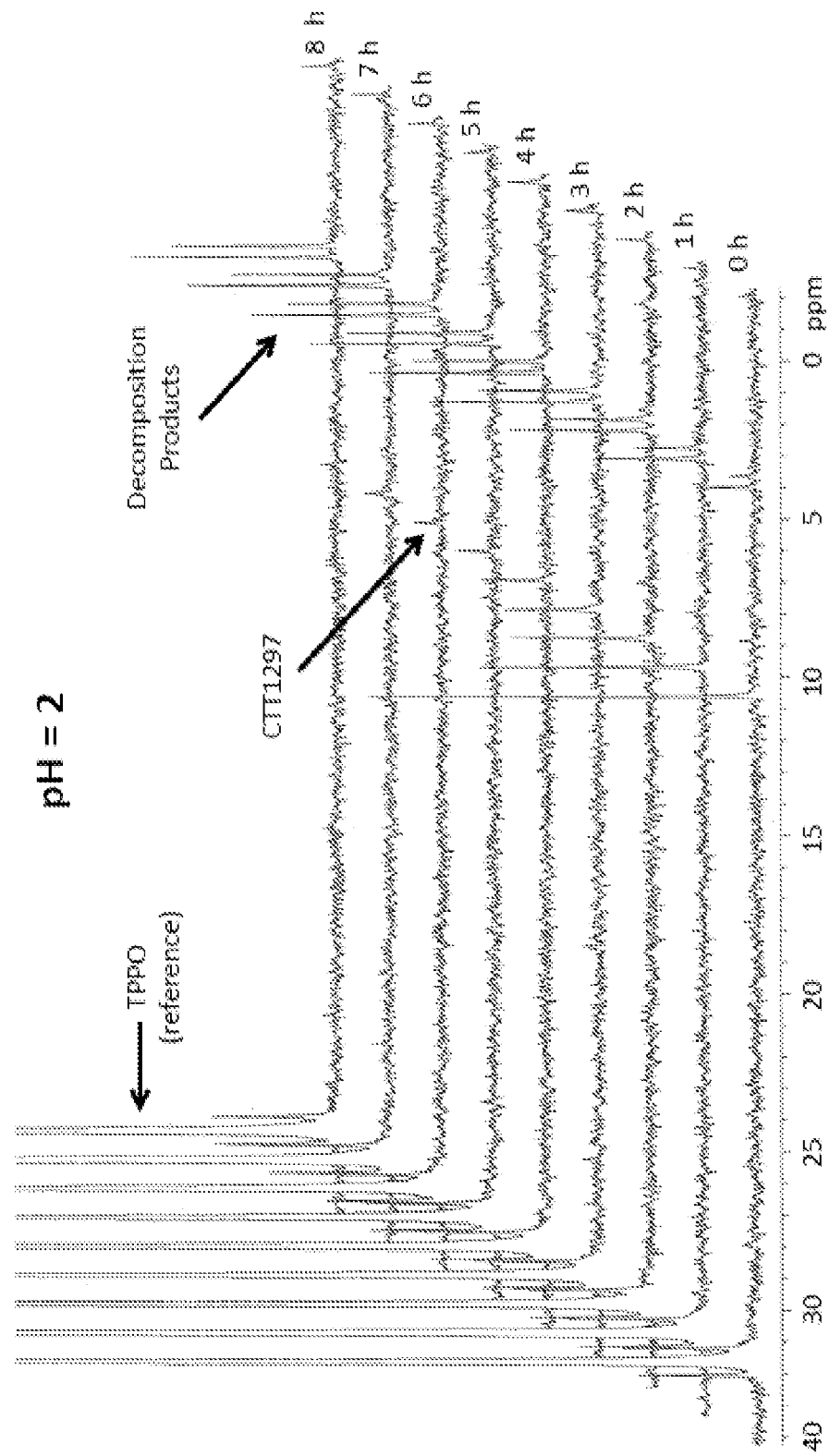
FIG. 6 shows $^{31}$P NMR spectra of a pH 2 solution of CTT1297 at hourly time intervals from 0-8 h.
Figure 7:
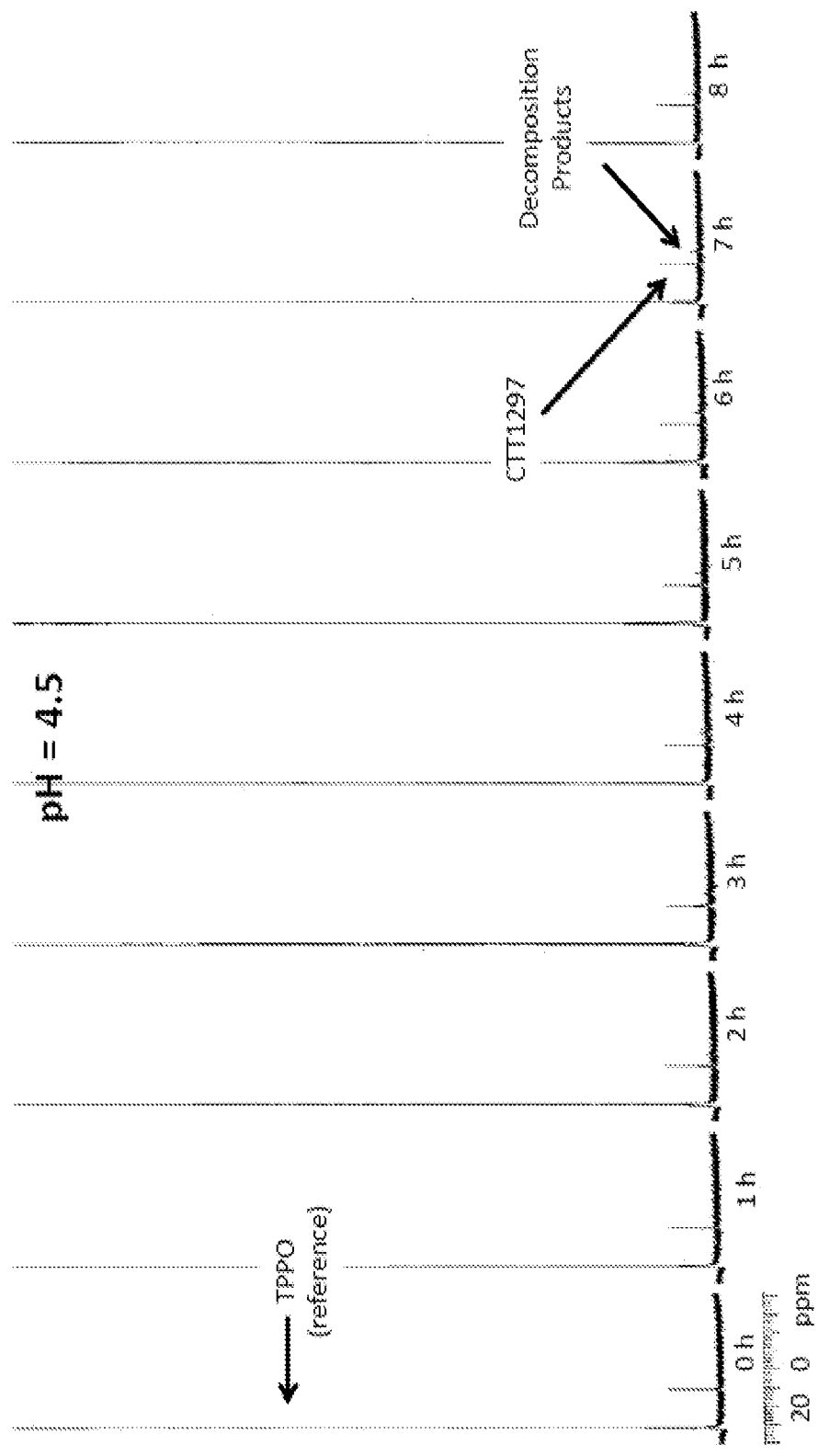
FIG. 7 shows $^{31}$P NMR spectra of a pH 4.5 solution of CTT1000 at hourly time intervals from 0-8 h.

In one aspect, the invention comprises compounds that are in the form of formula (I),

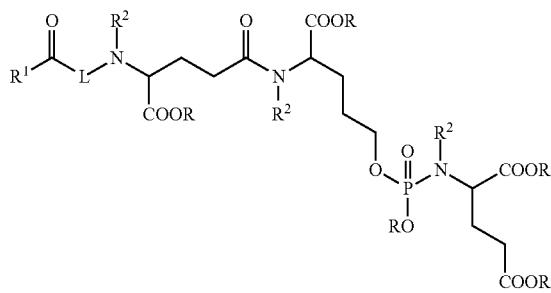

and pharmaceutically acceptable salts thereof, wherein
L is a linker comprising a moiety of the formula —NH—CH$_2$CH$_2$—(OCH$_2$CH$_2$—)$_y$—C(O)— or a group of the formula

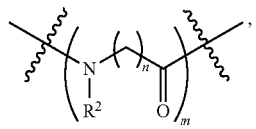

wherein
y is 1, 2, 3, 4, 5, 6, 7, 8, 9, 10, 11 or 12;
m is 1, 2, 3, or 4;
each n is independently 1, 2, 3, 4, 5, 6, 7, 8, 9, 10, 11 or 12;
R$^1$ is phenyl or pyridyl; wherein the phenyl or pyridyl is substituted with an [F]- or [$^{18}$F]-fluoro group and optionally substituted with a second group selected from halogen, cyano, and nitro;
each R$^2$ is independently hydrogen or C$_1$-C$_6$ alkyl; and
each R is independently hydrogen or a protecting group;
provided that when L is a group of the formula

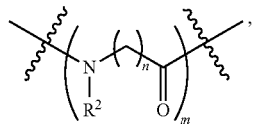

the combination of m and n result in a linear linker length of 3 to 21 atoms. For example, when m is 2 and each n is 4, the linker is twelve atoms in length. If m is 1 and n is 10, the linker length is also 12. Linker length is calculated using the formula m·(n+2). So, 3≤m·(n+2)≤21.

In certain embodiments of the compound of formula (I), the compound is of the formula (Ia):

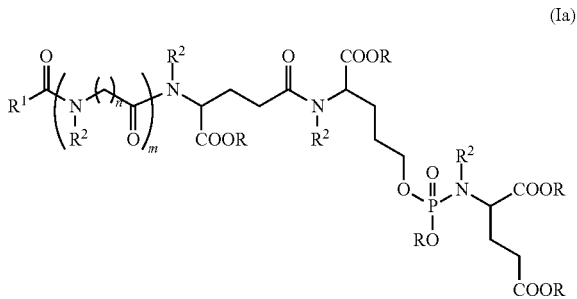

and pharmaceutically acceptable salts thereof, wherein
m, n, R$^1$, R$^2$, and R are as defined for formula (I).

In some embodiments, m is 1, 2, 3 or 4. In other embodiments, m is 1, 2 or 3. Preferably, m is 1 or 2.

In some embodiments, each n is independently 1, 2, 3, 4, 5, 6 or 7. In other embodiments, each n is independently 3, 4, 5 or 6. In some embodiments, each n is 5.

In some embodiments, m is 1 or 2, and each n is 5.

In some embodiments, m is 2, 3 or 4, and two, three or four different options for n can be chosen, provided that the linear length of the resulting linker is greater than or equal to 4, and less than or equal to 20. For example, when m is 2, n is 3 and 5, producing a linker of the structure:

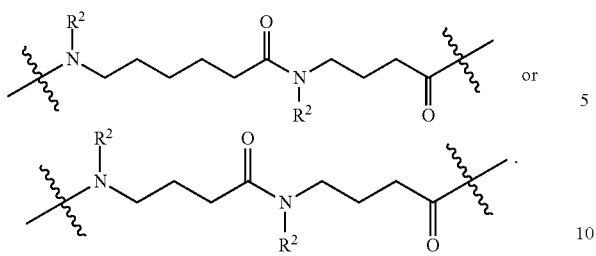

A "protecting group" as used herein is group introduced to a functional group (e.g., an phosphorous acid or carboxylic acid) that allows for chemoselectivity in a subsequent chemical transformation. Such groups, specifically carboxylic and phosphorus acid protecting groups, are described in Greene's Protective Groups in Organic Synthesis, 4th Edition (the relevant parts of which are incorporated by reference).

In some embodiments, a "protecting group" is alkyl, alkenyl, or haloalkyl. This includes, but is not limited to, methyl, ethyl, propyl, isopropyl, tert-butyl, allyl, trifluoromethyl or trifluoroethyl.

In some embodiments, a "protecting group" is benzyl or substituted benzyl, which includes, but is not limited to, triphenylmethyl (trityl), diphenylmethyl, o-nitrobenzyl, 2,4,6-trimethylbenzyl, p-bromobenzyl, p-nitrobenzyl, p-methoxybenzyl (PMB), 2,6-dimethoxybenzyl, 4-(methylsulfinyl)benzyl, 4-sulfobenzyl, 4-azidomethoxybenzyl, and piperonyl.

In certain embodiments of the compound of formula (I), the compound is of the formula (Ib):

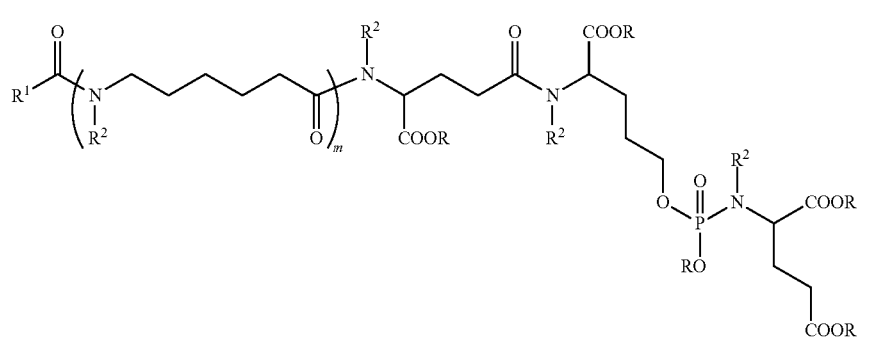

and pharmaceutically acceptable salts thereof.

In some embodiments of the compounds of formula (Ia), m is 1, and each R and $R^2$ is hydrogen. In other embodiments, m is 2, and each R and $R^2$ is hydrogen.

In certain embodiments of the compounds of formulae (I), (Ia) and Ib, $R^1$ is selected from one of the following groups (1a)-(1kk):

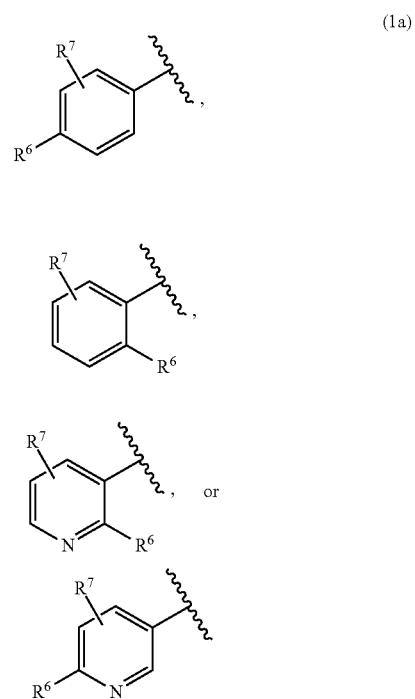

wherein $R^6$ is —F or —$^{18}$F; and $R^7$ is hydrogen, halogen, cyano, or nitro.

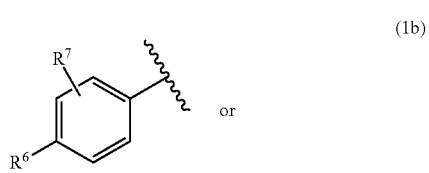

-continued

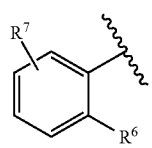

wherein $R^6$ is —F or —$^{18}$F; and $R^7$ is hydrogen, halogen, cyano, or nitro.

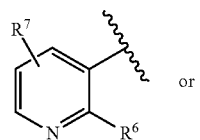
(1c)

or

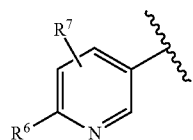

wherein R$^6$ is —F or —$^{18}$F; and R$^7$ is hydrogen, halogen, cyano, or nitro.

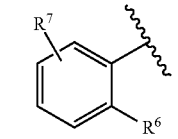
(1d)

wherein R$^6$ is —F or —$^{18}$F; and R$^7$ is hydrogen, halogen, cyano, or nitro.

(1e)

wherein R$^6$ is —F or —$^{18}$F; and R$^7$ is hydrogen, halogen, cyano, or nitro.

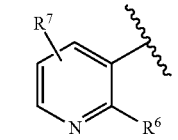
(1f)

wherein R$^6$ is —F or —$^{18}$F; and R$^7$ is hydrogen, halogen, cyano, or nitro.

(1g)

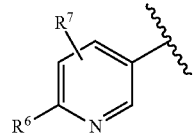

wherein R$^6$ is —F or —$^{18}$F; and R$^7$ is hydrogen, halogen, cyano, or nitro.

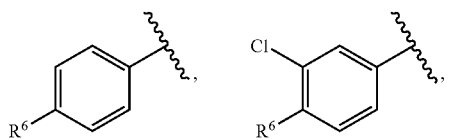
(1h)

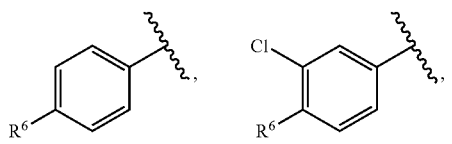

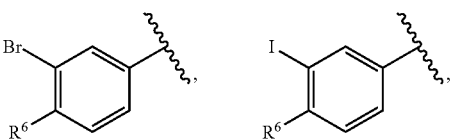

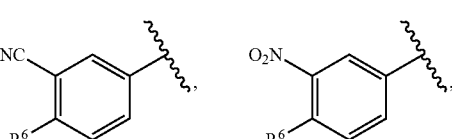

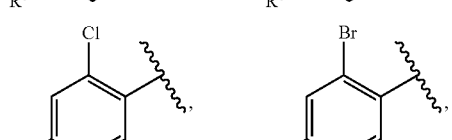

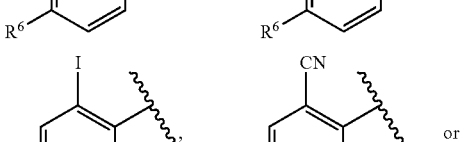

or

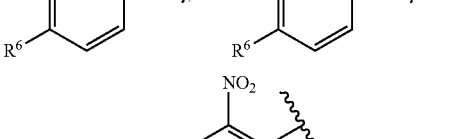

wherein R$^6$ is —F or —$^{18}$F.

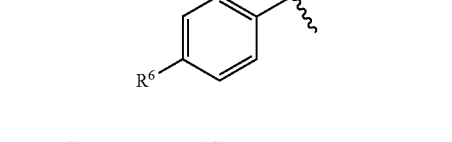
(1i)

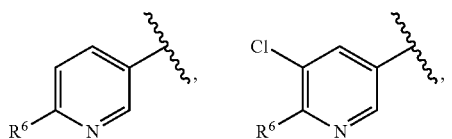

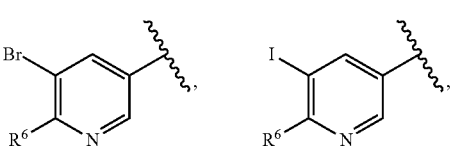

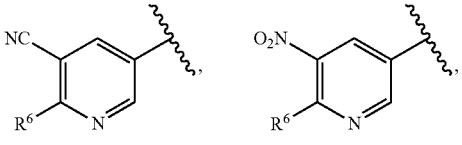

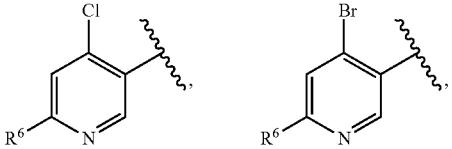

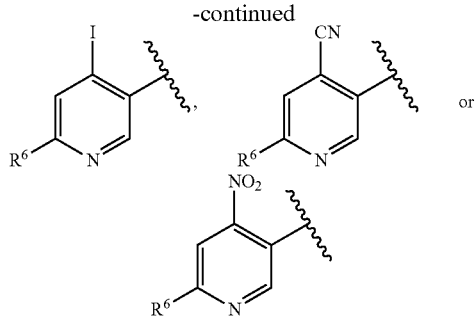
wherein R[6] is —F or —[18]F.
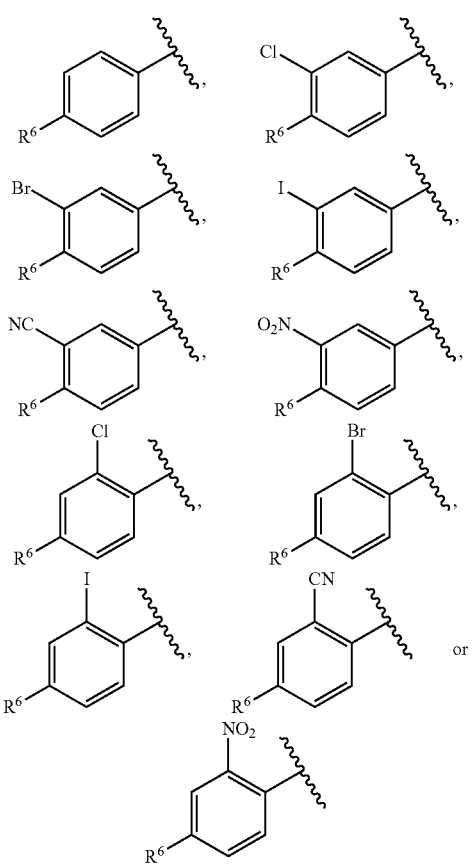
wherein R[6] is —F.
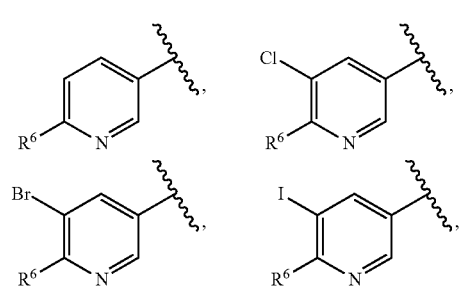
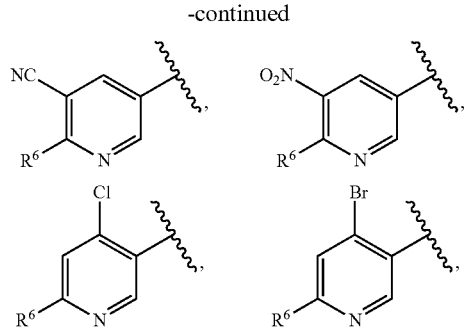
wherein R[6] is —F.
(1l)
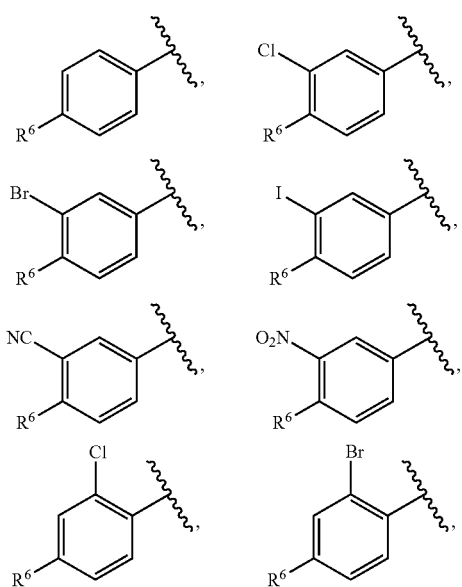
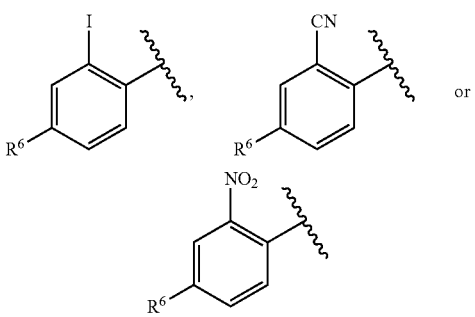
wherein R[6] is —[18]F.

(1m)
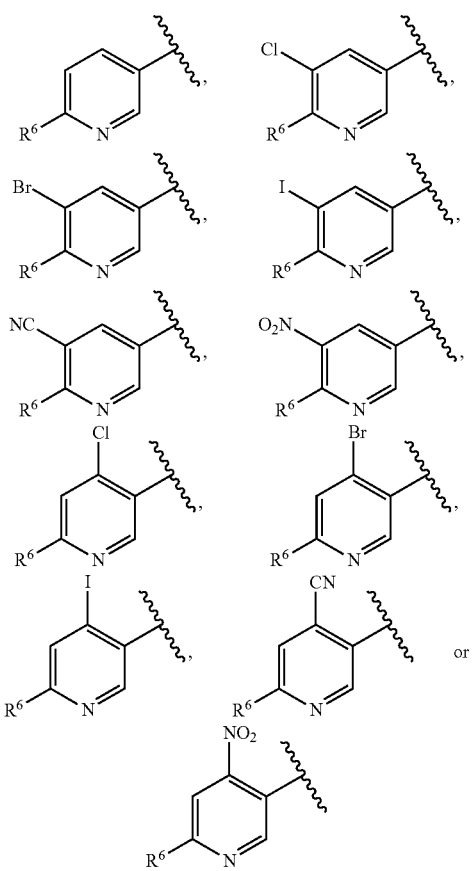
wherein R⁶ is —¹⁸F.
(1n)
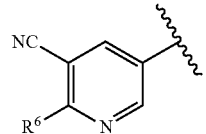
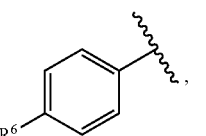
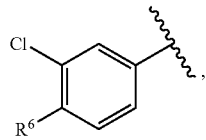
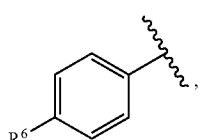
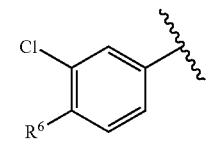
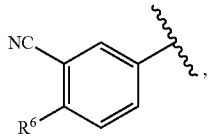
wherein R⁶ is —F or —¹⁸F.
(1o)
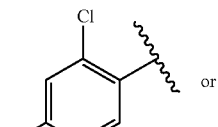
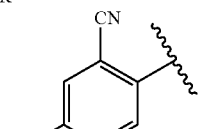
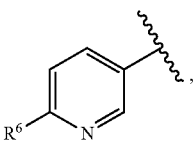
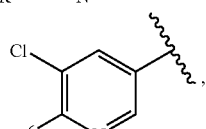
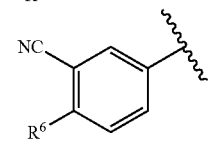
or
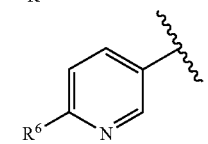
wherein R⁶ is —F or —¹⁸F.
(1p)
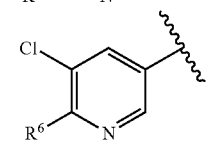
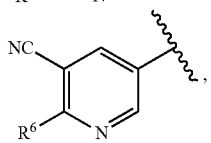
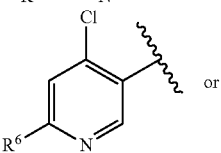
or -continued
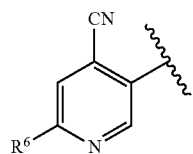
wherein R⁶ is —F or —¹⁸F.
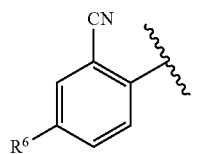
wherein R⁶ is —¹⁸F.
(1q)
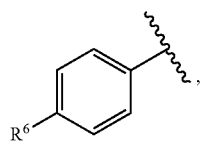
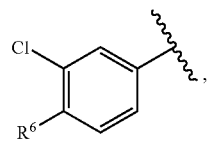
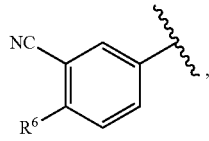
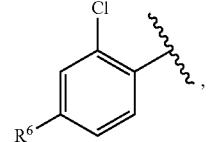
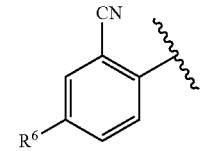
wherein R⁶ is —F.
(1s)
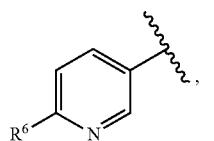
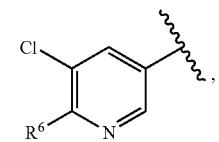
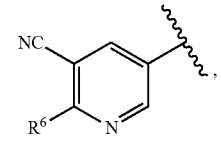
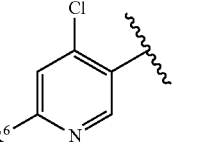
or
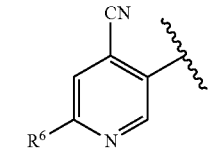
wherein R⁶ is —F.
(1r)
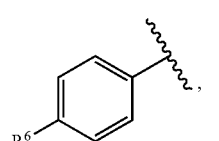
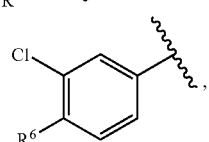
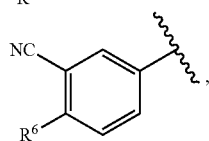
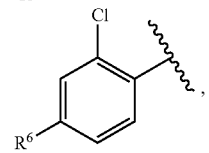
(1t)
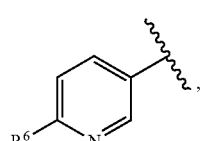
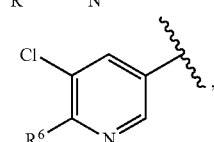
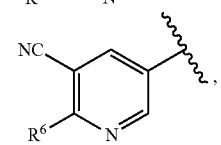
or

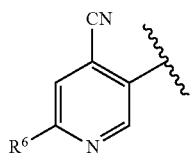
wherein R⁶ is —¹⁸F.
(1u)
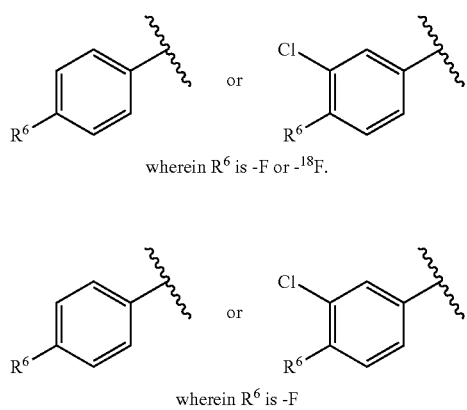
wherein R⁶ is -F or -¹⁸F.
(1v)
wherein R⁶ is -F
(1w)
wherein R⁶ is -¹⁸F
(1x)
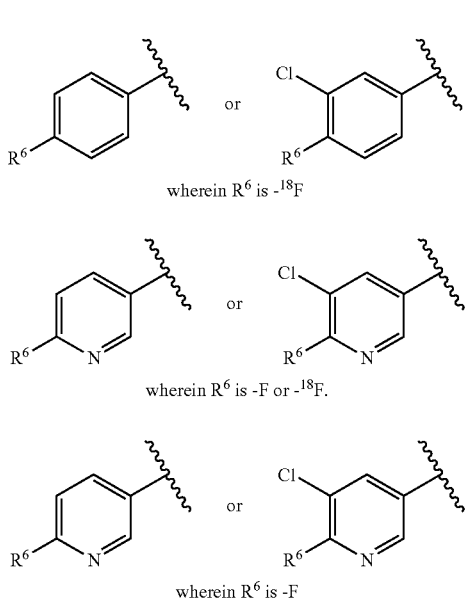
wherein R⁶ is -F or -¹⁸F.
(1y)
wherein R⁶ is -F
(1z)
wherein R⁶ is -¹⁸F
(1aa)
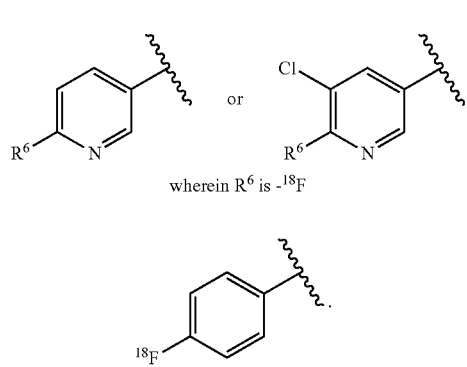
(1bb)
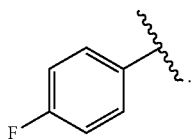
(1cc)
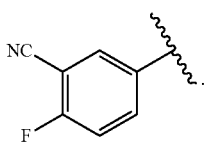
(1dd)
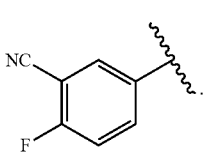
(1ee)
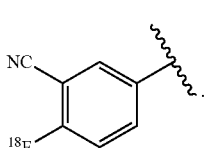
(1ff)
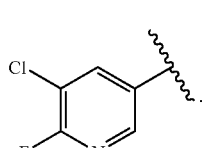
(1gg)
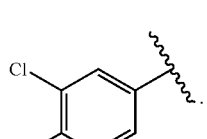
(1hh)
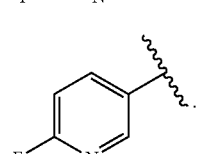
(1ii)
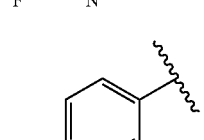
(1jj)
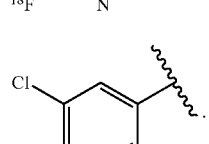
(1kk)
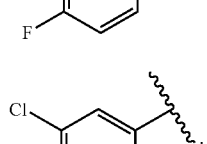
In certain embodiments of the compounds of formulae (I), (Ia) and (Ib), m is selected from one of the following groups (2a)-(2o):

| | | | | | |
|---|---|---|---|---|---|
| (2a) 1, 2, 3 or 4. | (2b) 1, 2 or 3. | (2c) 1 or 2. | (2d) 1. | (2e) 2, 3 or 4. | |
| (2f) 1 or 3. | (2g) 2 or 4. | (2h) 1 or 2. | (2i) 2 or 3. | (2j) 3 or 4. | |
| (2k) 1 or 4. | (2l) 1. | (2m) 2. | (2n) 3. | (2o) 4. | |

In certain embodiments of the compounds of formulae (I), (Ia) and (Ib), each n is independently selected from one of the following groups (3a)-(3x):

| | |
|---|---|
| (3a) 1, 2, 3, 4, 5, 6, 7, 8, 9, 10, 11 or 12. | (3b) 1, 2, 3, 4, 5, 6, 7, 8, 9 or 10. |
| (3c) 1, 2, 3, 4, 5, 6, 7 or 8. | (3d) 1, 2, 3, 4, 5 or 6. |
| (3e) 1, 2, 3 or 4. | (3f) 1 or 2. |
| (3g) 6, 7, 8, 9, 10, 11 or 12. | (3h) 6, 7, 8, 9 or 10. |
| (3i) 3, 4, 5, 6, 7 or 8. | (3j) 2, 4, 6, 8, 10 or 12. |
| (3k) 2, 4, 6 or 8. | (3l) 1, 3, 5, 7, 9 or 11. |
| (3m) 1. | (3n) 2. |
| (3o) 3. | (3p) 4. |
| (3q) 5. | (3r) 6. |
| (3s) 7. | (3t) 8. |
| (3u) 9. | (3v) 10. |
| (3w) 11. | (3x) 12. |

In certain embodiments of the compounds of formulae (I), (Ia) and (Ib), each $R^2$ is independently selected from one of the following groups (4a)-(4v):
 (4a) hydrogen or $C_1$-$C_6$ alkyl.
 (4b) hydrogen or methyl, ethyl, n-propyl, iso-propyl, n-butyl, sec-butyl, iso-butyl, tert-butyl, n-pentyl, iso-pentyl, neopentyl or n-hexyl.
 (4c) hydrogen.
 (4d) $C_1$-$C_6$ alkyl.
 (4e) methyl, ethyl, n-propyl, n-butyl, n-pentyl or n-hexyl.
 (4f) iso-propyl, sec-butyl, iso-butyl, tert-butyl, isopentyl or neopentyl.
 (4g) methyl, ethyl or n-propyl.
 (4h) n-propyl, iso-propyl, n-butyl, sec-butyl, iso-butyl or tert-butyl.
 (4i) methyl, ethyl or n-propyl.
 (4j) methyl or ethyl.
 (4k) methyl.
 (4l) ethyl.
 (4m) n-propyl.
 (4n) iso-propyl.
 (4o) n-butyl.
 (4p) sec-butyl.
 (4q) iso-butyl.
 (4r) tert-butyl.
 (4s) n-pentyl.
 (4t) isopentyl.
 (4u) neopentyl.
 (4v) n-hexyl.

In certain embodiments of the compounds of formulae (I), (Ia) and (Ib), each R is independently selected from one of the following groups (5a)-(5w):
 (5a) hydrogen or a protecting group.
 (5b) hydrogen.
 (5c) a protecting group.
 (5d) alkyl, alkenyl, haloalkyl, benzyl or substituted benzyl.
 (5e) alkyl, alkenyl or haloalkyl.
 (5f) benzyl or substituted benzyl.
 (5g) methyl, ethyl, propyl, isopropyl, tert-butyl, allyl, trifluoromethyl or trifluoroethyl.
 (5h) triphenylmethyl (trityl), diphenylmethyl, o-nitrobenzyl, 2,4,6-trimethylbenzyl, p-bromobenzyl, p-nitrobenzyl, p-methoxybenzyl (PMB), 2,6-dimethoxybenzyl, 4-(methylsulfinyl)benzyl, 4-sulfobenzyl, 4-azidomethoxybenzyl or piperonyl.
 (5i) methyl, ethyl, propyl, isopropyl, tert-butyl or benzyl.
 (5j) o-nitrobenzyl, 2,4,6-trimethylbenzyl, p-bromobenzyl, p-nitrobenzyl, p-methoxybenzyl (PMB) or 2,6-dimethoxybenzyl.
 (5k) methyl.
 (5l) ethyl.
 (5m) propyl.
 (5n) isopropyl.
 (5o) o-nitrobenzyl.
 (5p) 2,4,6-trimethylbenzyl.
 (5q) p-bromobenzyl.
 (5r) p-nitrobenzyl.
 (5s) p-methoxybenzyl (PMB).
 (5t) 2,6-dimethoxybenzyl.
 (5u) tert-butyl or benzyl.
 (5v) tert-butyl.
 (5w) benzyl.

Genera of compounds according to this aspect of the invention also include those in which $R^1$ is any one of (1a)-(1kk), m is any one of (2a)-(2o), each n is independently any one of (3a)-(3x), each $R^2$ is independently any of (4a)-(4v), and each R is independently any one of (5a)-(5w). Representative but non-exclusive examples are described in the following paragraph.

Particular embodiments according to this aspect of the invention include compounds of Formula (I) as defined in each of the following rows, in which each entry is a group number as defined above (e.g., (4k) indicates that $R^2$ is methyl), and a dash "-" indicates that the variable is as defined for formula (I) or is defined according to any applicable variable definition above (e.g., when a cell in the $R^1$ column is "-", $R^1$ can be defined as for Formula (I) or any one of definitions (1a)-(1kk)).

| Form. | | | L | | |
|---|---|---|---|---|---|
| (I) | $R^1$ | m | n | $R^2$ | R |
| I | 1a | 2a | 3a | 4a | 5a |
| I | 1d | 2b | 3g | 4c | 5b |
| I | 1g | 2d | 3m | 4k | 5c |
| I | 1h | 2f | 3n | 4l | 5v |
| I | 1l | 2h | 3q | 4m | 5w |
| I | 1m | 2m | 3l | 4o | 5a |
| I | 1aa | 2l | 3c | 4a | 5b |
| I | 1bb | 2c | 3a | 4c | 5c |
| I | 1cc | 2n | 3g | 4k | 5v |
| I | 1dd | 2a | 3m | 4l | 5w |
| I | 1ee | 2b | 3n | 4m | 5a |
| I | 1ff | 2d | 3q | 4o | 5b |
| I | 1gg | 2f | 3l | 4a | 5c |
| I | 1hh | 2h | 3c | 4c | 5v |
| I | 1ii | 2m | 3q | 4k | 5w |
| I | 1jj | 2l | 3l | 4l | 5a |
| I | 1kk | 2c | 3c | 4m | 5b |
| I | 1a | 2a | 3n | 4o | 5c |
| I | 1d | 2b | 3q | 4a | 5v |
| I | 1g | 2d | 3l | 4c | 5w |
| I | 1h | 2f | 3c | 4k | 5a |
| I | 1l | 2h | 3a | 4l | 5b |
| I | 1m | 2m | 3g | 4m | 5c |
| I | 1aa | 2l | 3m | 4o | 5b |
| I | 1bb | 2a | 3n | 4a | 5c |
| I | 1cc | 2b | 3q | 4c | 5v |
| I | 1dd | 2d | 3g | 4k | 5w |
| I | 1ee | 2f | 3m | 4l | 5a |
| I | 1ff | 2h | 3n | 4m | 5b |
| I | 1gg | 2m | 3q | 4o | 5c |
| I | 1hh | 2b | 3l | 4a | 5v |
| I | 1ii | 2d | 3c | 4c | 5w |

-continued

| Form. (I) | R¹ | L m | L n | R² | R |
|---|---|---|---|---|---|
| I | 1jj | 2f | 3q | 4k | 5a |
| I | 1kk | 2h | 3l | 4l | 5a |
| I | 1l | 2m | 3n | 4m | 5b |
| I | 1m | 2l | 3q | 4o | 5c |
| I | 1aa | 2c | 3l | 4a | 5v |
| I | 1bb | 2n | 3c | 4c | 5w |
| I | 1cc | 2a | 3a | 4k | 5a |
| I | 1dd | 2b | 3g | 4l | 5b |
| I | 1ee | 2d | 3m | 4m | 5c |
| I | 1ff | 2f | 3m | 4o | 5w |
| I | 1gg | 2h | 3n | 4a | 5a |
| I | 1hh | 2d | 3q | 4c | 5b |
| I | 1ii | 2f | 3g | 4k | 5c |
| Ia | 1a | 2a | 3a | 4a | 5a |
| Ia | 1d | 2b | 3g | 4c | 5b |
| Ia | 1g | 2d | 3m | 4k | 5c |
| Ia | 1h | 2f | 3n | 4l | 5v |
| Ia | 1l | 2h | 3q | 4m | 5w |
| Ia | 1m | 2m | 3l | 4o | 5a |
| Ia | 1aa | 2l | 3c | 4a | 5b |
| Ia | 1bb | 2c | 3a | 4c | 5c |
| Ia | 1cc | 2n | 3g | 4k | 5v |
| Ia | 1dd | 2a | 3m | 4l | 5w |
| Ia | 1ee | 2b | 3n | 4m | 5a |
| Ia | 1ff | 2d | 3q | 4o | 5b |
| Ia | 1gg | 2f | 3l | 4a | 5c |
| Ia | 1hh | 2h | 3c | 4c | 5v |
| Ia | 1ii | 2m | 3q | 4k | 5w |
| Ia | 1jj | 2l | 3l | 4l | 5a |
| Ia | 1kk | 2c | 3c | 4m | 5b |
| Ia | 1a | 2a | 3n | 4o | 5c |
| Ia | 1d | 2b | 3q | 4a | 5v |
| Ia | 1g | 2d | 3l | 4c | 5w |
| Ia | 1h | 2f | 3c | 4k | 5a |
| Ia | 1l | 2h | 3a | 4l | 5b |
| Ia | 1m | 2m | 3g | 4m | 5c |
| Ia | 1aa | 2l | 3m | 4o | 5b |
| Ia | 1bb | 2a | 3n | 4a | 5c |
| Ia | 1cc | 2b | 3q | 4c | 5v |
| Ia | 1dd | 2d | 3g | 4k | 5w |
| Ia | 1ee | 2f | 3m | 4l | 5a |
| Ia | 1ff | 2h | 3n | 4m | 5b |
| Ia | 1gg | 2m | 3q | 4o | 5c |
| Ia | 1hh | 2b | 3l | 4a | 5v |
| Ia | 1ii | 2d | 3c | 4c | 5w |
| Ia | 1jj | 2f | 3q | 4k | 5a |
| Ia | 1kk | 2h | 3l | 4l | 5a |
| Ia | 1l | 2m | 3n | 4m | 5b |
| Ia | 1m | 2l | 3q | 4o | 5c |
| Ia | 1aa | 2c | 3l | 4a | 5v |
| Ia | 1bb | 2n | 3c | 4c | 5w |
| Ia | 1cc | 2a | 3a | 4k | 5a |
| Ia | 1dd | 2b | 3g | 4l | 5b |
| Ia | 1ee | 2d | 3m | 4m | 5c |
| Ia | 1ff | 2f | 3m | 4o | 5w |
| Ia | 1gg | 2h | 3n | 4a | 5a |
| Ia | 1hh | 2d | 3q | 4c | 5b |
| Ia | 1ii | 2f | 3g | 4k | 5c |
| Ib | 1a | 2l | — | 4a | 5v |
| Ib | 1d | 2m | — | 4b | 5a |
| Ib | 1g | 2h | — | 4c | 5b |
| Ib | 1h | 2l | — | 4a | 5w |
| Ib | 1l | 2m | — | 4b | 5c |
| Ib | 1m | 2h | — | 4c | 5v |
| Ib | 1aa | 2l | — | 4a | 5a |
| Ib | 1bb | 2m | — | 4b | 5b |
| Ib | 1cc | 2h | — | 4c | 5w |
| Ib | 1dd | 2l | — | 4a | 5v |
| Ib | 1ee | 2m | — | 4b | 5a |
| Ib | 1ff | 2h | — | 4c | 5b |
| Ib | 1gg | 2l | — | 4b | 5v |
| Ib | 1hh | 2m | — | 4c | 5a |
| Ib | 1ii | 2h | — | 4a | 5b |
| Ib | 1jj | 2l | — | 4c | 5b |
| Ib | 1kk | 2m | — | 4c | 5b |
| Ib | 1d | 2h | — | 4c | 5v |
| Ib | 1g | 2l | — | 4a | 5a |
| Ib | 1h | 2m | — | 4b | 5b |
| Ib | 1l | 2h | — | 4c | 5w |
| Ib | 1m | 2l | — | 4b | 5c |
| Ib | 1aa | 2m | — | 4c | 5v |
| Ib | 1bb | 2l | — | 4c | 5b |
| Ib | 1cc | 2l | — | 4b | 5b |
| Ib | 1dd | 2m | — | 4c | 5w |
| Ib | 1ee | 2h | — | 4a | 5v |
| Ib | 1ff | 2l | — | 4b | 5a |
| Ib | 1gg | 2m | — | 4c | 5b |
| Ib | 1hh | 2l | — | 4c | 5b |
| Ib | 1ii | 2l | — | 4a | 5b |
| Ib | 1l | 2m | — | 4b | 5v |
| Ib | 1m | 2h | — | 4c | 5a |
| Ib | 1aa | 2l | — | 4c | 5b |
| Ib | 1bb | 2m | — | 4c | 5b |
| Ib | 1d | 2h | — | 4a | 5c |
| Ib | 1g | 2l | — | 4b | 5v |
| Ib | 1h | 2m | — | 4c | 5a |
| Ib | 1l | 2h | — | 4a | 5b |
| Ib | 1m | 2l | — | 4b | 5w |
| Ib | 1aa | 2m | — | 4c | 5b |
| Ib | 1bb | 2h | — | 4b | 5a |
| Ib | 1cc | 2l | — | 4c | 5b |
| Ib | 1dd | 2m | — | 4a | 5b |
| Ib | 1ee | 2h | — | 4b | 5v |
| Ib | 1ff | 2l | — | 4c | 5a |
| Ib | 1gg | 2m | — | 4c | 5b |
| Ib | 1hh | 2h | — | 4a | 5w |
| Ib | 1ii | 2l | — | 4b | 5c |
| Ib | 1jj | 2m | — | 4c | 5b |
| Ib | 1kk | 2h | — | 4a | 5a |
| Ib | 1d | 2l | — | 4b | 5b |

Compounds of structural formulae (I), (Ia) and (Ib) have three chiral centers. Accordingly, in another aspect of the invention, the invention comprises compounds of formula (I), (Ia) and (Ib) of the formula (I*), (Ia*) or (Ib*), respectively:

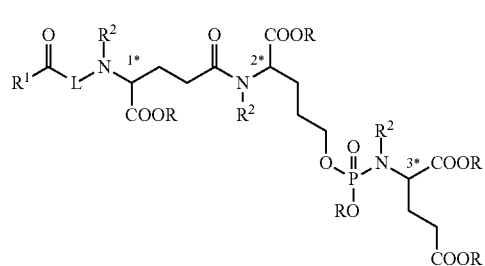 (I*)

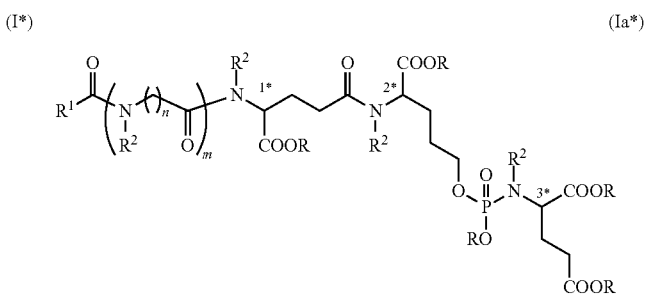 (Ia*)

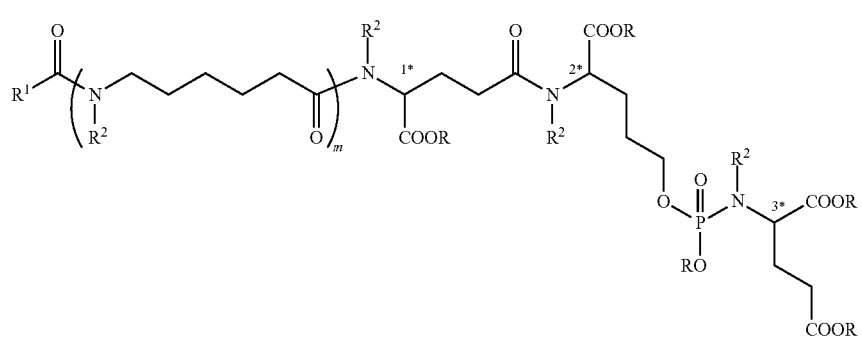 (Ib*)

and pharmaceutically acceptable salts thereof, wherein $R^1$, m, n, $R^2$ and R are defined according to any one of the embodiments described above for formulae (I), (Ia) and (Ib), and one, two, or three of the chiral centers 1*, 2*, and 3* is not racemic. That is, for example, compounds according to this aspect have structural formula (I*), (Ia*) or (Ib*) wherein $R^1$ is any one of (1a)-(1kk), m is any one of (2a)-(2u), each n is independently any one of (3a)-(3x), each $R^2$ is independently any of (4a)-(4v), and each R is independently any one of (5a)-(5w) and one, two, or three of 1*, 2*, and 3* are enantiomerically enriched (defined herein as having >50% R or S stereochemistry) or enantiomerically pure (defined herein as having greater than 90, 91, 92, 93, 94, 95, 96, 97, 98, or 99% R or S stereochemistry).

In structures (I*), (Ia*) and (Ib*), 1*, 2*, and 3* are chiral centers that are independently in the S or R stereoconfiguration. Thus, compounds according to this aspect include those with the following combinations of stereoconfigurations, and mixtures thereof:

| 1* | 2* | 3* |
|----|----|----|
| S  | S  | S  |
| S  | S  | R  |

| 1* | 2* | 3* |
|----|----|----|
| S  | R  | S  |
| R  | S  | S  |

| 1* | 2* | 3* |
|----|----|----|
| S  | R  | R  |
| R  | S  | R  |

-continued

| 1* | 2* | 3* |
|----|----|----|
| R  | R  | S  |
| R  | R  | R  |

In an embodiment of any one of the preceding embodiments of the compounds of formula (I*), the compound is of the formula (Ic):

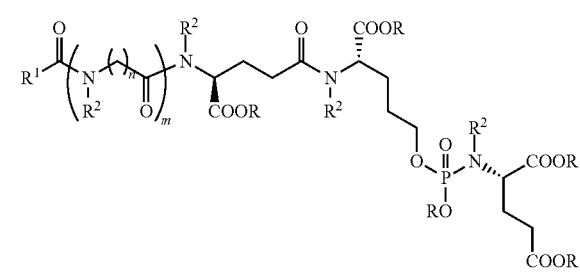 (Ic)

and pharmaceutically acceptable salts thereof.

In an embodiment of any of the preceding embodiments of the compounds of formula (Ia*), the compound is of the formula (Id):

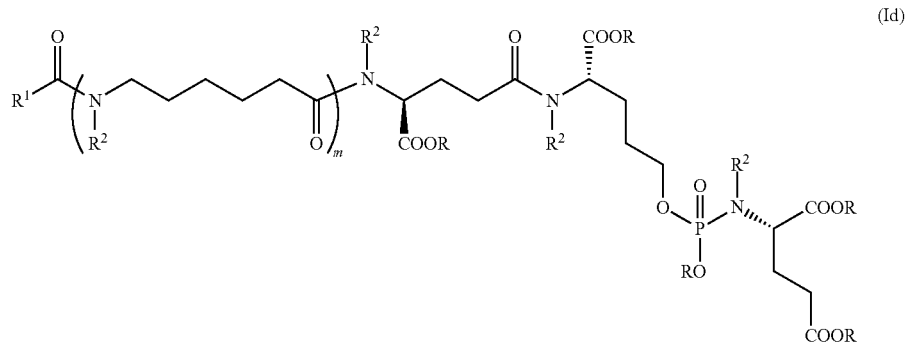
(Id)
and pharmaceutically acceptable salts thereof.
In another embodiment, the compound of formula (I) is
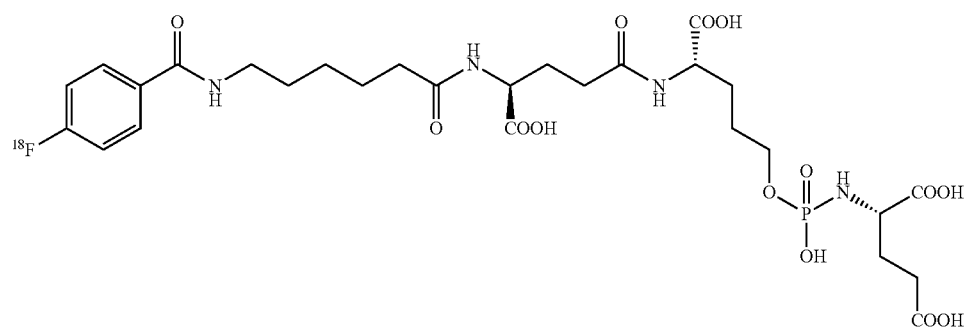
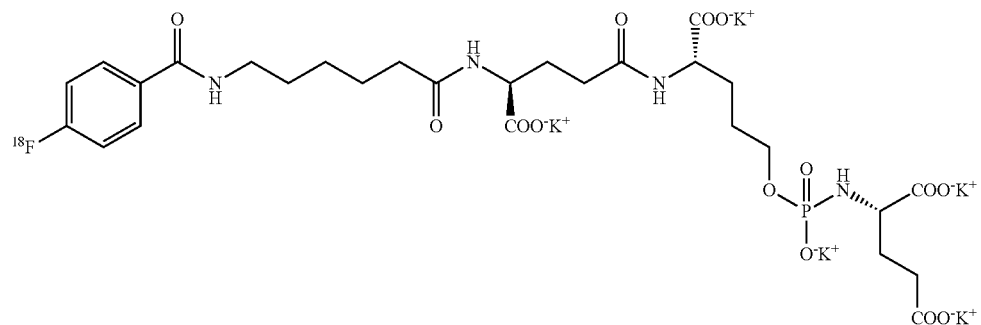
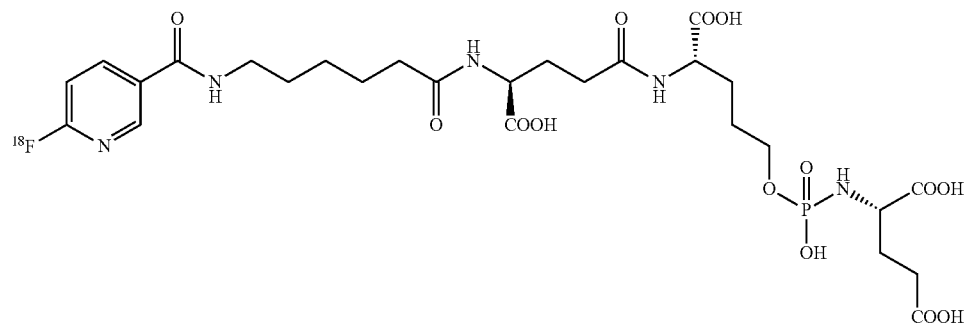

-continued
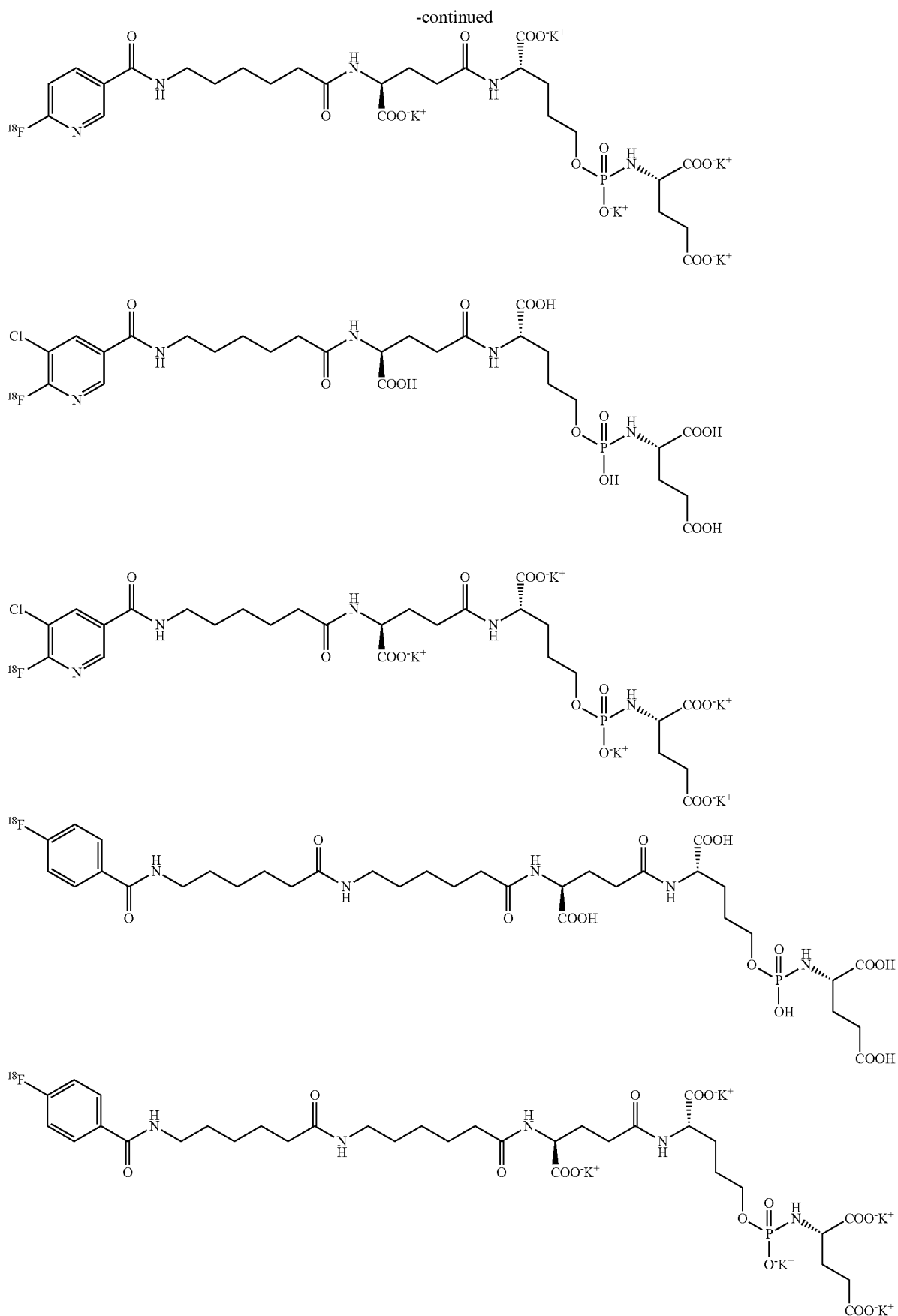

-continued
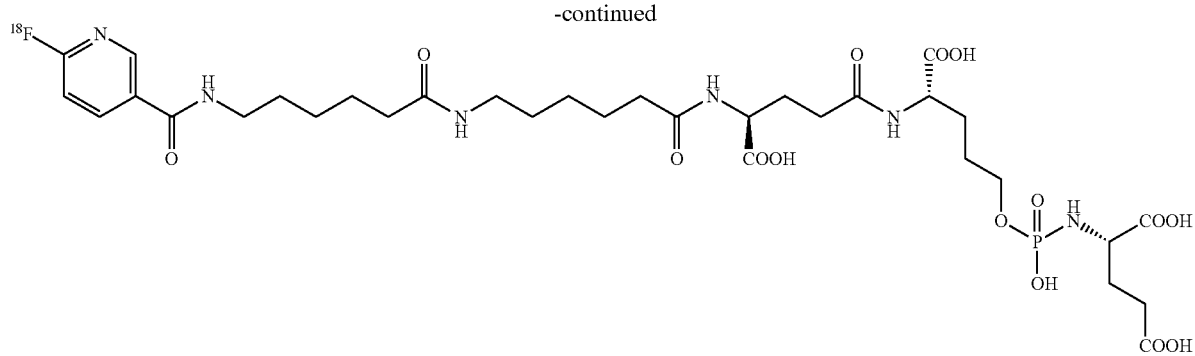
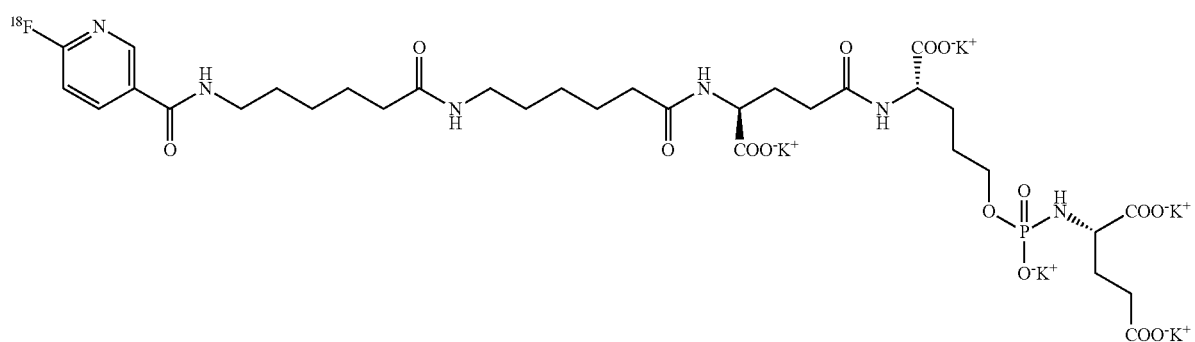
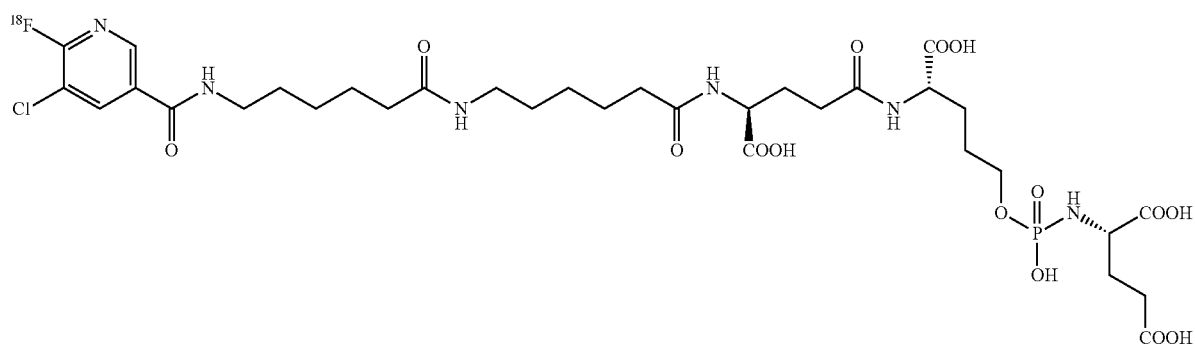
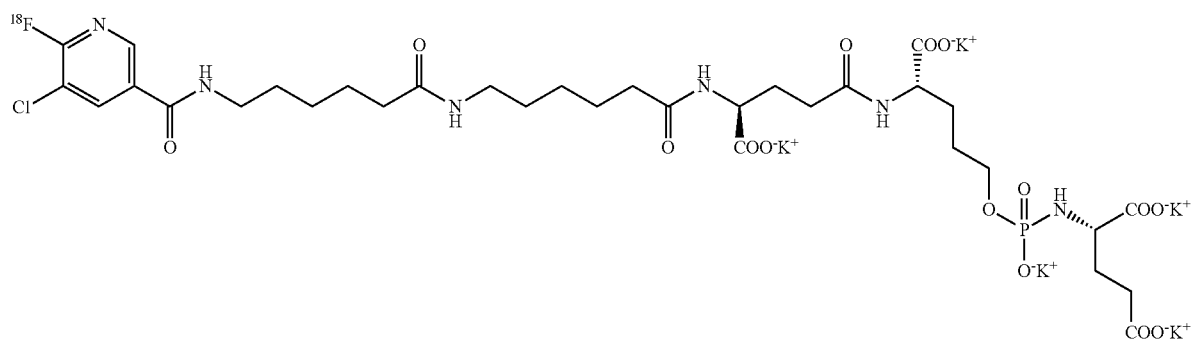
and other pharmaceutically acceptable salts thereof, such as, for example, sodium.

In another embodiment, the compound of formula (I) is
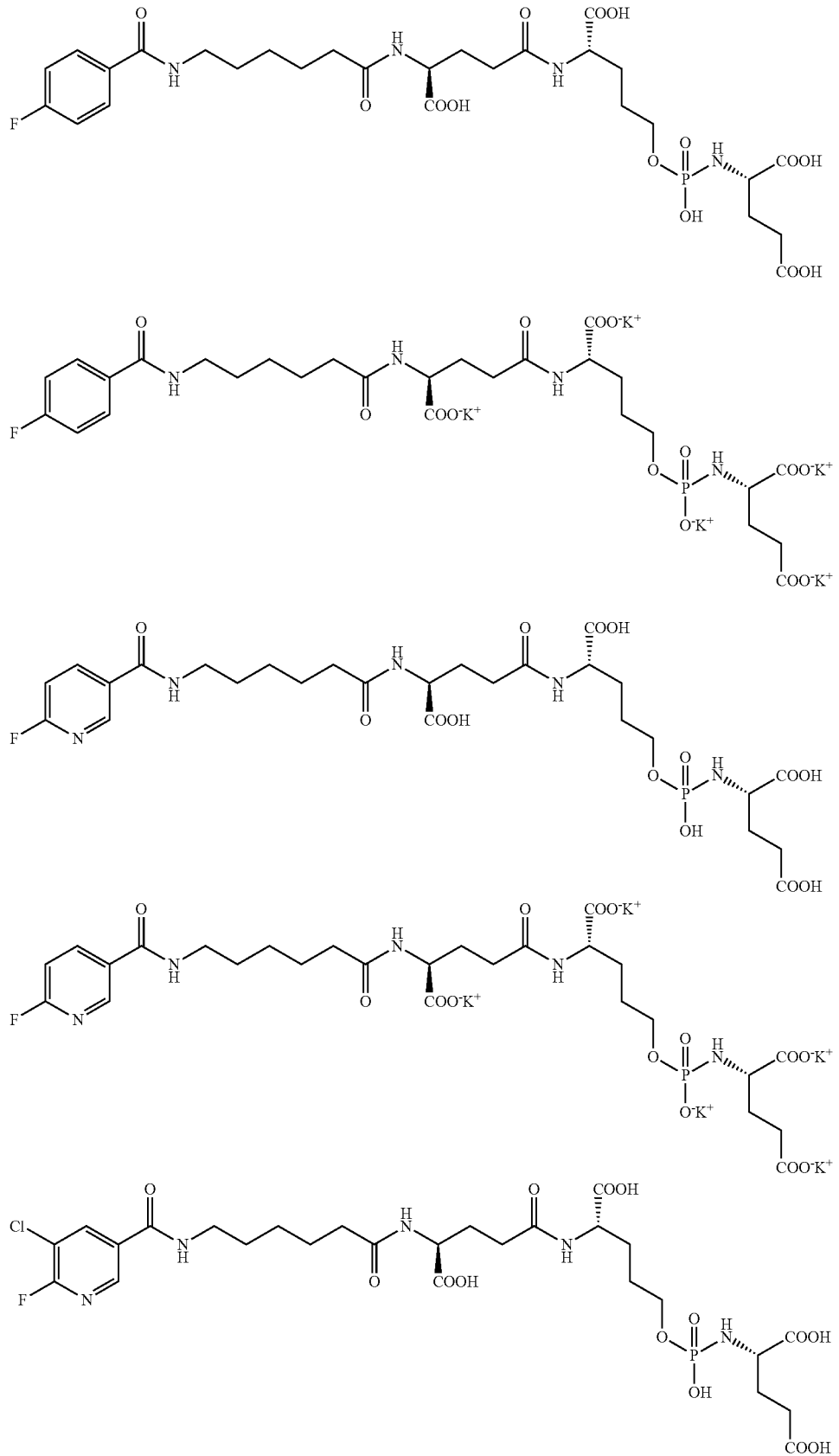

-continued
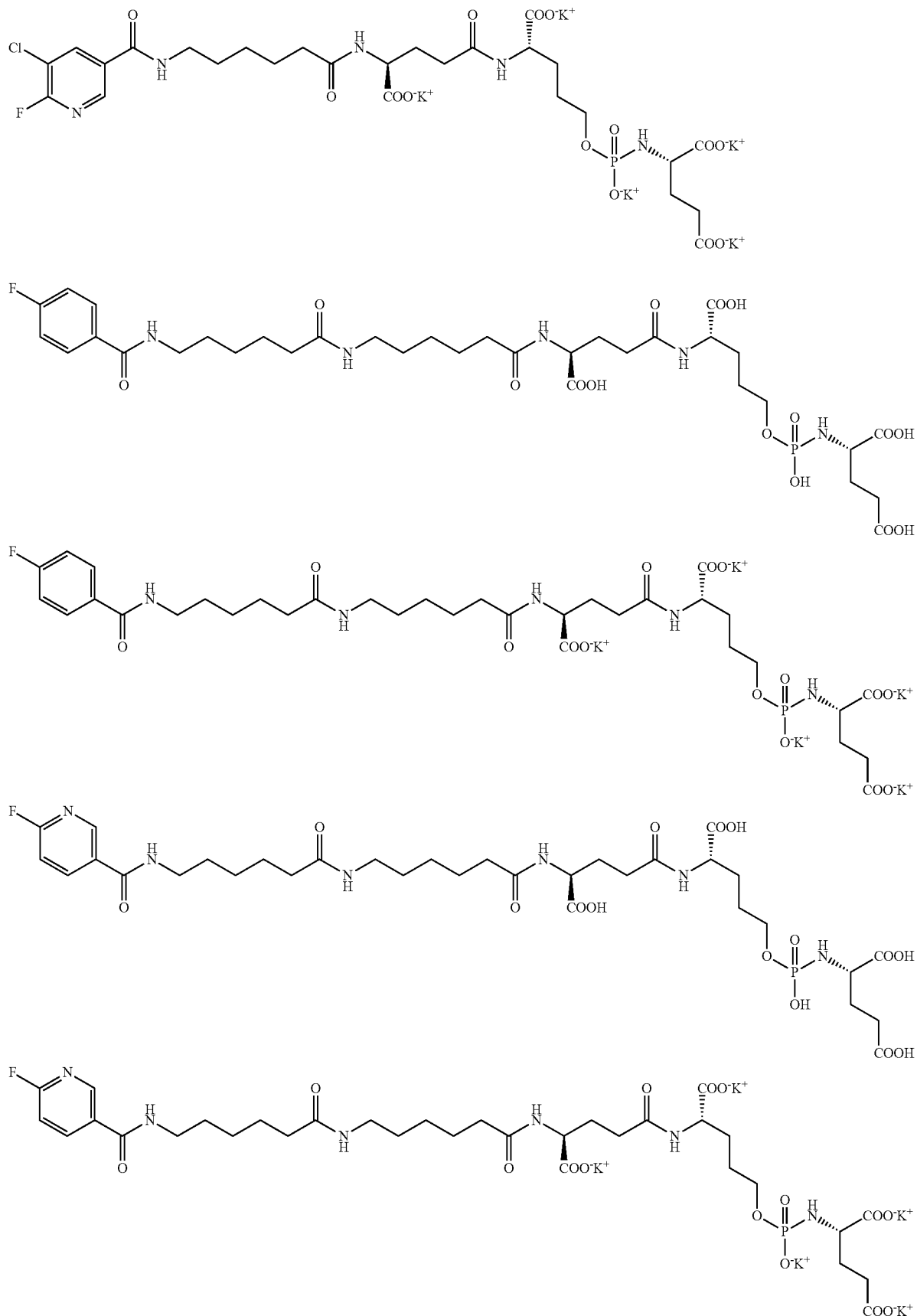

-continued

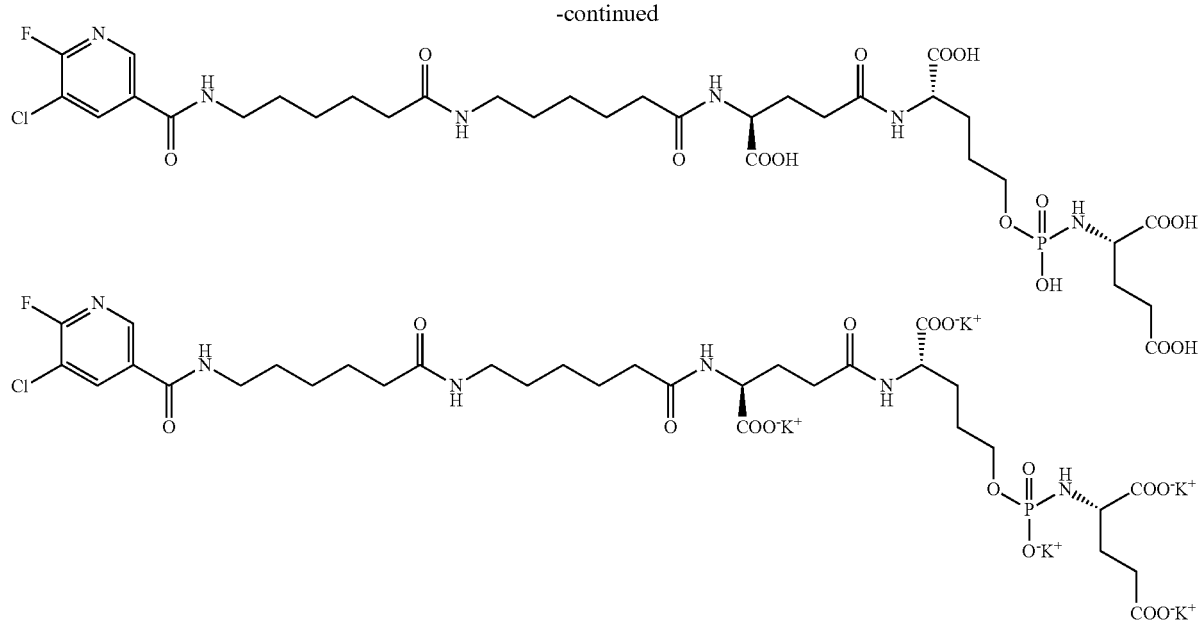

and other pharmaceutically acceptable salts thereof, such as, for example, sodium.

In another aspect, the invention comprises compounds of formula (II):

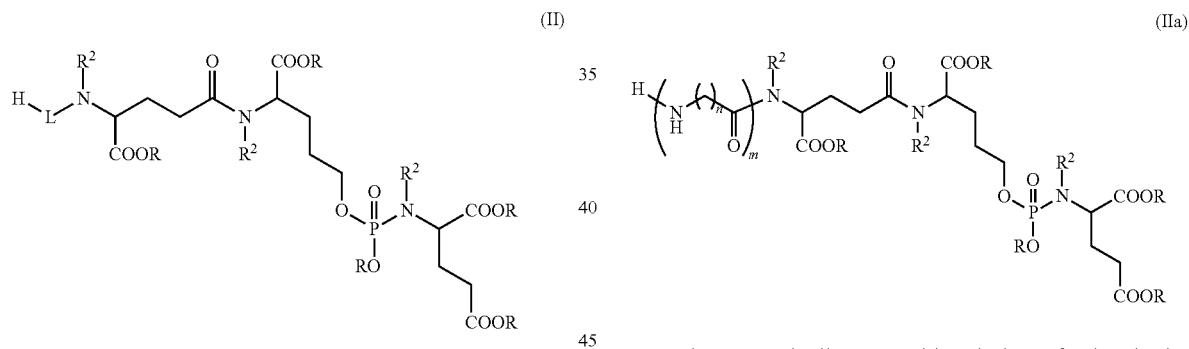

or a pharmaceutically acceptable salt thereof, wherein the definitions of L, R², and R are defined above for the compound of formula (I) and include compounds in which m is any one of (2a)-(2o), each n is independently any one of (3a)-(3x), each R² is independently any of (4a)-(4v), and each R is independently any one of (5a)-(5w).

In certain embodiments, the compound for formula (II) is of the formula (IIa):

or a pharmaceutically acceptable salt thereof, wherein the definitions of m, n, R², and R are defined above for the compound of formula (I).

In certain embodiments, the compound for formula (II) is of the formula (IIb):

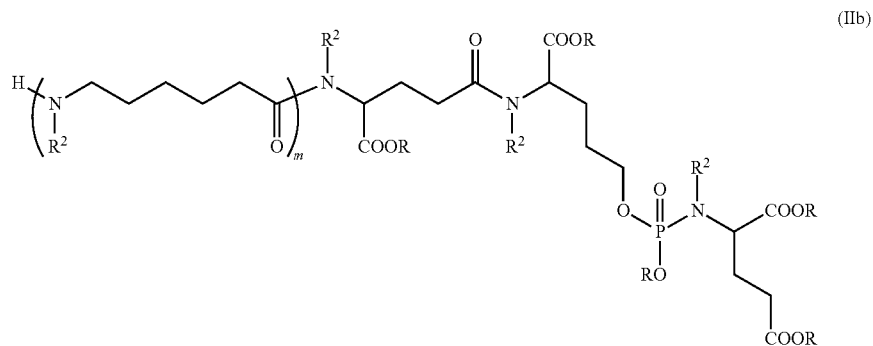

or a pharmaceutically acceptable salt thereof, wherein the definitions of m, n, $R^2$, and R are defined above for the compound of formula (II).

In some embodiments of the compounds of formula (IIb), m is 1, and each R and $R^2$ is hydrogen. In other embodiments, m is 2, and each R and $R^2$ are hydrogen.

Genera of compounds according to this aspect of the invention also include those in which m is any one of (2a)-(2o), each n is independently any one of (3a)-(3x), $R^2$ is any of (4a)-(4v), and each R is independently any one of (5a)-(5w). Representative but non-exclusive examples are described in the following paragraph.

Particular embodiments according to this aspect of the invention include compounds of formula (II) as defined in each of the following rows, in which each entry is a group number as defined above (e.g., (4k) indicates that $R^2$ is methyl), and a dash "-" indicates that the variable is as defined for formula (II) or is defined according to any applicable variable definition above (e.g., when a cell in the m column is "-", m can be defined as for formula (II) or any one of definitions (2a)-(2o)).

| Form. (II) | m | L n | $R^2$ | R |
|---|---|---|---|---|
| II | 2a | 3a | 4a | 5a |
| II | 2b | 3g | 4c | 5b |
| II | 2d | 3m | 4k | 5c |
| II | 2f | 3n | 4l | 5v |
| II | 2h | 3q | 4m | 5w |
| II | 2m | 3l | 4o | 5a |
| II | 2l | 3c | 4a | 5b |
| II | 2c | 3a | 4c | 5c |
| II | 2n | 3g | 4k | 5v |
| II | 2a | 3m | 4l | 5w |
| II | 2b | 3n | 4m | 5a |
| II | 2d | 3q | 4o | 5b |
| II | 2f | 3l | 4a | 5c |
| II | 2h | 3c | 4c | 5v |
| II | 2m | 3q | 4k | 5w |
| II | 2l | 3l | 4l | 5a |
| II | 2c | 3c | 4m | 5b |
| II | 2a | 3n | 4o | 5c |
| II | 2b | 3q | 4a | 5v |
| II | 2d | 3l | 4c | 5w |
| II | 2f | 3c | 4k | 5a |
| II | 2h | 3a | 4l | 5b |
| II | 2m | 3g | 4m | 5c |
| II | 2l | 3m | 4o | 5b |
| II | 2a | 3n | 4a | 5c |
| II | 2b | 3q | 4c | 5v |
| IIa | 2b | 3q | 4a | 5v |
| IIa | 2d | 3l | 4c | 5w |
| IIa | 2f | 3c | 4k | 5a |
| IIa | 2h | 3a | 4l | 5b |
| IIa | 2m | 3g | 4m | 5c |
| IIa | 2l | 3m | 4o | 5b |
| IIa | 2a | 3n | 4a | 5c |
| IIa | 2b | 3q | 4c | 5v |
| IIa | 2b | 3l | 4a | 5v |
| IIa | 2d | 3c | 4c | 5w |
| IIa | 2f | 3q | 4k | 5a |
| IIa | 2h | 3l | 4l | 5a |
| IIa | 2m | 3n | 4m | 5b |
| IIa | 2l | 3q | 4o | 5c |
| IIa | 2c | 3l | 4a | 5v |
| IIa | 2n | 3c | 4c | 5w |
| IIa | 2a | 3a | 4k | 5a |
| IIa | 2b | 3g | 4l | 5b |
| IIa | 2d | 3m | 4m | 5c |
| IIa | 2f | 3m | 4o | 5w |
| IIa | 2h | 3n | 4a | 5a |
| IIa | 2d | 3q | 4c | 5b |
| IIa | 2d | 3g | 4k | 5w |
| IIa | 2f | 3m | 4l | 5a |
| IIa | 2h | 3n | 4m | 5b |
| IIa | 2m | 3q | 4o | 5c |
| IIa | 2f | 3g | 4k | 5c |
| IIb | 2l | — | 4a | 5v |
| IIb | 2m | — | 4b | 5a |
| IIb | 2h | — | 4c | 5b |
| IIb | 2l | — | 4a | 5w |
| IIb | 2h | — | 4c | 5v |
| IIb | 2l | — | 4a | 5a |
| IIb | 2m | — | 4b | 5b |
| IIb | 2h | — | 4c | 5w |
| IIb | 2l | — | 4a | 5v |
| IIb | 2m | — | 4b | 5a |
| IIb | 2h | — | 4c | 5b |
| IIb | 2l | — | 4b | 5v |
| IIb | 2m | — | 4c | 5a |
| IIb | 2h | — | 4a | 5b |
| IIb | 2l | — | 4c | 5b |
| IIb | 2h | — | 4c | 5v |
| IIb | 2l | — | 4a | 5a |
| IIb | 2m | — | 4b | 5b |
| IIb | 2h | — | 4c | 5w |
| IIb | 2l | — | 4b | 5c |
| IIb | 2m | — | 4c | 5v |
| IIb | 2l | — | 4c | 5b |
| IIb | 2m | — | 4c | 5w |
| IIb | 2h | — | 4a | 5v |
| IIb | 2l | — | 4b | 5a |
| IIb | 2m | — | 4c | 5b |
| IIb | 2l | — | 4c | 5b |
| IIb | 2l | — | 4a | 5b |
| IIb | 2m | — | 4b | 5v |
| IIb | 2h | — | 4c | 5a |
| IIb | 2l | — | 4c | 5b |
| IIb | 2m | — | 4c | 5b |
| IIb | 2h | — | 4a | 5c |
| IIb | 2l | — | 4b | 5v |
| IIb | 2m | — | 4c | 5a |
| IIb | 2l | — | 4b | 5w |
| IIb | 2h | — | 4b | 5a |
| IIb | 2m | — | 4a | 5b |
| IIb | 2h | — | 4b | 5v |
| IIb | 2l | — | 4c | 5a |
| IIb | 2h | — | 4a | 5w |
| IIb | 2h | — | 4a | 5a |
| IIb | 2l | — | 4b | 5b |

In particular embodiments of the compounds of formulae (II), (IIa) and (IIb), the compound can be of the formula (II*), (IIa*) or (IIb*):

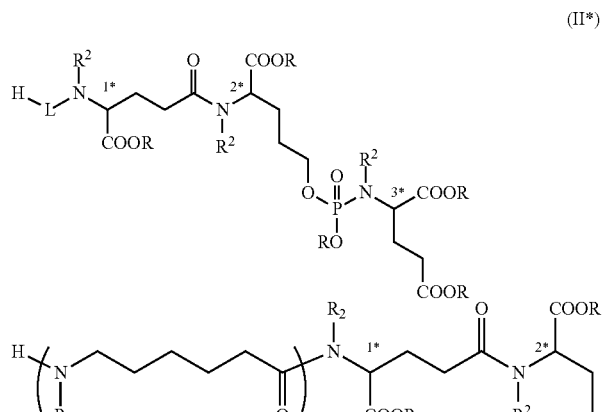

(II*)

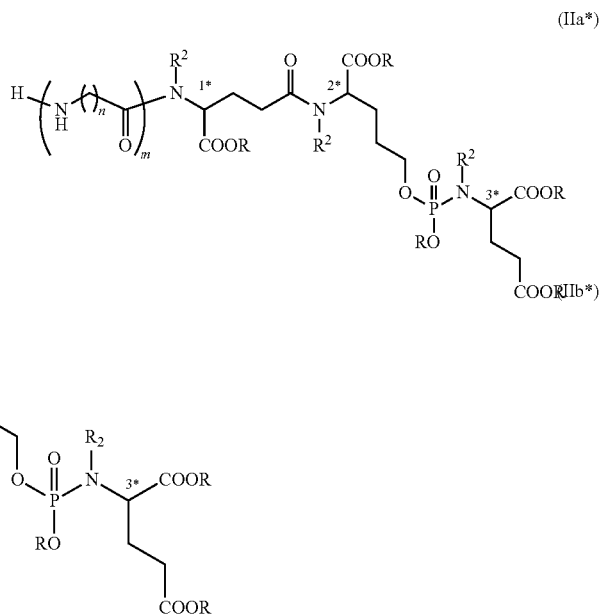

(IIa*)

(IIb*)

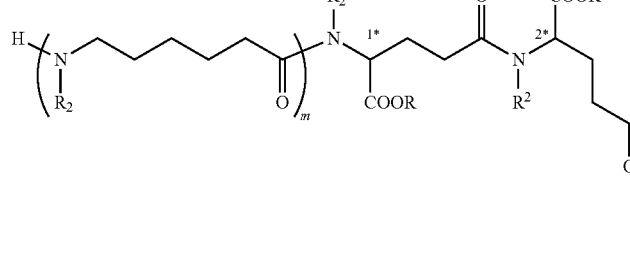

and a pharmaceutically acceptable salt thereof, wherein m, n, $R^2$, and R are as defined according to any one of the embodiments described above for formulae (II), (IIa) and (IIb), and the stereoconfiguration of 1*, 2*, and 3* are as defined above for compounds of formulae (I*), (Ia*) and (Ib*).

In an embodiment of any of the preceding embodiments of the compounds of formula (IIa*), the compound can be of the formula (IIc):

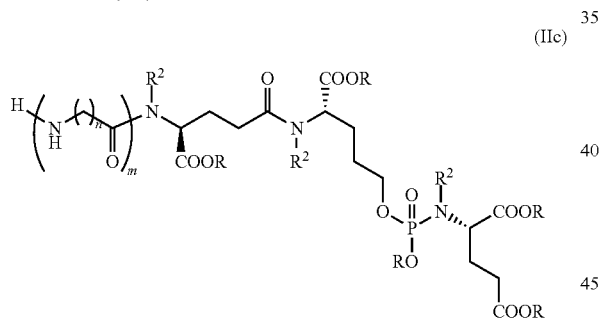

(IIc)

and pharmaceutically acceptable salts thereof.

In an embodiment of any of the preceding embodiments of the compounds of formula (IIb*), the compound can be of the formula (IId):

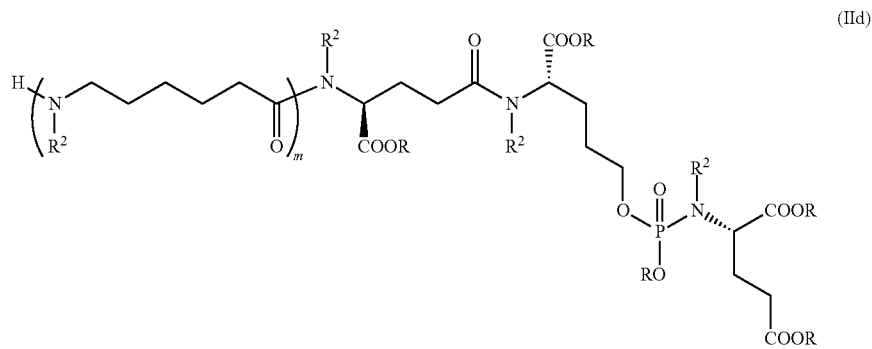

(IId)

and pharmaceutically acceptable salts thereof.

In another embodiment, the compound of formula (II) is
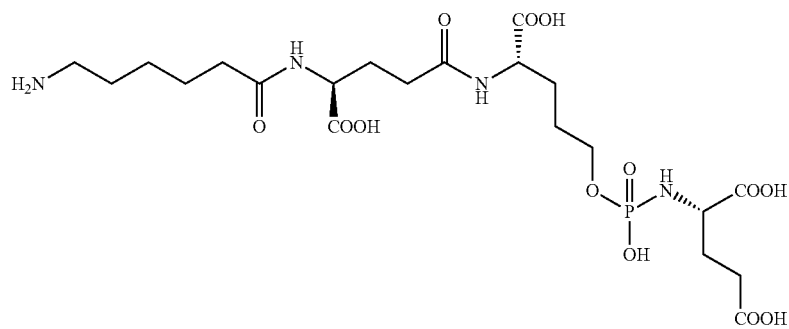
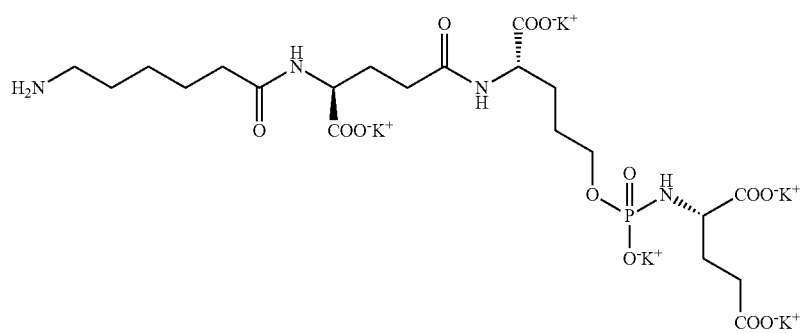
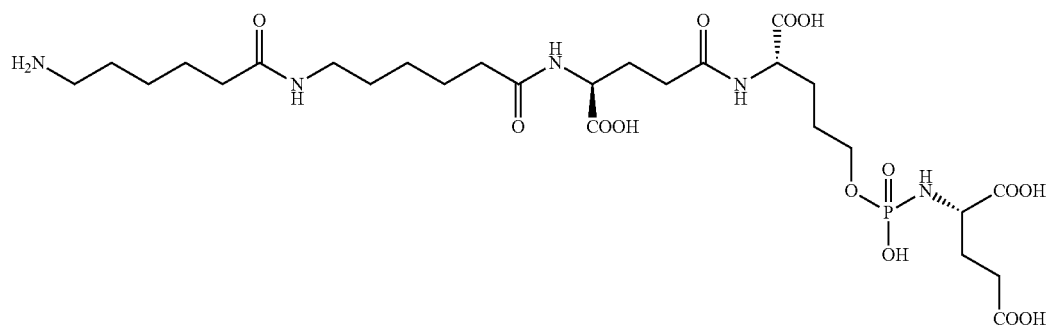
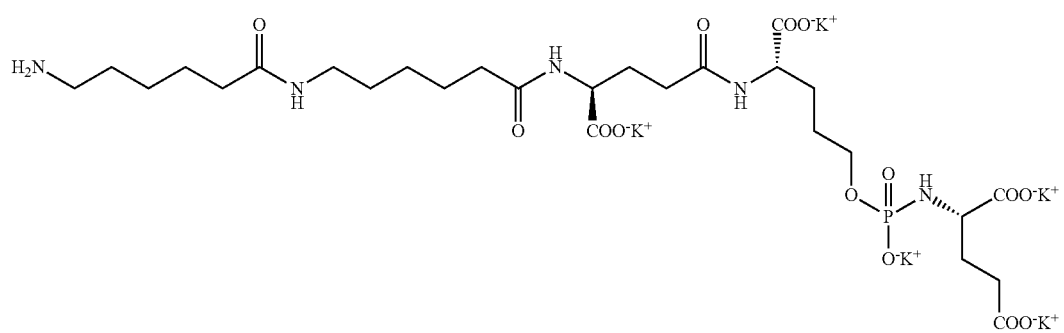
and other pharmaceutically acceptable salts thereof, such as, for example, sodium.

In another embodiment, the compound of formula (II) is
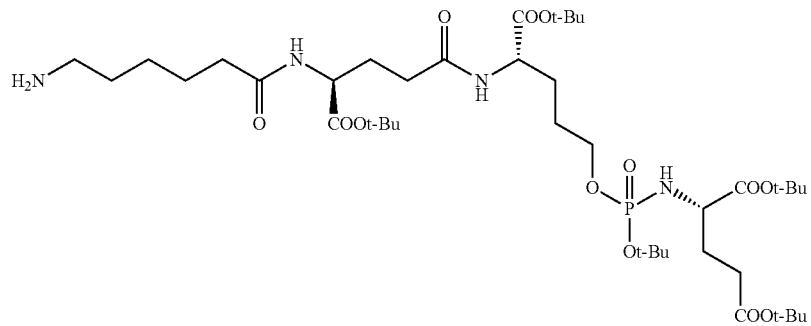
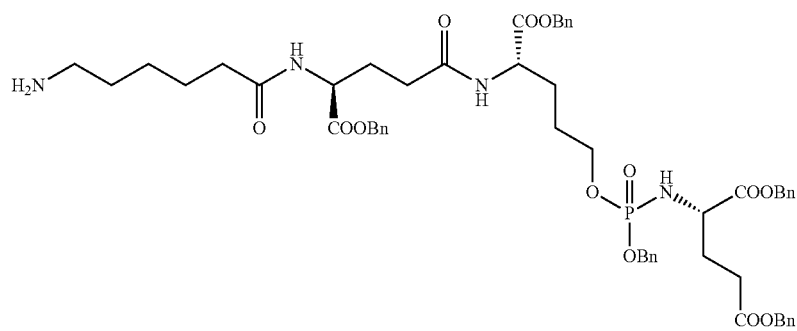
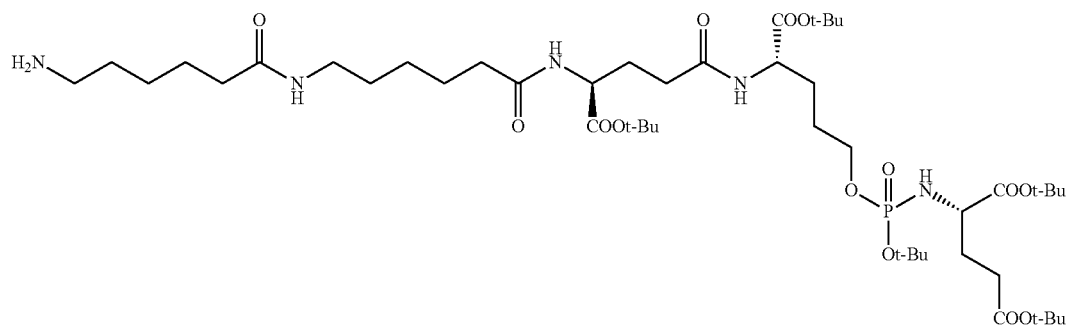
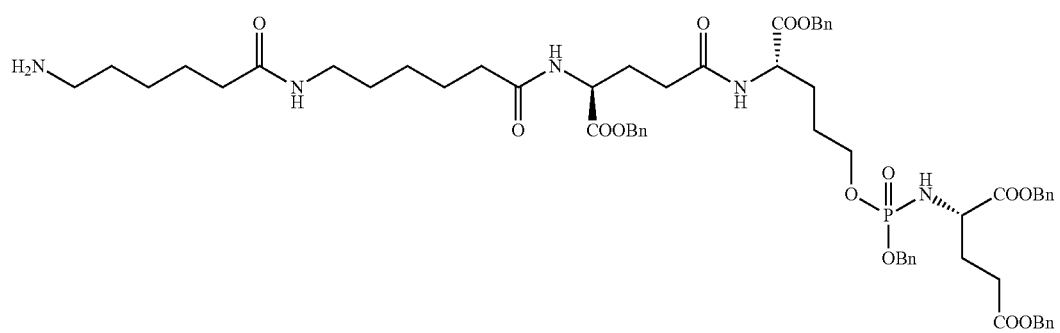
and other pharmaceutically acceptable salts thereof, such as, for example, sodium.
In another aspect, the invention comprises compounds that are in the form of formula (III),

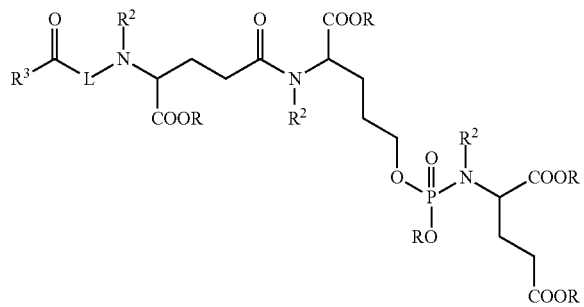

(III)

and pharmaceutically acceptable salts thereof, wherein the definitions of L, $R^2$, and R are defined above for the compound of formula (I), and include compounds in which m is any one of (2a)-(2o), each n is independently any one of (3a)-(3x), each $R^2$ is independently any of (4a)-(4v), and each R is independently any one of (5a)-(5w). $R^3$ is phenyl or pyridyl; wherein the phenyl or pyridyl is substituted with a leaving group and optionally substituted with a second group selected from halogen, cyano, and nitro.

A "leaving group" as used herein, is a chemical entity that is capable of being displaced from a phenyl or pyridyl ring under $S_NAr$ conditions as familiar to those skilled in the art. For example, see March, J., *Advanced Organic Chemistry*, $4^{th}$ Ed. (1992), at pages 642-644, which are hereby incorporated by reference in their entirety. Leaving groups include, but are not limited to nitro, trimethylstannyl, benzotriazol-1-yloxy, halogen (e.g., chloro, bromo, iodo), $C_1$-$C_{10}$alkylsulfonate (e.g., mesylate ($CH_3S(O)_2O^-$)), $C_1$-$C_{10}$ haloalkylsulfonate (e.g., triflate ($CF_3S(O)_2O^-$), nonaflate ($CF_3CF_2CF_2CF_2S(O)_2O^-$)), or phenylsulfonate (e.g., besylate), wherein the phenyl is optionally substituted with 1, 2, or 3 groups which are each independently halogen or $C_1$-$C_4$ alkyl (e.g., 2,4,6-trimethylbenzenesulfonate, or 2,4,6-triisopropylbenzenesulfonate). A "leaving group" may also be an ammonium salt of the formula —$N(R^x)(R^y)(R^z)]^+$ $[X]^-$, wherein $R^x$, $R^y$, and $R^z$ are independently hydrogen, or alkyl (e.g., methyl, ethyl, propyl), and X is the conjugate base of a strong acid. Options for X include, but are not limited to, halogen (e.g., chloro, bromo, iodo), $C_1$-$C_{10}$alkylsulfonate (e.g., mesylate ($CH_3S(O)_2O^-$)), $C_1$-$C_{10}$ haloalkylsulfonate (e.g., triflate ($CF_3S(O)_2O^-$), nonaflate ($CF_3CF_2CF_2CF_2S(O)_2O^-$)), or phenylsulfonate (e.g., besylate), wherein the phenyl is optionally substituted with 1, 2, or 3 groups which are each independently halogen or $C_1$-$C_4$ alkyl (e.g., 2,4,6-trimethylbenzenesulfonate, or 2,4,6-triisopropylbenzenesulfonate). A "trialkylammonium salt" is an ammonium salt where $R^x$, $R^y$, and $R^z$ are not hydrogen, and X is as described above. A "trimethylammonium salt" is a trialkylammonium salt where $R^x$, $R^y$, and $R^z$ are methyl, and X is as described above.

In an embodiment of any of the preceding embodiments of formula (III), the leaving group is halogen (e.g., chloro) or trialkylammonium (e.g., trimethylammonium).

In certain embodiments of the compound of formula (III), the compound is of the formula (IIIa):

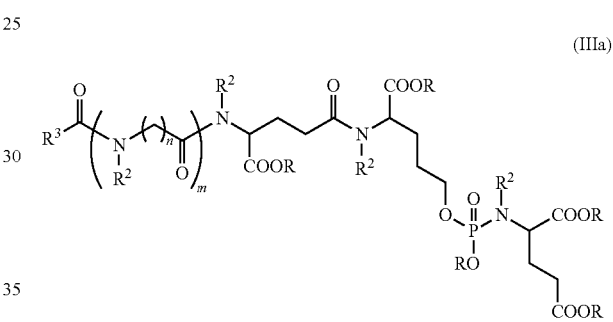

(IIIa)

or a pharmaceutically acceptable salt thereof, wherein the definitions of m, n, $R^2$, and R are defined above for the compound of formula (I).

In certain embodiments of the compound of formula (III), the compound is of the formula (IIIb):

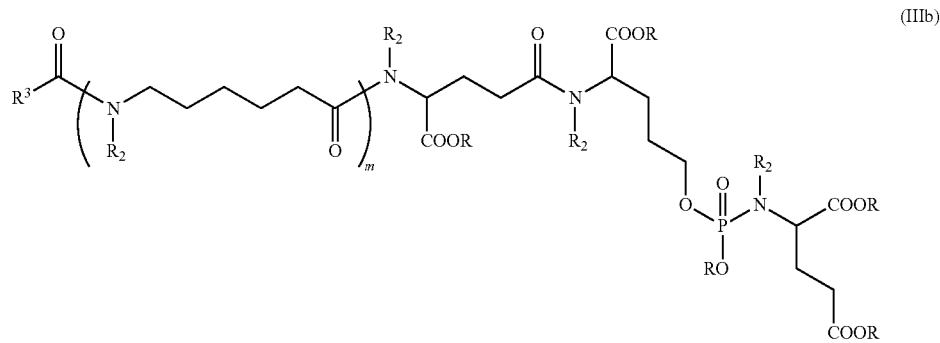

(IIIb)

and pharmaceutically acceptable salts thereof.

In some embodiments of the compounds of formula (IIIb), m is 1, and each R and $R^2$ are hydrogen. In other embodiments, m is 2, and each R and $R^2$ are hydrogen.

In certain embodiments of the compounds of formulae (III), (IIIa) and (IIIb), $R^3$ is selected from one of the following groups (6a)-(6ss):

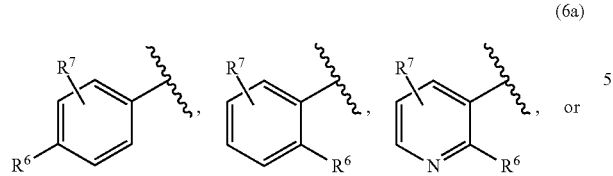
(6a)

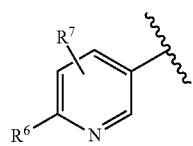

wherein $R^6$ is a leaving group; and $R^7$ is halogen, cyano or nitro.

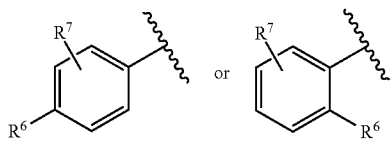
(6b)

wherein $R^6$ a leaving group; and $R^7$ is halogen, cyano or nitro.

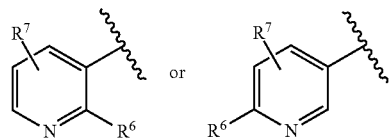
(6c)

wherein $R^6$ is a leaving group; and $R^7$ is halogen, cyano or nitro.

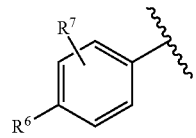
(6d)

wherein $R^6$ is a leaving group; and $R^7$ is halogen, cyano or nitro.

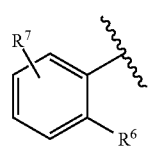
(6e)

wherein $R^6$ is a leaving group; and $R^7$ is halogen, cyano or nitro.

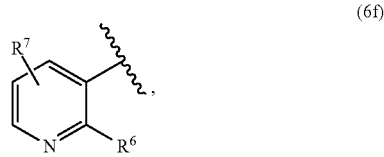
(6f)

wherein $R^6$ is a leaving group; and $R^7$ is halogen, cyano or nitro.

(6g)

wherein $R^6$ is a leaving group; and $R^7$ is halogen, cyano or nitro.

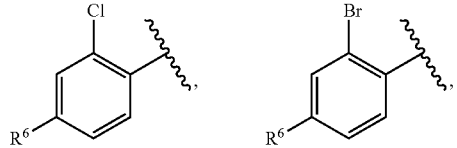

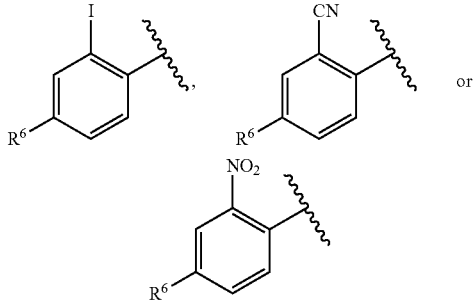
(6h)

wherein $R^6$ is a leaving group.

(6i)
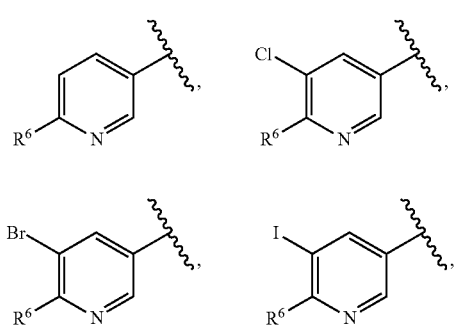
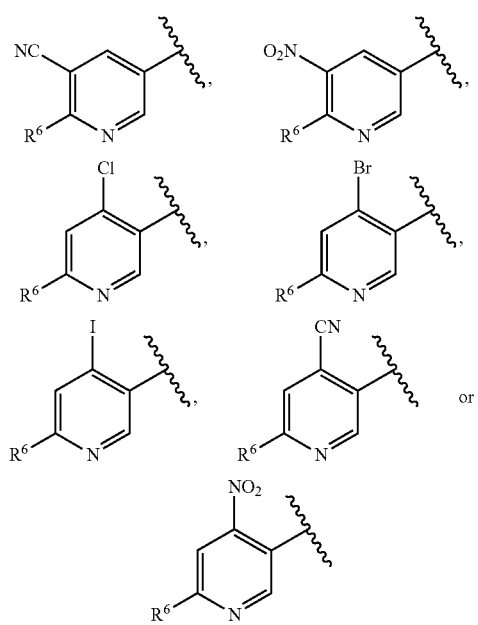
or
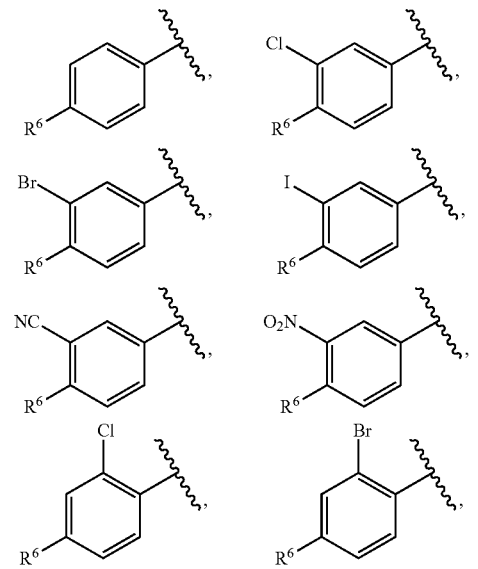
wherein $R^6$ is a leaving group.
(6j)
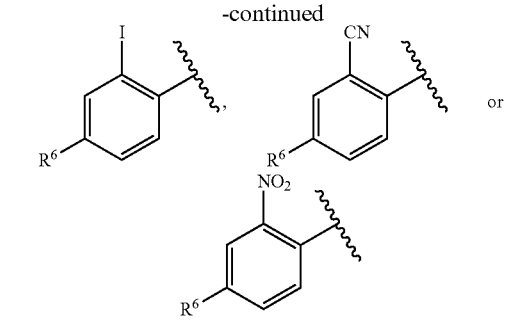
wherein $R^6$ is halogen.
(6k)
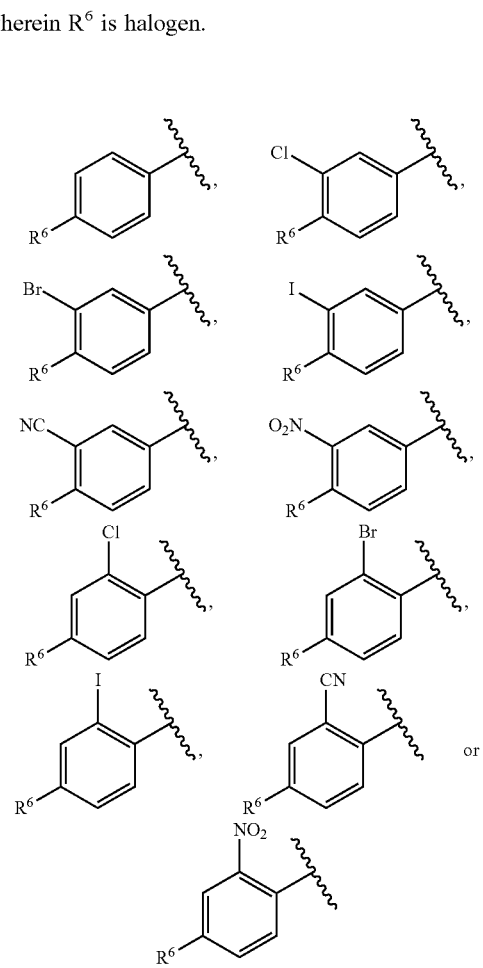
wherein $R^6$ is chloro.
(6l)
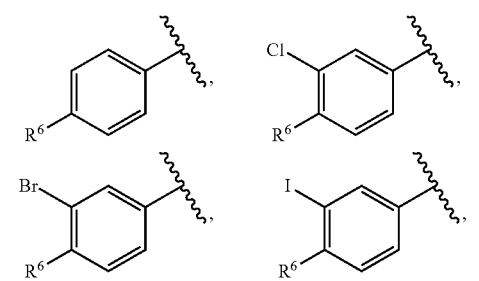

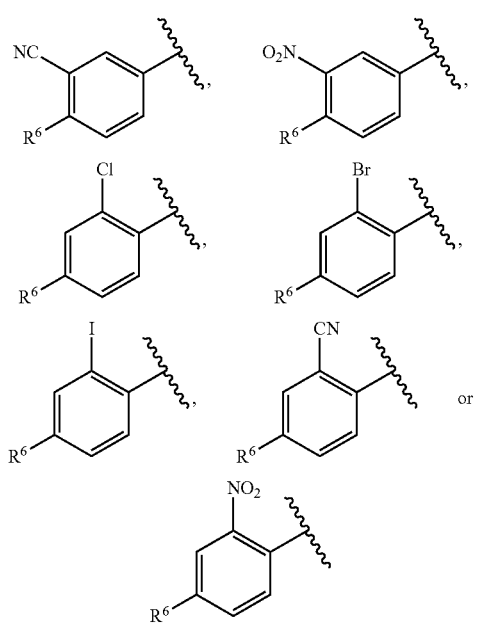
wherein R⁶ is trialkylammonium salt.
(6m)
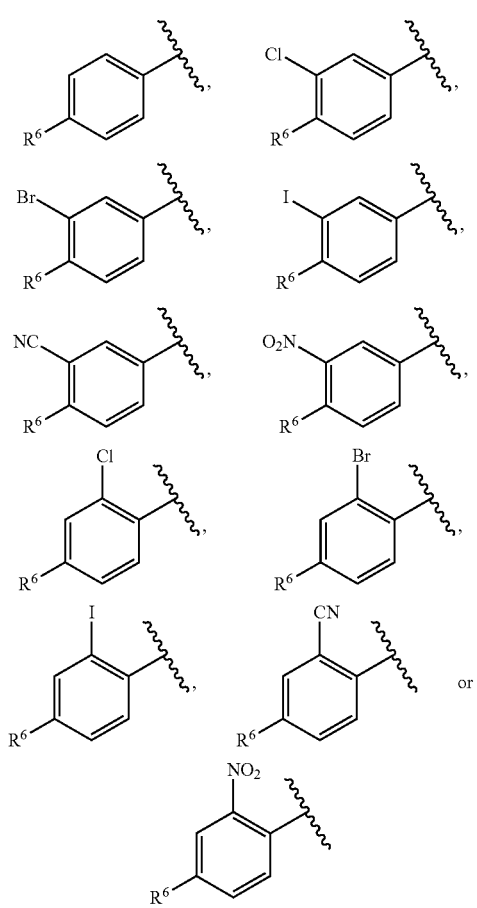
wherein R⁶ is trimethylammonium salt.
(6n)
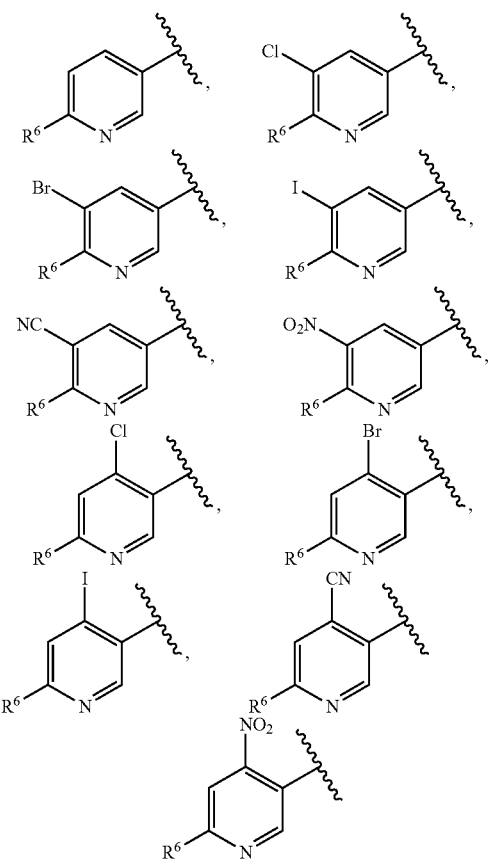
wherein R⁶ is halogen.
(6o)
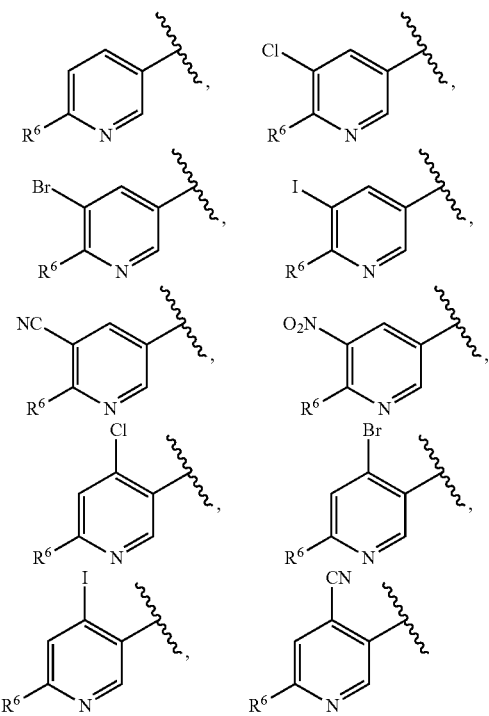

-continued
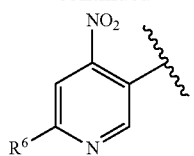
wherein R⁶ is chloro.
(6p)
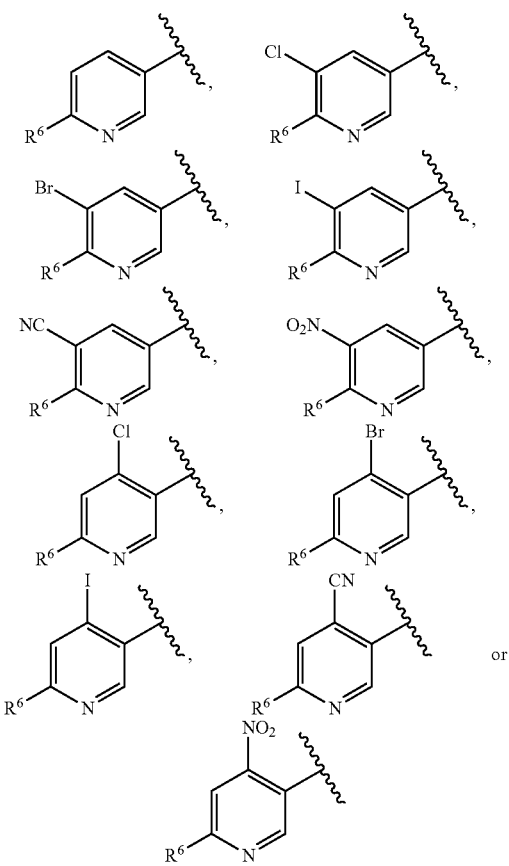
wherein R⁶ is trialkylammonium salt.
(6q)
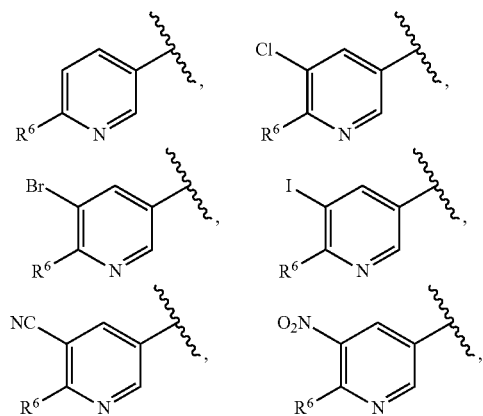
-continued
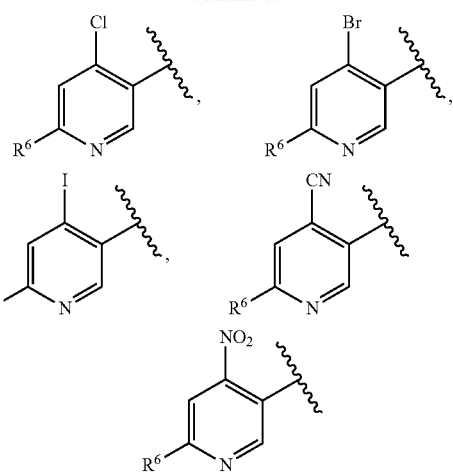
wherein R⁶ is trimethylammonium salt.
(6r)
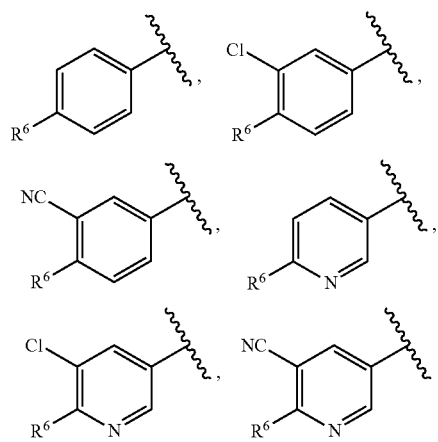
wherein R⁶ is halogen.
(6s)
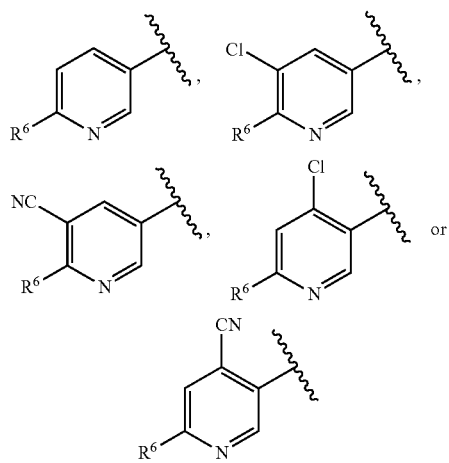
wherein R⁶ is halogen.

(6t)
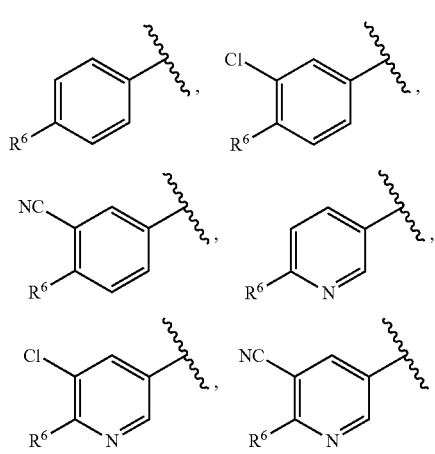
wherein R⁶ is chloro.
(6u)
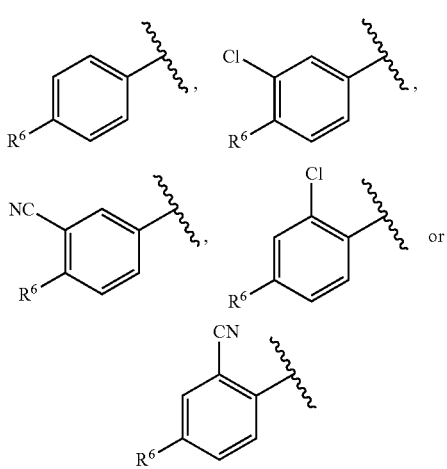
wherein R⁶ is a trialkylammonium salt.
(6v)
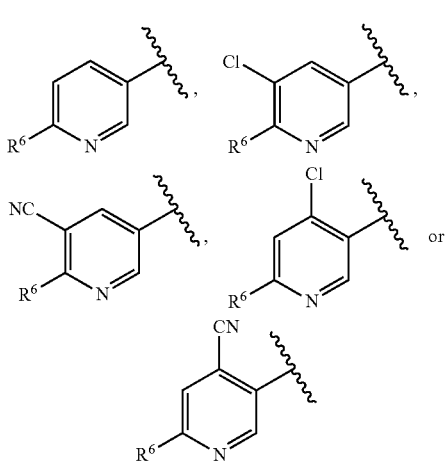
wherein R⁶ is chloro.
(6w)
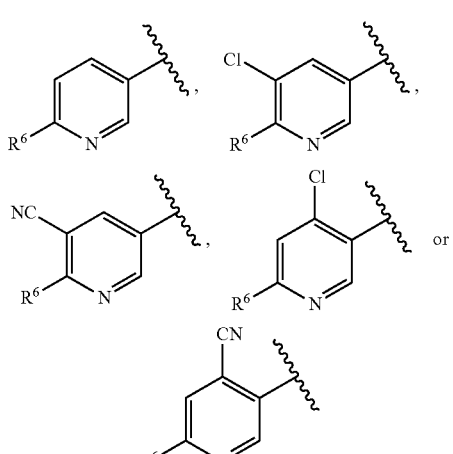
wherein R⁶ is a trialkylammonium salt.
(6x)
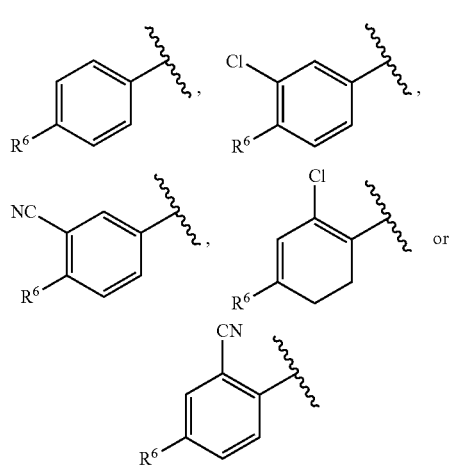
wherein R⁶ is trimethylammonium.
(6y)
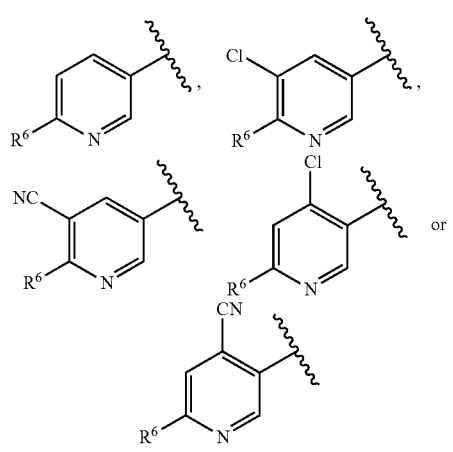
wherein R⁶ is trimethylammonium.

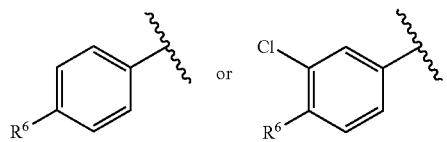 (6z)
wherein R⁶ is a leaving group.
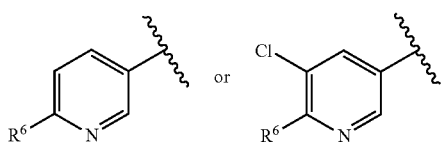 (6gg)
wherein R⁶ is chloro.
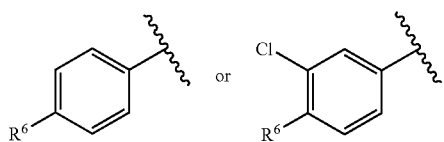 (6aa)
wherein R⁶ is halogen.
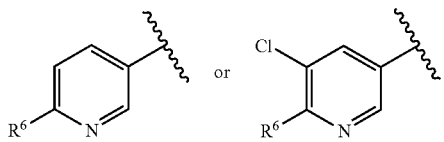 (6hh)
wherein R⁶ is a trialkylammonium salt.
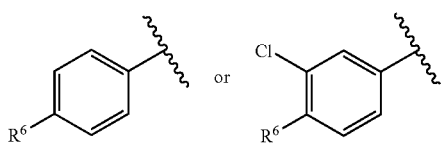 (6bb)
wherein R⁶ is chloro.
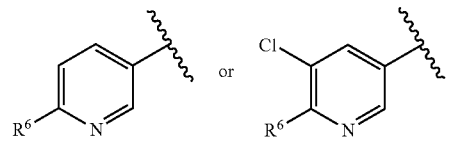 (6ii)
wherein R⁶ is trimethylammonium.
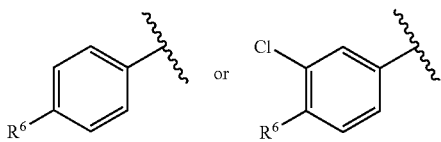 (6cc)
wherein R⁶ is a trialkylammonium salt.
(6dd)
wherein R⁶ is trimethylammonium.
(6ee)
wherein R⁶ is a leaving group.
(6ff)
wherein R⁶ is halogen.
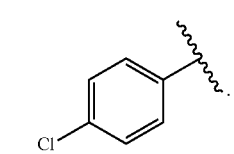 (6jj)
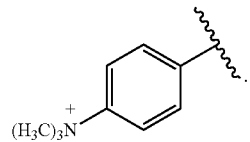 (6kk)
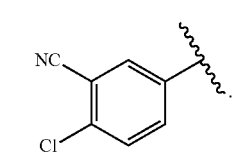 (6ll)

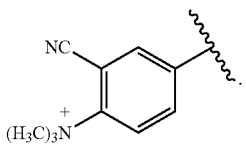
(6mm)

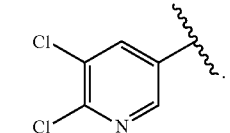
(6nn)

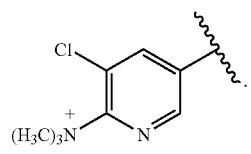
(6oo)

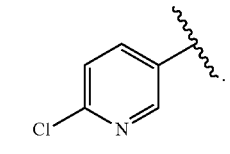
(6pp)

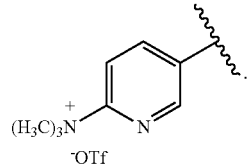
(6qq)

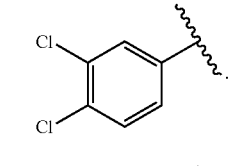
(6rr)

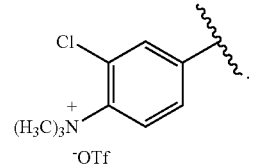
(6ss)

Genera of compounds according to this aspect of the invention also include those in which R³ is any one of (6a)-(6ss), m is any one of (2a)-(2o), each n is independently any one of (3a)-(3x), each R² is independently any of (4a)-(4v), and each R is independently any one of (5a)-(5w). Representative but non-exclusive examples are described in the following paragraph.

Particular embodiments according to this aspect of the invention include compounds of formula (III) as defined in each of the following rows, in which each entry is a group number as defined above (e.g., (4k) indicates that R² is methyl), and a dash "-" indicates that the variable is as defined for formula (III) or is defined according to any applicable variable definition above (e.g., when a cell in the R³ column is "-", R³ can be defined as for formula (III) or any one of definitions (6a)-(6ss)).

| Form. (III) | R³ | L m | L n | R² | R |
|---|---|---|---|---|---|
| III | 6a | 2a | 3a | 4a | 5a |
| III | 6d | 2b | 3g | 4c | 5b |
| III | 6g | 2d | 3m | 4k | 5c |
| III | 6k | 2f | 3n | 4l | 5v |
| III | 6w | 2h | 3q | 4m | 5w |
| III | 6u | 2m | 3l | 4o | 5a |
| III | 6s | 2l | 3c | 4a | 5b |
| III | 6q | 2c | 3a | 4c | 5c |
| III | 6z | 2n | 3g | 4k | 5v |
| III | 6n | 2a | 3m | 4l | 5w |
| III | 6jj | 2b | 3n | 4m | 5a |
| III | 6kk | 2d | 3q | 4o | 5b |
| III | 6ll | 2f | 3l | 4a | 5c |
| III | 6jj | 2h | 3c | 4c | 5v |
| III | 6nn | 2m | 3q | 4k | 5w |
| III | 6oo | 2l | 3l | 4l | 5a |
| III | 6pp | 2c | 3c | 4m | 5b |
| III | 6qq | 2a | 3n | 4o | 5c |
| III | 6e | 2b | 3q | 4a | 5v |
| III | 6u | 2d | 3l | 4c | 5w |
| III | 6p | 2f | 3c | 4k | 5a |
| III | 6c | 2h | 3a | 4l | 5b |
| III | 6f | 2m | 3g | 4m | 5c |
| III | 6g | 2l | 3m | 4o | 5b |
| III | 6j | 2a | 3n | 4a | 5c |
| III | 6t | 2b | 3q | 4c | 5v |
| III | 6y | 2d | 3g | 4k | 5w |
| III | 6x | 2f | 3m | 4l | 5a |
| III | 6d | 2h | 3n | 4m | 5b |
| III | 6mm | 2m | 3q | 4o | 5c |
| III | 6a | 2b | 3l | 4a | 5v |
| III | 6d | 2d | 3c | 4c | 5w |
| III | 6g | 2f | 3q | 4k | 5a |
| III | 6k | 2h | 3l | 4l | 5a |
| III | 6w | 2m | 3n | 4m | 5b |
| III | 6u | 2l | 3q | 4o | 5c |
| III | 6s | 2c | 3l | 4a | 5v |
| III | 6q | 2n | 3c | 4c | 5w |
| III | 6z | 2a | 3a | 4k | 5a |
| III | 6n | 2b | 3g | 4l | 5b |
| III | 6jj | 2d | 3m | 4m | 5c |
| III | 6kk | 2f | 3m | 4o | 5w |
| III | 6ll | 2h | 3n | 4a | 5a |
| III | 6jj | 2d | 3q | 4c | 5b |
| III | 6nn | 2f | 3g | 4k | 5c |
| IIIa | 6oo | 2a | 3a | 4a | 5a |
| IIIa | 6pp | 2b | 3g | 4c | 5b |
| IIIa | 6qq | 2d | 3m | 4k | 5c |
| IIIa | 6e | 2f | 3n | 4l | 5v |
| IIIa | 6u | 2h | 3q | 4m | 5w |
| IIIa | 6p | 2m | 3l | 4o | 5a |
| IIIa | 6c | 2l | 3c | 4a | 5b |
| IIIa | 6f | 2c | 3a | 4c | 5c |
| IIIa | 6g | 2n | 3g | 4k | 5v |
| IIIa | 6j | 2a | 3m | 4l | 5w |
| IIIa | 6t | 2b | 3n | 4m | 5a |
| IIIa | 6y | 2d | 3q | 4o | 5b |
| IIIa | 6x | 2f | 3l | 4a | 5c |
| IIIa | 6d | 2h | 3c | 4c | 5v |
| IIIa | 6mm | 2m | 3q | 4k | 5w |
| IIIa | 6a | 2l | 3l | 4l | 5a |
| IIIa | 6d | 2c | 3c | 4m | 5b |
| IIIa | 6g | 2a | 3n | 4o | 5c |
| IIIa | 6k | 2b | 3q | 4a | 5v |
| IIIa | 6w | 2d | 3l | 4c | 5w |
| IIIa | 6u | 2f | 3c | 4k | 5a |
| IIIa | 6s | 2h | 3a | 4l | 5b |
| IIIa | 6q | 2m | 3g | 4m | 5c |
| IIIa | 6z | 2l | 3m | 4o | 5b |
| IIIa | 6n | 2a | 3n | 4a | 5c |
| IIIa | 6jj | 2b | 3q | 4c | 5v |
| IIIa | 6kk | 2d | 3g | 4k | 5w |
| IIIa | 6ll | 2f | 3m | 4l | 5a |
| IIIa | 6jj | 2h | 3n | 4m | 5b |
| IIIa | 6nn | 2m | 3q | 4o | 5c |
| IIIa | 6oo | 2b | 3l | 4a | 5v |
| IIIa | 6pp | 2d | 3c | 4c | 5w |

| Form. (III) | R³ | L m | n | R² | R |
|---|---|---|---|---|---|
| IIIa | 6qq | 2f | 3q | 4k | 5a |
| IIIa | 6e | 2h | 3l | 4l | 5a |
| IIIa | 6u | 2m | 3n | 4m | 5b |
| IIIa | 6p | 2l | 3q | 4o | 5c |
| IIIa | 6c | 2c | 3l | 4a | 5v |
| IIIa | 6f | 2n | 3c | 4c | 5w |
| IIIa | 6g | 2a | 3a | 4k | 5a |
| IIIa | 6j | 2b | 3g | 4l | 5b |
| IIIa | 6t | 2d | 3m | 4m | 5c |
| IIIa | 6y | 2f | 3m | 4o | 5w |
| IIIa | 6x | 2h | 3n | 4a | 5a |
| IIIa | 6d | 2d | 3q | 4c | 5b |
| IIIa | 6mm | 2f | 3g | 4k | 5c |
| IIIb | 6kk | 2l | — | 4a | 5v |
| IIIb | 6ll | 2m | — | 4b | 5a |
| IIIb | 6jj | 2h | — | 4c | 5b |
| IIIb | 6nn | 2l | — | 4a | 5w |
| IIIb | 6oo | 2m | — | 4b | 5c |
| IIIb | 6pp | 2h | — | 4c | 5v |
| IIIb | 6qq | 2l | — | 4a | 5a |
| IIIb | 6e | 2m | — | 4b | 5b |
| IIIb | 6u | 2h | — | 4c | 5w |
| IIIb | 6p | 2l | — | 4a | 5v |
| IIIb | 6c | 2m | — | 4b | 5a |
| IIIb | 6f | 2h | — | 4c | 5b |
| IIIb | 6g | 2l | — | 4b | 5v |
| IIIb | 6j | 2m | — | 4c | 5a |
| IIIb | 6t | 2h | — | 4a | 5b |
| IIIb | 6y | 2l | — | 4c | 5b |
| IIIb | 6x | 2m | — | 4c | 5b |
| IIIb | 6d | 2h | — | 4c | 5v |
| IIIb | 6mm | 2l | — | 4a | 5a |
| IIIb | 6kk | 2m | — | 4b | 5b |
| IIIb | 6ll | 2h | — | 4c | 5w |
| IIIb | 6jj | 2l | — | 4b | 5c |
| IIIb | 6nn | 2m | — | 4c | 5v |
| IIIb | 6oo | 2l | — | 4c | 5b |
| IIIb | 6pp | 2l | — | 4b | 5b |
| IIIb | 6qq | 2m | — | 4c | 5w |
| IIIb | 6e | 2h | — | 4a | 5v |
| IIIb | 6u | 2l | — | 4b | 5a |
| IIIb | 6p | 2m | — | 4c | 5b |
| IIIb | 6c | 2l | — | 4c | 5b |
| IIIb | 6f | 2l | — | 4a | 5b |
| IIIb | 6g | 2m | — | 4b | 5v |
| IIIb | 6j | 2h | — | 4c | 5a |
| IIIb | 6t | 2l | — | 4c | 5b |
| IIIb | 6y | 2m | — | 4c | 5b |
| IIIb | 6x | 2h | — | 4a | 5c |
| IIIb | 6d | 2l | — | 4b | 5v |
| IIIb | 6mm | 2m | — | 4c | 5a |
| IIIb | 6kk | 2h | — | 4a | 5b |
| IIIb | 6ll | 2l | — | 4b | 5w |
| IIIb | 6jj | 2m | — | 4c | 5b |
| IIIb | 6nn | 2h | — | 4b | 5a |
| IIIb | 6oo | 2l | — | 4c | 5b |
| IIIb | 6pp | 2m | — | 4a | 5b |
| IIIb | 6qq | 2h | — | 4b | 5v |
| IIIb | 6e | 2l | — | 4c | 5a |
| IIIb | 6u | 2m | — | 4c | 5b |
| IIIb | 6p | 2h | — | 4a | 5w |
| IIIb | 6c | 2l | — | 4b | 5c |
| IIIb | 6f | 2m | — | 4c | 5b |
| IIIb | 6g | 2h | — | 4a | 5a |
| IIIb | 6j | 2l | — | 4b | 5b |

In particular embodiments of the compounds of formulae (III), (IIIa) and (IIIb), the compound can be of the formula (III*), (IIIa*) or (IIIb*):

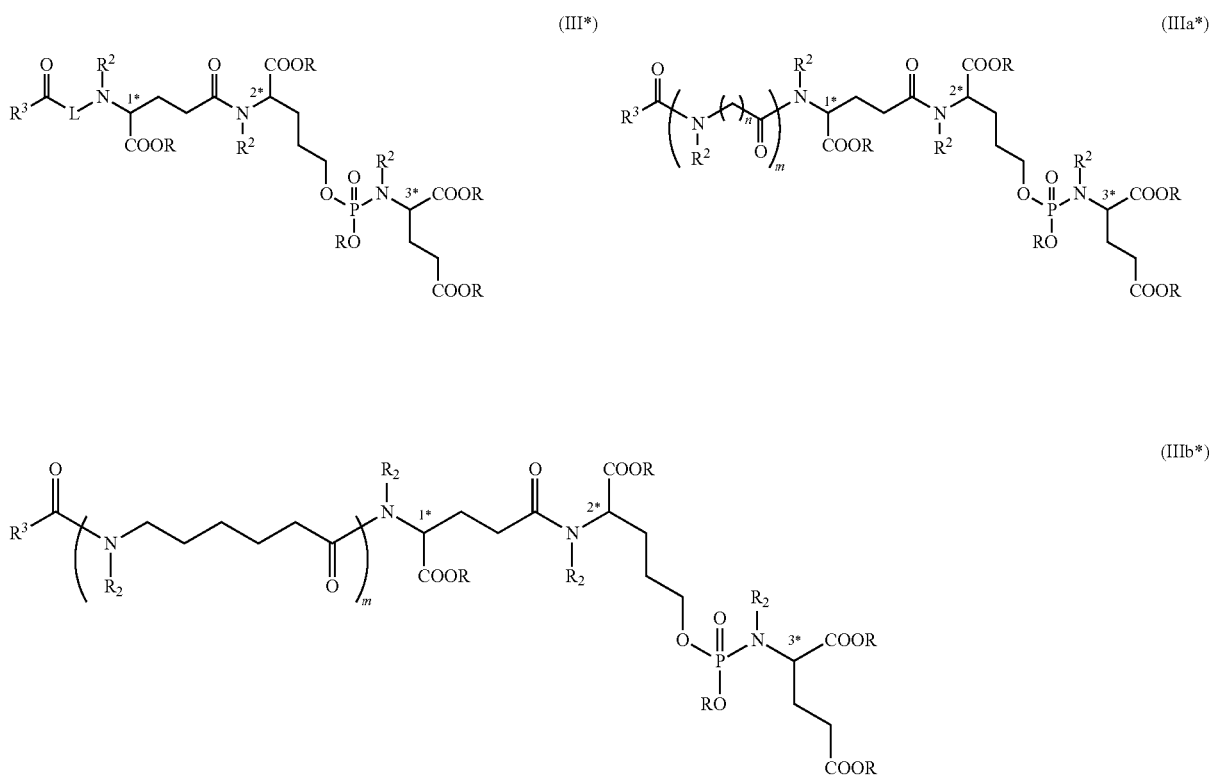

and a pharmaceutically acceptable salt thereof, wherein $R^3$, m, n, $R^2$, and R are as defined according to any one of the embodiments described above for formulae (III), (IIIa) and (IIIb), and the stereoconfiguration of 1*, 2*, and 3* are as defined above for compounds of formulae (I*), (Ia*) and (Ib*).

In an embodiment of any of the preceding embodiments of the compounds of formula (IIIa*), the compound can be of the formula (IIIc):

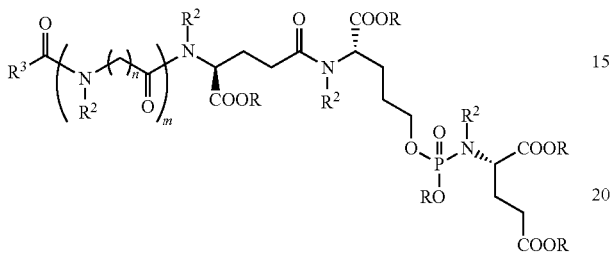

(IIIc)

and pharmaceutically acceptable salts thereof.

In an embodiment of any of the preceding embodiments of the compounds of formula (IIIb*), the compound can be of the formula (IIId):

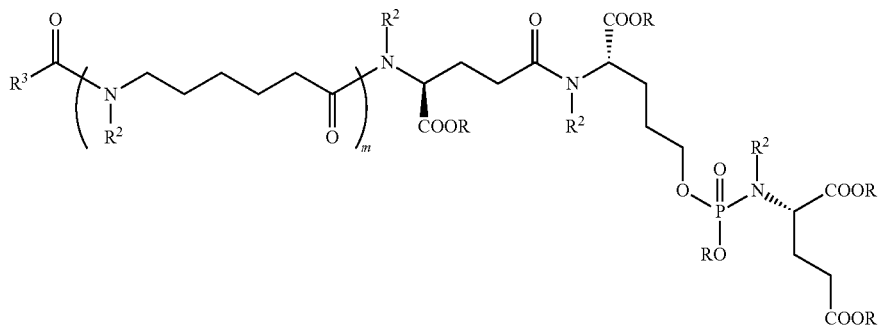

(IIId)

and pharmaceutically acceptable salts thereof.

In another embodiment, the compound of formula (III) is

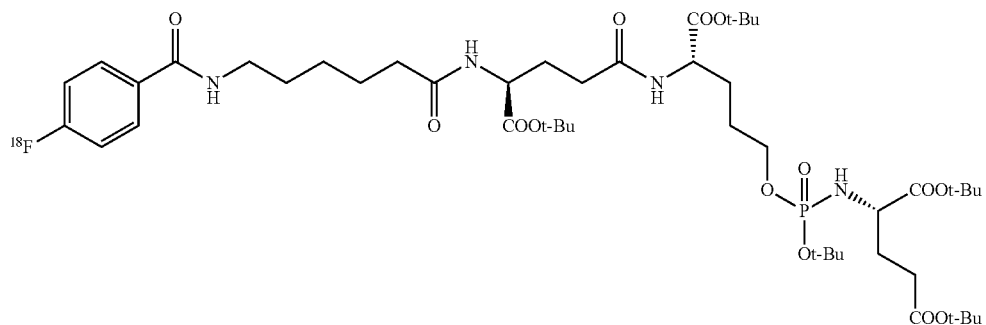

-continued
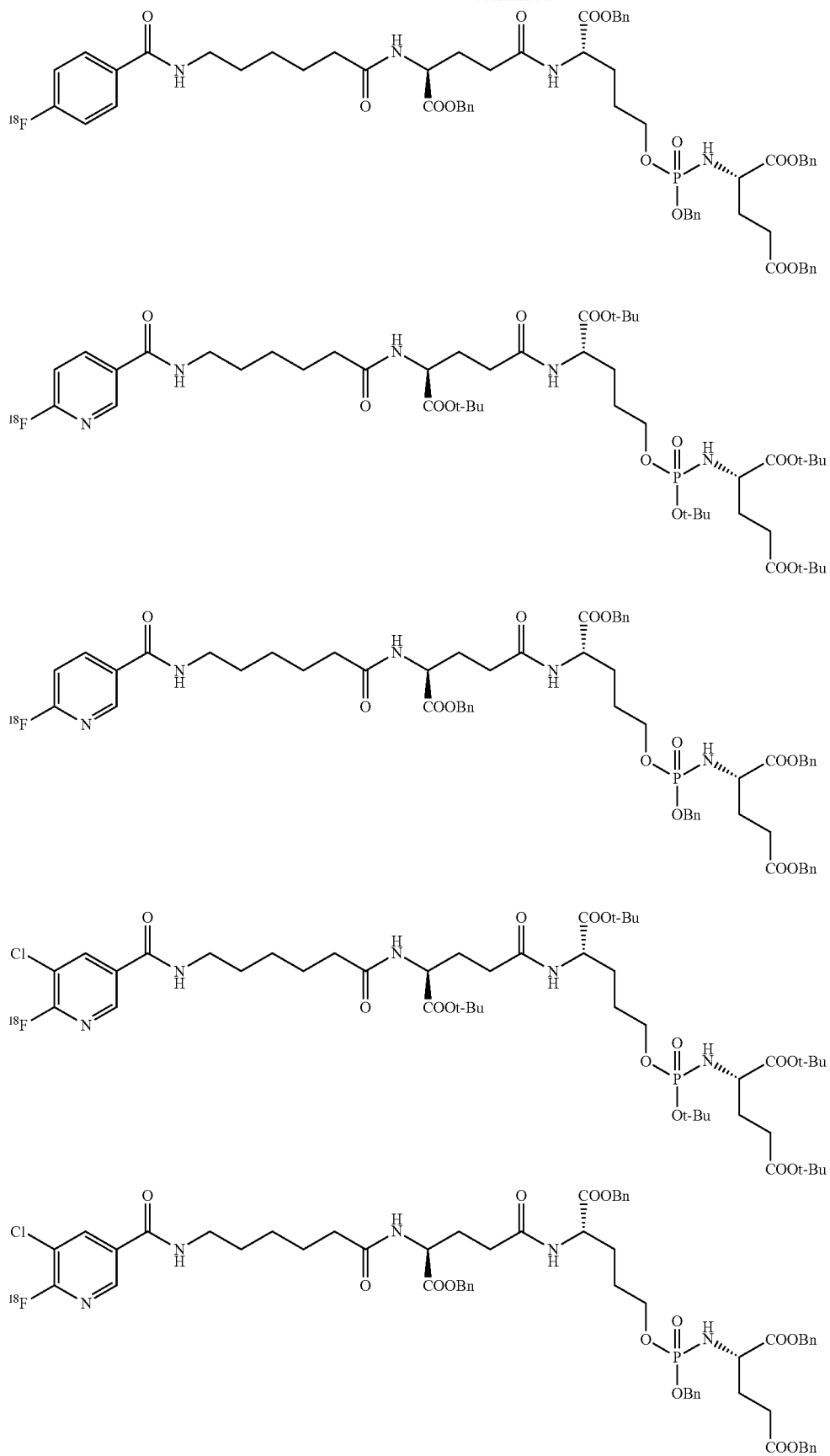

-continued
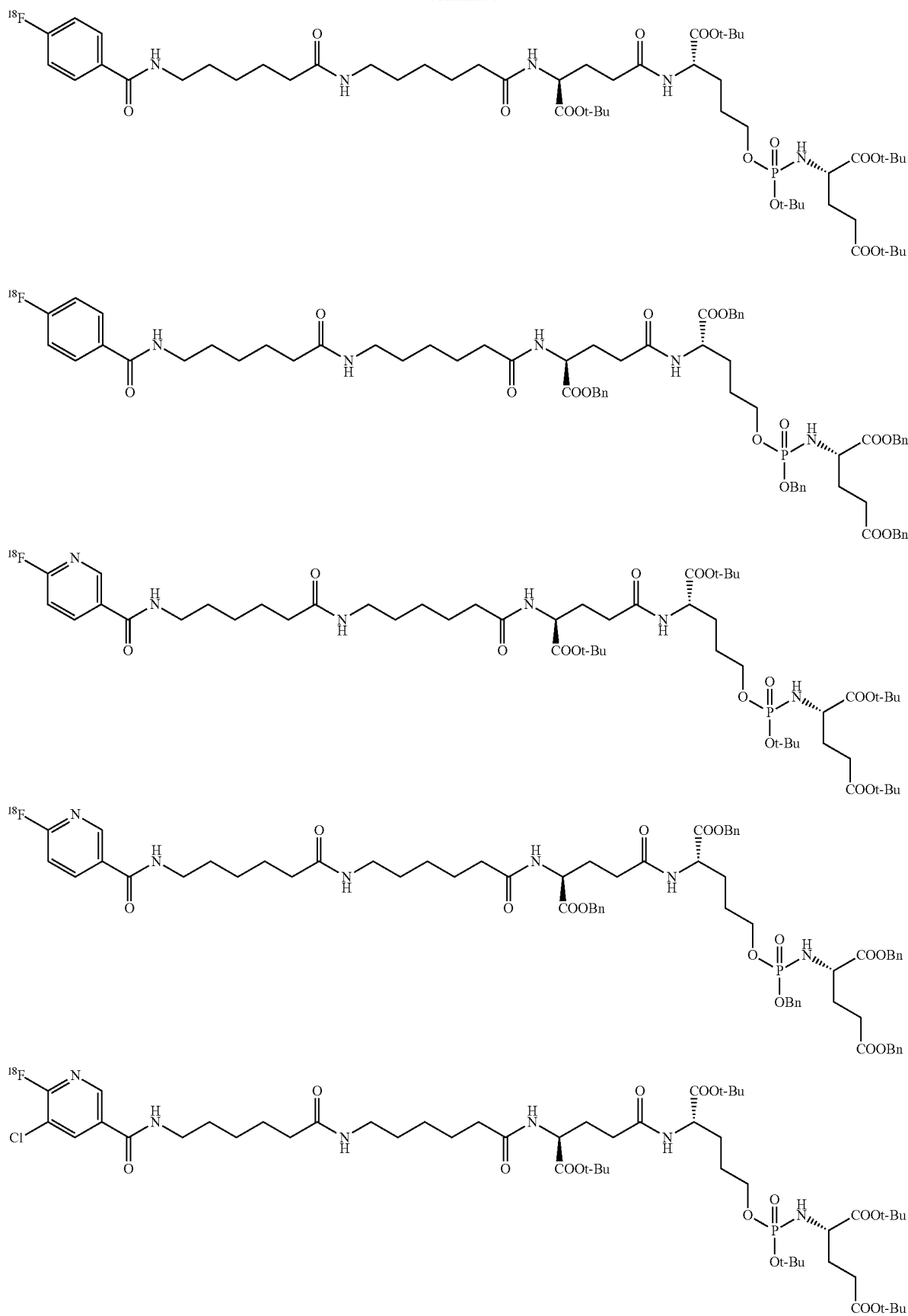

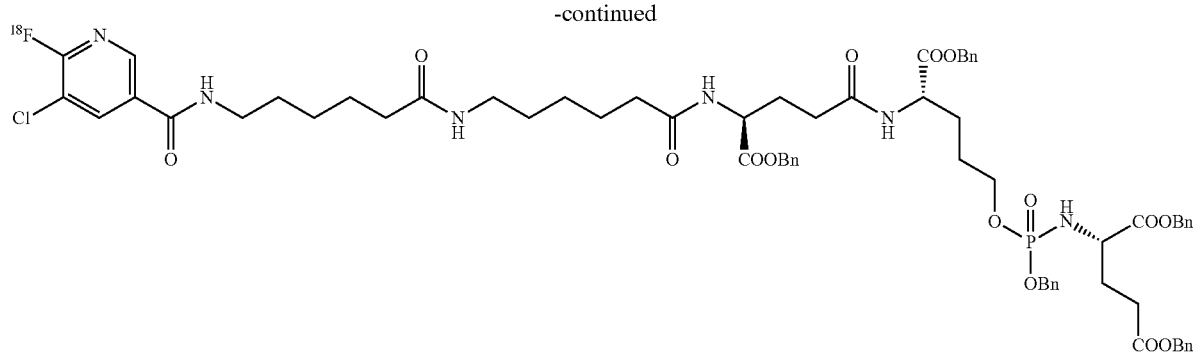
and other pharmaceutically acceptable salts thereof, such as, for example, sodium.
In another embodiment, the compound of formula (III) is
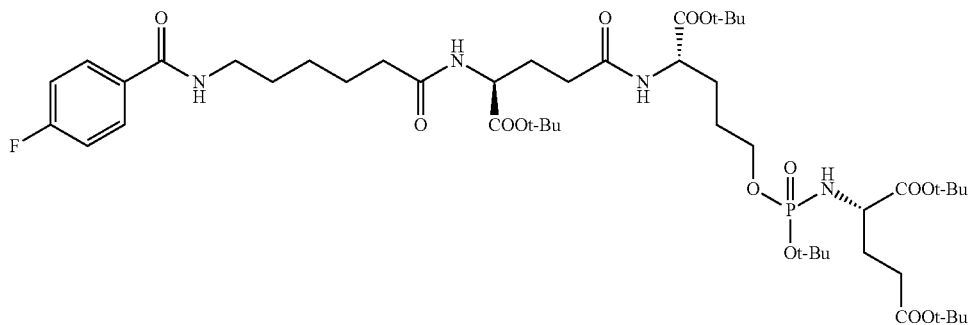
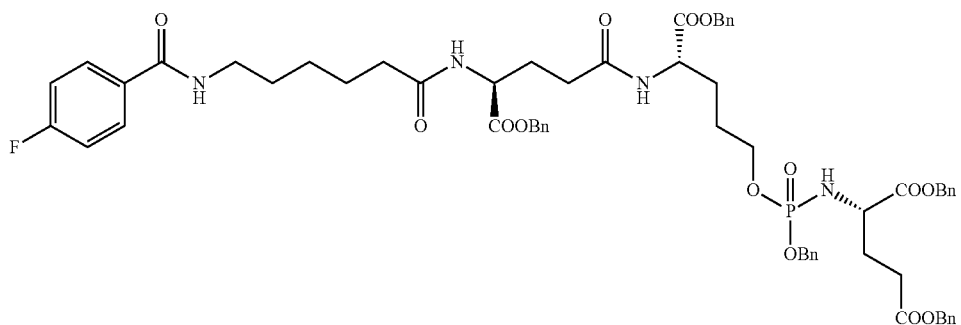
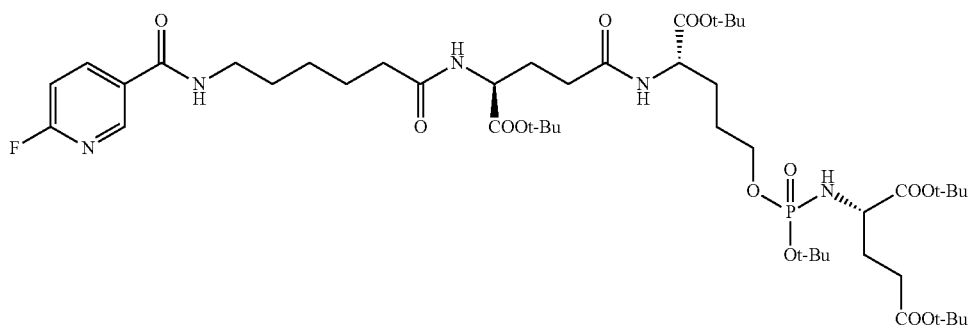

-continued
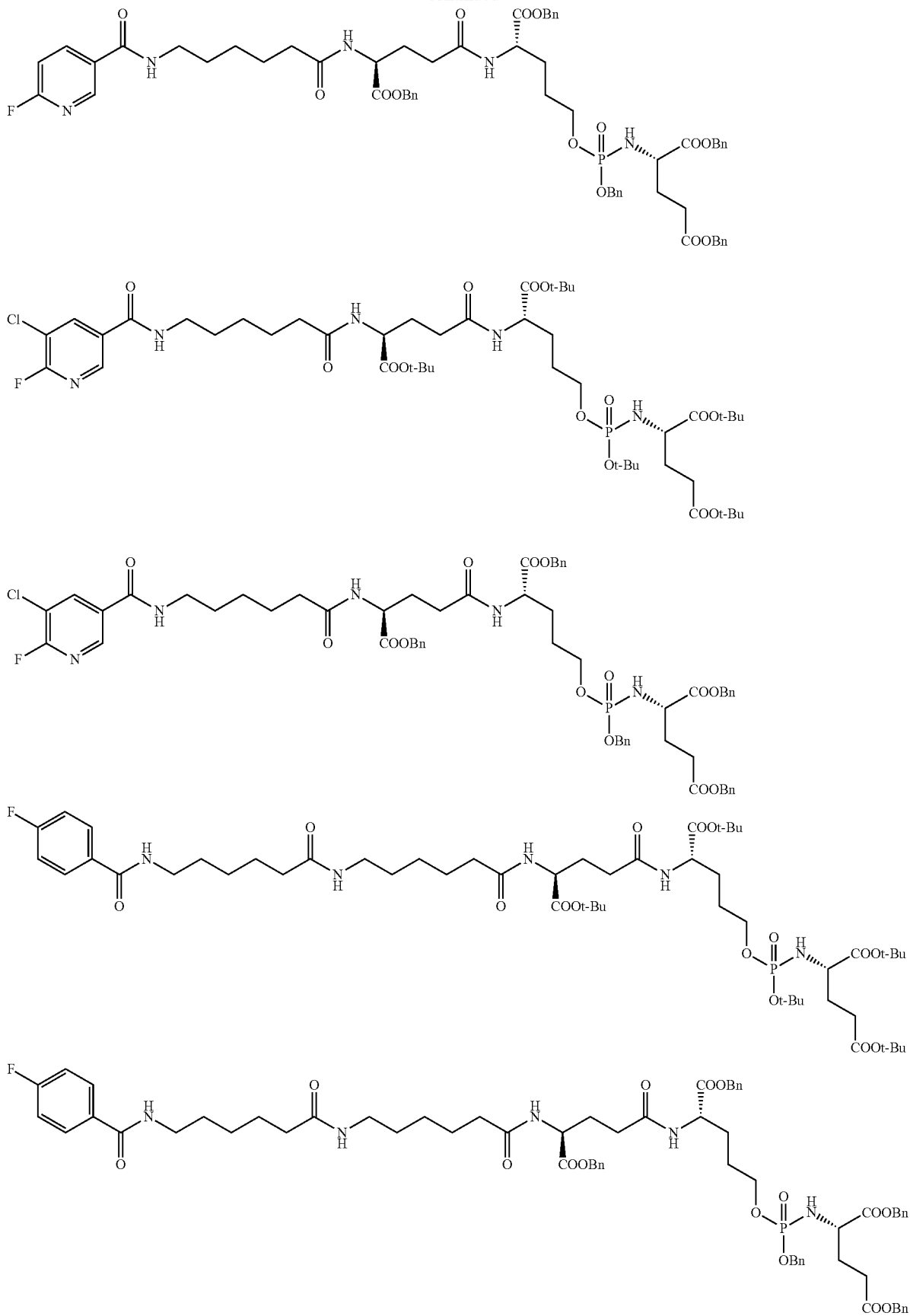

71
72
-continued
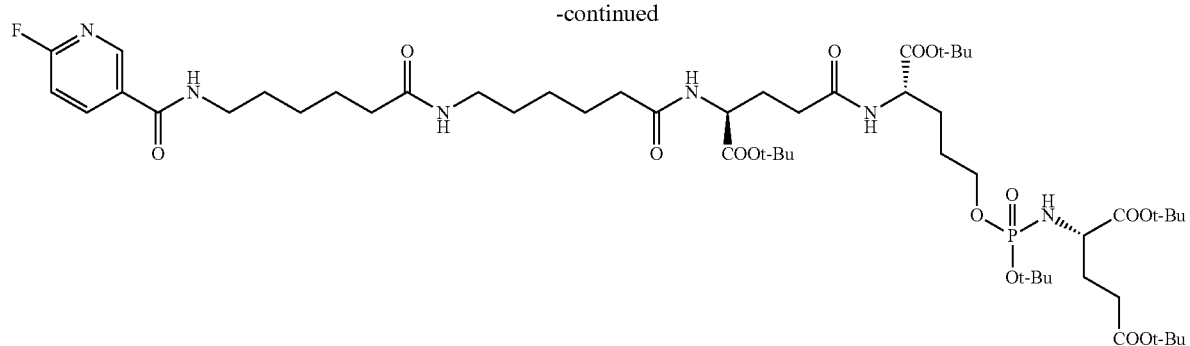
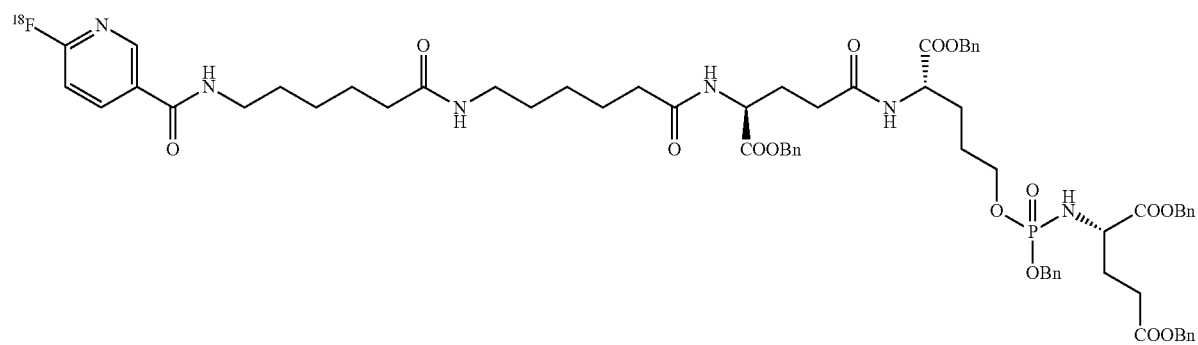
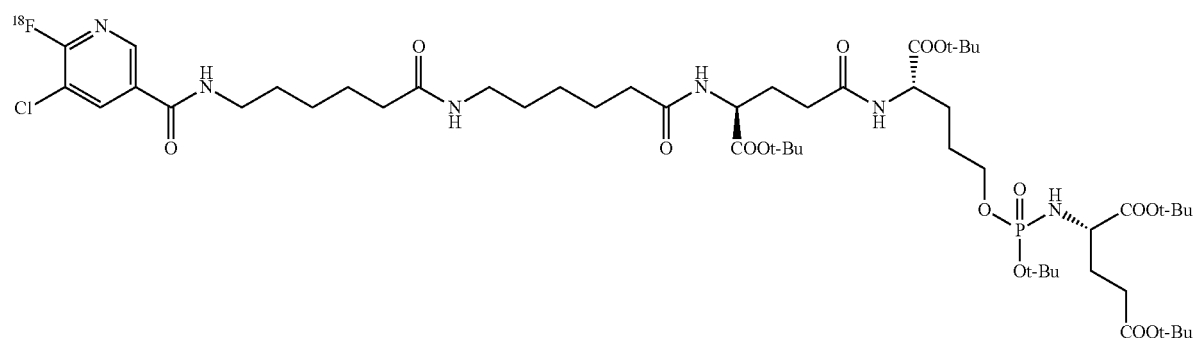
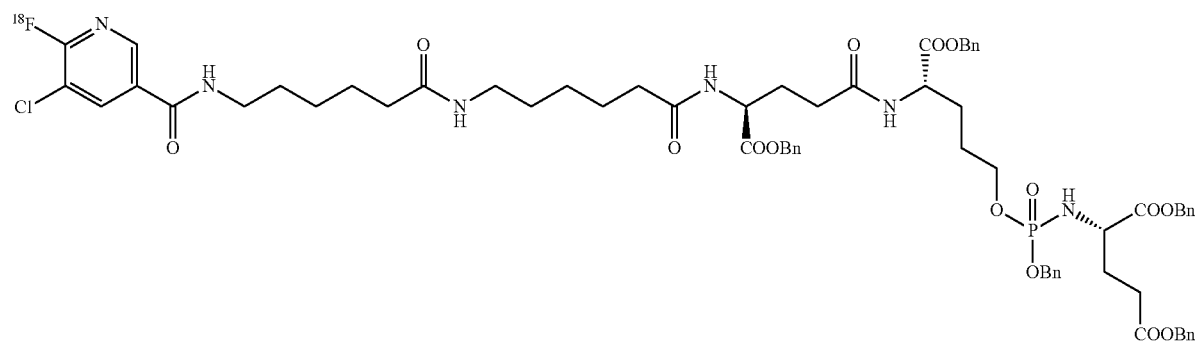

and other pharmaceutically acceptable salts thereof, such as, for example, sodium.

The compounds of formula (I) can be prepared by a method comprising:

contacting a compound of the formula (III):

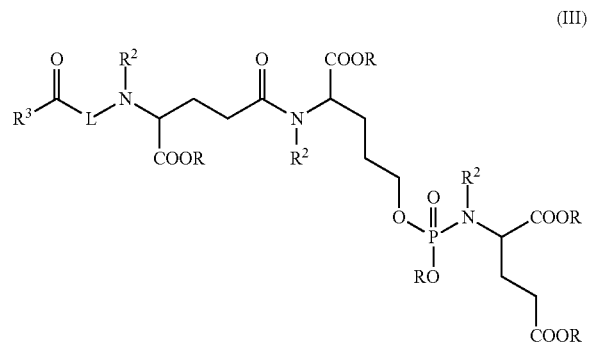

(III)

or a pharmaceutically acceptable salt thereof, wherein the definitions of L, $R^2$, and R are defined above for the compound of formula (I), and include compounds in which m is any one of (2a)-(2o), each n is independently any one of (3a)-(3x), each $R^2$ is independently any of (4a)-(4v), and each R is independently any one of (5a)-(5w), and $R^3$ is phenyl or pyridyl; wherein the phenyl or pyridyl is substituted with a leaving group and optionally substituted with a second group selected from halogen, cyano, and nitro, which includes compounds in which $R^3$ is any one of (6a)-(6ss); with a fluoride or radiofluoride source.

In one embodiment, the radiofluoride source is $Na^{18}F$, $K^{18}F$, $Cs^{18}F$, tetra($C_1$-$C_6$)alkylammonium$^{18}F$ fluoride, or tetra($C_1$-$C_6$)alkylphosphonium $^{18}F$ fluoride. In another embodiment, the fluoride source is NaF, KF, CsF, tetra($C_1$-$C_6$)alkylammonium fluoride, or tetra($C_1$-$C_6$)alkylphosphonium fluoride.

In other embodiments, a base may be used in combination with the fluoride or radiofluoride source. Suitable bases include, but are not limited to, potassium carbonate, potassium bicarbonate, potassium oxalate, potassium sulfonates, potassium tert-alkoxylates, cesium carbonate, cesium bicarbonate, tetrabutylammonium hydroxide (TBAOH), tetrabutylammonium bicarbonate ($TBAHCO_3$), and tetrabutylammonium mesylate (TBAOMs).

To increase the reactivity of the fluoride, a phase transfer catalyst such as an aminopolyether or crown ether, for example, 4,7,13,16,21,24 hexaoxa-1,10-diazabicyclo[8,8,8] hexacosane (Kryptofix 2.2.2; K222) may be added and the reaction performed in a non protic solvent.

The treatment with fluoride or radiofluoride anion can be effected in the presence of a suitable organic solvent such as acetonitrile, dimethylformamide, dimethylacetamide, dimethyl sulfoxide, tetrahydrofuran, dioxane, 1,2 dimethoxyethane, ethanol, methanol, iso-propanol, n-butanol, t-butanol, amyl alcohol, sulfolane, N-methylpyrrolidone, toluene, benzene, dichlorobenzenes, dichloromethane, xylenes, or mixtures thereof, at a non-extreme temperature, for example, 15° C. to 180° C., preferably at ambient to elevated temperatures, such as 20° C. to 150° C.; or 20° C. to 120° C.; or 20° C. to 100° C.; 20° C. to 70° C. The reaction solution can be heated using microwave irradiation for about 1 minute to about 1 hour; for example, about 5 to 15 minutes.

In one embodiment, the base used in combination with the fluoride or radiofluoride source is cesium carbonate or tetrabutylammonium bicarbonate. In one embodiment, the base used in combination with the fluoride or radiofluoride source is cesium carbonate. In one embodiment, the base used in combination with the fluoride or radiofluoride source is tetrabutylammonium bicarbonate.

In one embodiment, the base used in combination with the fluoride or radiofluoride source is cesium carbonate or tetrabutylammonium bicarbonate at a temperature between about 50 and 70° C. In one embodiment, the base used in combination with the fluoride or radiofluoride source is cesium carbonate at a temperature between about 50 and 70° C. In one embodiment, the base used in combination with the fluoride or radiofluoride source is tetrabutylammonium bicarbonate at a temperature between about 50 and 70° C.

In another embodiment, the base used in combination with the fluoride or radiofluoride source is tetrabutylammonium hydroxide. In another embodiment, the base used in combination with the fluoride or radiofluoride source is tetrabutylammonium hydroxide at a temperature between about 90° C. and 110° C. (e.g., 100° C.). In another embodiment, the base used in combination with the fluoride or radiofluoride source is tetrabutylammonium hydroxide at a temperature between about 90° C. and 110° C. (e.g., 100° C.), where the temperature is maintained for about 5 minutes to about 15 minutes (e.g., about 10 min.).

Following the reaction, excess fluoride or radiofluoride anion may optionally be removed from the solution of the fluoride-labeled or radiofluoride-labeled compound by any suitable means, for example by distillation, chromatography such as by silica gel and C-18 reversed phase chromatography, or alternatively by ion-exchange chromatography or solid phase absorbents, for example by anionic exchange resin or a quaternary alkylated amino resin.

An anionic exchange resin is a resin containing a cation group, typically amino groups that are protonated to give ammonium salt or quaternary alkylated amino groups, which attract and retain anions present in the solution surrounding the said resin.

A resin is organic polymer or functionalized silica that is insoluble in most organic solvents, aqueous solutions and mixtures thereof.

A quaternary alkylated amino resin is a resin that it functionalized with one or more amino groups and these amino groups are substituted independently with three alkyl or alkylaryl groups or mixture thereof to give an ammonium salt ($N+R^1R^2R^3R^4$) where are R1 is the resin. R2, $R^3$ and $R^4$ can be methyl, ethyl, propyl, butyl, benzyl, ethylphenyl For example, a resin or solid, that allows trapping of $^{18}F$ fluoride may be used, such as a QMA or PS-30 cartridge. In other examples, chromatography over SepPak™ cartridges (Waters Corp., Milford, Mass.; e.g., $C_{18}$ Silica, Florisil™, or Alumina A, B, N chemistries) may be used as are familiar to those skilled in the art. Suitable ion-exchange resins include BIO-RAD AG 1-X8 or Waters QMA and suitable solid phase absorbents include alumina.

In some embodiments, a compound of formula (Ia):

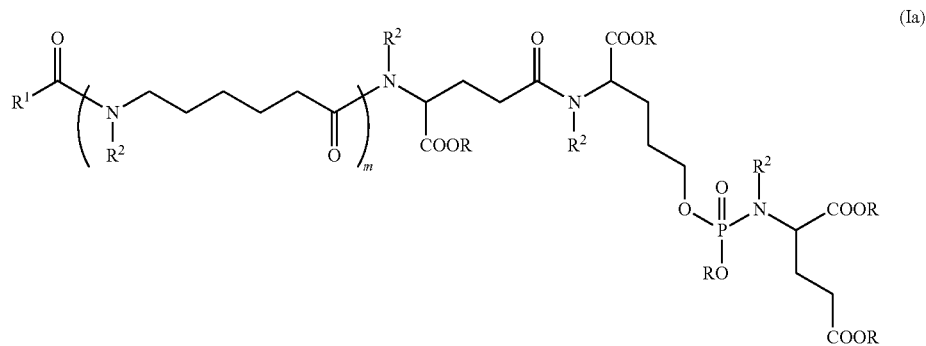

(Ia)

or a pharmaceutically acceptable salt thereof, can be prepared by a method comprising:
contacting a compound of the formula (IIIa):

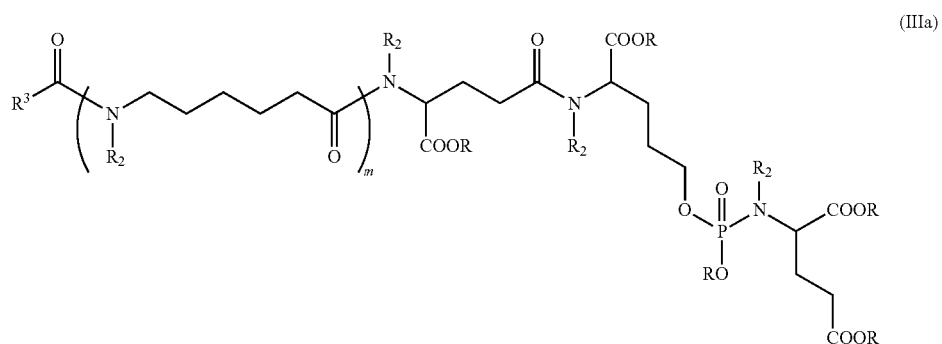

(IIIa)

or a pharmaceutically acceptable salt thereof, with a fluoride or radiofluoride source as described herein.

In some embodiments, a compound of formula (Ib):

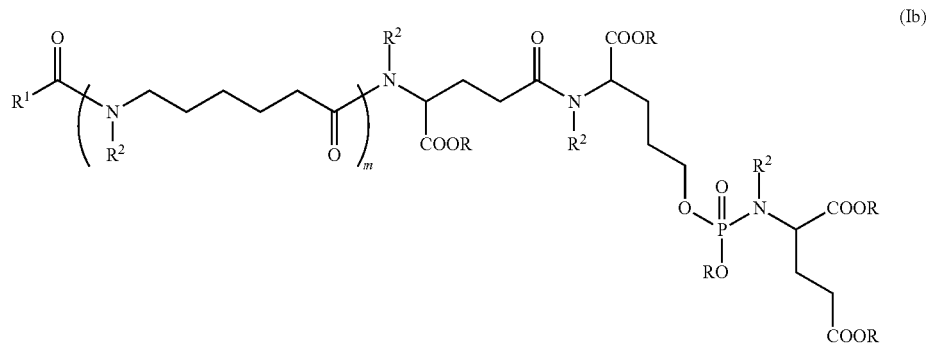

(Ib)

or a pharmaceutically acceptable salt thereof, can be prepared by a method comprising:

contacting a compound of the formula (IIIb):

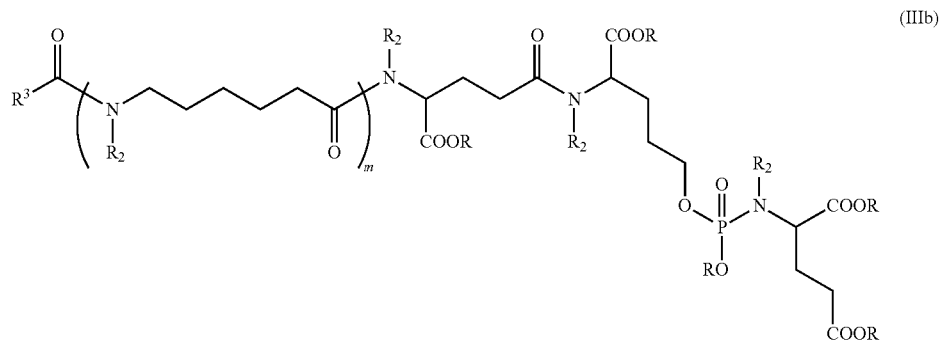

(IIIb)

or a pharmaceutically acceptable salt thereof, with a fluoride or radiofluoride source as described herein.

In some embodiments, the method is used to prepare compounds of formula (Ib) wherein m is 1, and each R and $R^2$ are hydrogen, the method comprising: contacting a compound of formula (IIIb), wherein m is 1, and each R and $R^2$ are hydrogen, with a fluoride or radiofluoride source as described herein. In other embodiments, m is 2, and each R and $R^2$ are hydrogen.

In another aspect, the invention comprises compounds that are

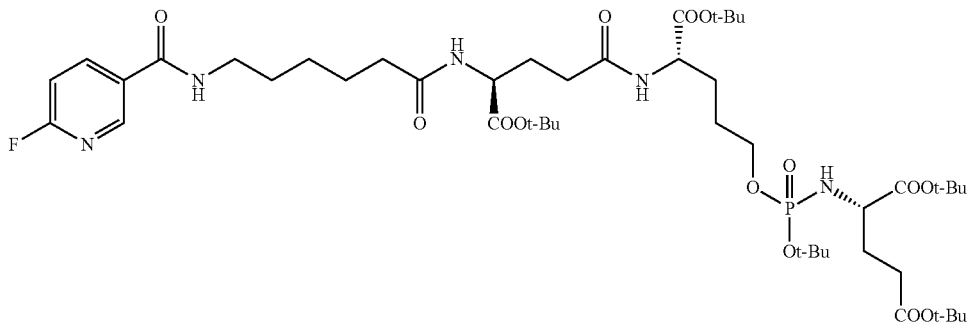

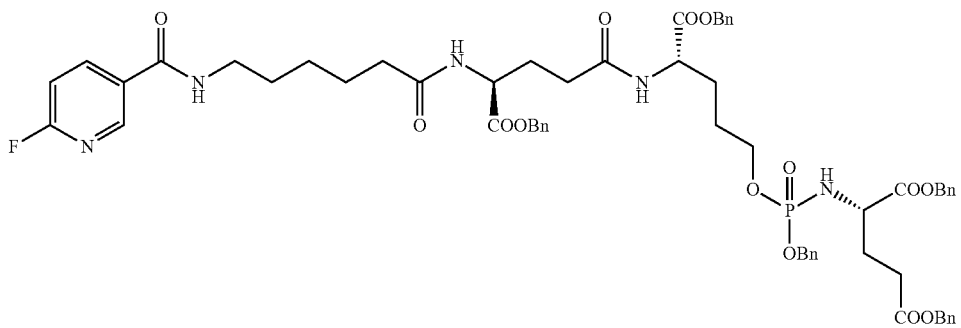

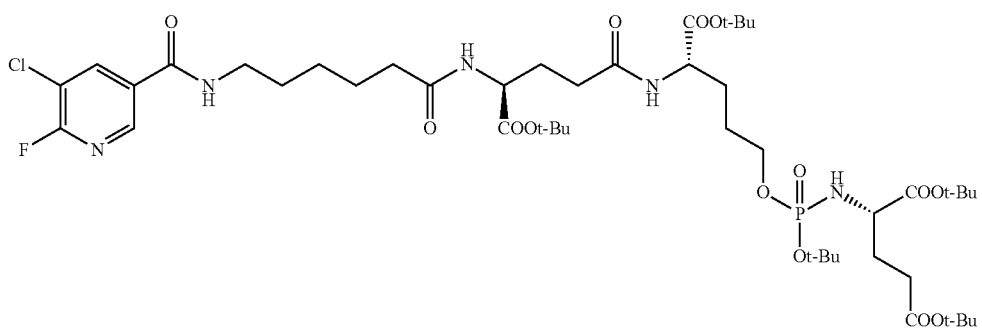

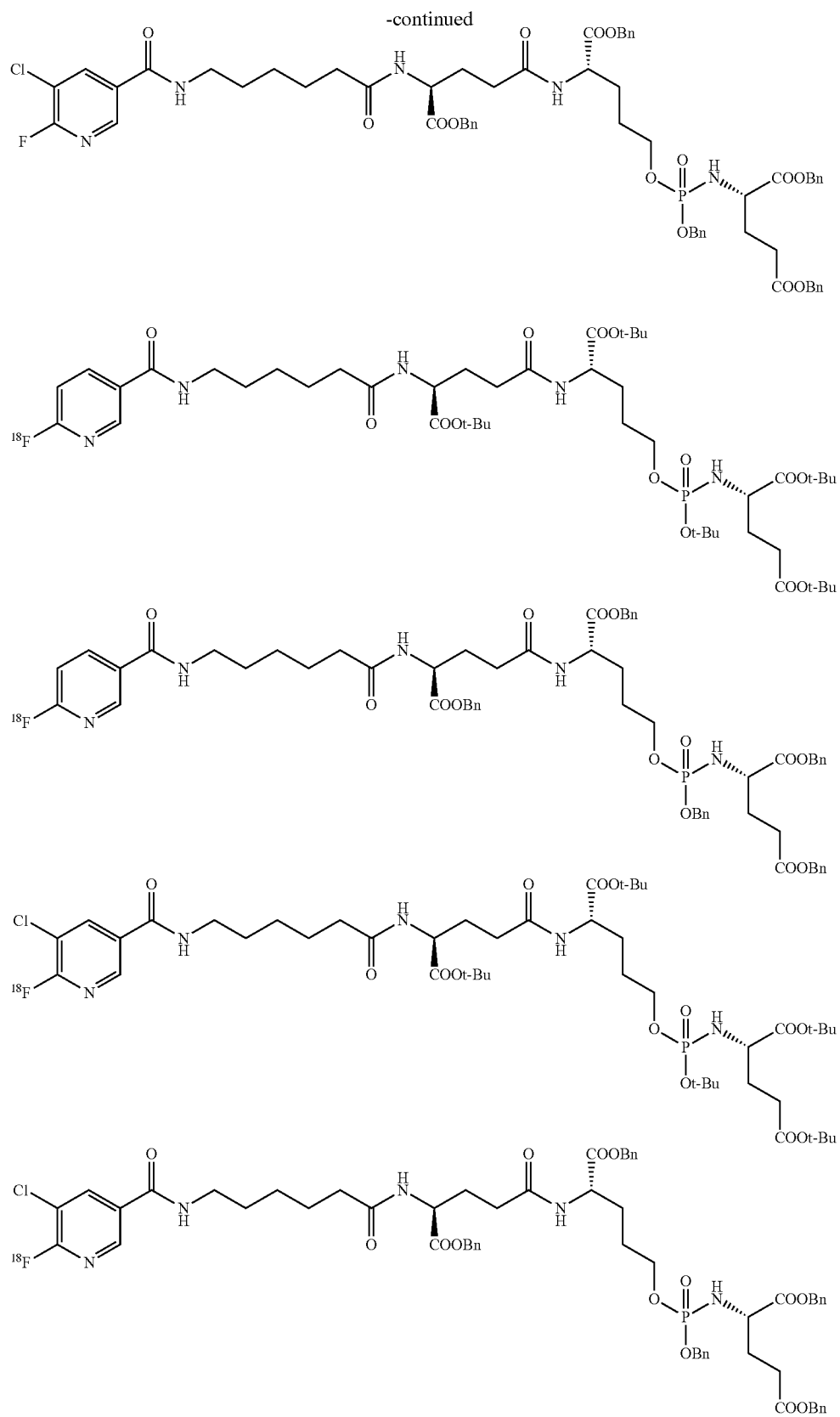
and other pharmaceutically acceptable salts thereof, such as, for example, sodium.
The compounds of formula (I) are prepared by a method comprising:

contacting a compound of the formula (II),

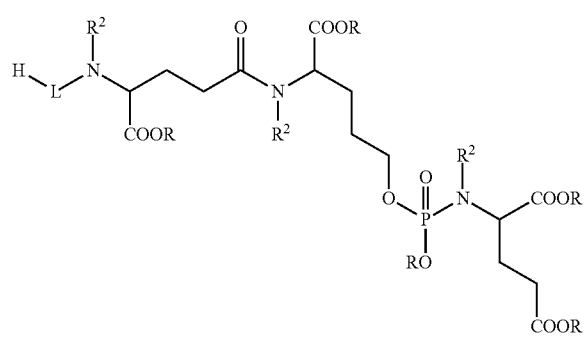

or a pharmaceutically acceptable salt thereof, wherein the definitions of L, R², and R are defined above for the compound of formula (I), and include compounds in which R² is any of (4a)-(4v), and R is any one of (5a)-(5w);

with a compound of formula (IV):

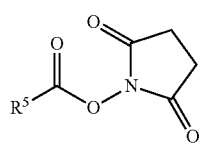

wherein R⁵ is R¹, wherein R¹ is phenyl or pyridyl; wherein the phenyl or pyridyl is substituted with an [F]- or [¹⁸F]-fluoro group and optionally substituted with a second group selected from halogen, cyano, and nitro, or anyone of groups (1a)-(1ii).

In some embodiments, the compounds of formula (Ia) are prepared by a method comprising:

contacting a compound of the formula (IIa),

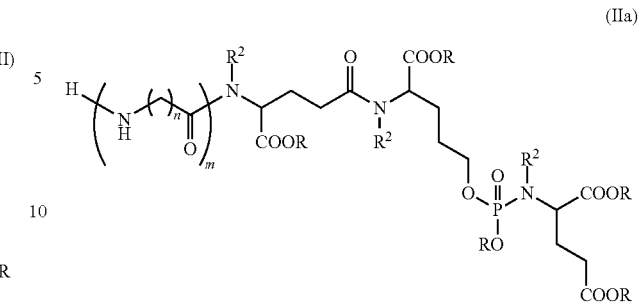

or a pharmaceutically acceptable salt thereof, wherein the definitions of n, m, R², and R are defined above for the compound of formula (I), and include compounds in which m is any one of (2a)-(2o), each n is independently any one of (3a)-(3x), each R² is independently any of (4a)-(4v), and each R is independently any one of (5a)-(5w);

with a compound of formula (IV).

In some embodiments, the compounds of formula (Ib) are prepared by a method comprising:

contacting a compound of the formula (IIb),

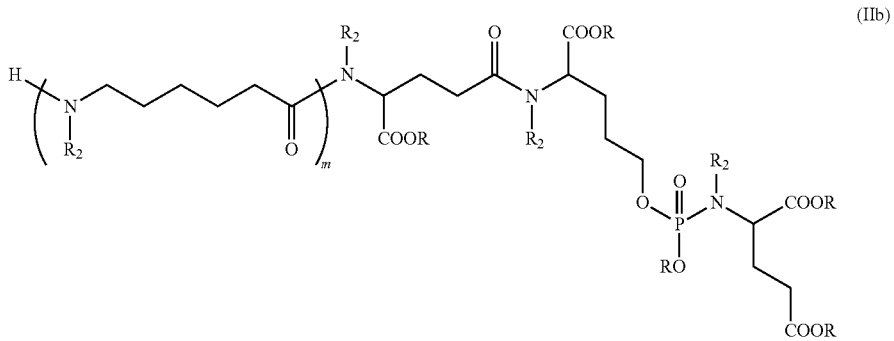

or a pharmaceutically acceptable salt thereof, wherein the definitions of m, R², and R are defined above for the compound of formula (I), and include compounds in which m is any one of (2a)-(2o), each R² is independently any of (4a)-(4v), and each R is independently any one of (5a)-(5w);

with a compound of formula (IV).

The compounds of formula (I), wherein at least one R is hydrogen, are prepared by a method comprising:

deprotecting a compound of the formula (I),

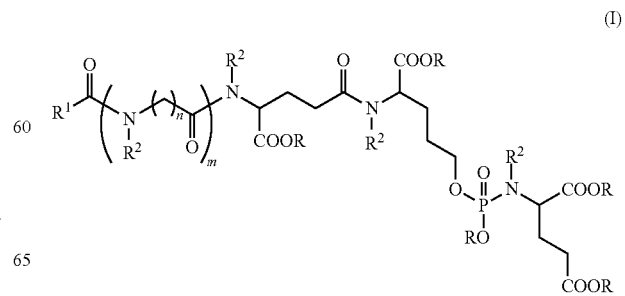

or a pharmaceutically acceptable salt thereof, wherein
the definitions of $R^1$, m, n, $R^2$, and R are defined above for the compound of formula (I), and include compounds in which $R^1$ is any one of (1a)-(1kk), m is any one of (2a)-(2o), each n is independently any one of (3a)-(3x), each $R^2$ is independently any of (4a)-(4v), and each R is independently any one of (5a)-(5w), wherein at least one R is a protecting group
under conditions suitable for removing at least one of the protecting groups.

As would be clear to one skilled in the art, removal of the protecting groups in the preceding results in the formation of the corresponding compound wherein R is hydrogen, or a salt thereof (e.g., a compound of formula (I) where at least one R is hydrogen).

When R is a t-butyl group, the method can be maintained under anhydrous conditions to prevent degradation of the compounds, as the phosphoramidate moiety is known to be unstable in aqueous acidic media. In various embodiment, each of the following deprotection conditions can be utilized for removal of t-butyl groups:

i) Contacting the compound with an acid selected from the groups consisting of, trifluoroacetic acid, hydrochloric acid, formic acid, glacial acetic acid, chloroacetic acid, and mixtures thereof;
ii) Contacting the compound with an acid (selected as in (i)) in a solvent selected from the group consisting of diethyl ether, ethyl acetate, dioxane, 1,2-dichloroethane, dichloromethane, t-butanol, glyme, methyl t-butylether, tetrahydrofuran, and mixtures thereof;
iii) Contacting the compound with a neat acid;
iv) Contacting the compound any of the preceding with the addition of scavengers, such as, but not limited to triethylsilane (TES);
v) Contacting the compound as in any of the preceding at a temperatures between room temperature (e.g., 25° C.) and 180° C.;
vi) Contacting the compound as in any of the preceding with microwave heating;
vii) Contacting the compound with a base such as, but not limited to, NaOH;
viii) Contacting the compound as in any of the preceding, where the reaction is allowed to proceed for a period of time between about 15 seconds and 15 minutes;
ix) Contacting the compound with trimethylsilyl iodide (TMS-I, may be formed in situ from trimethylsilyl chloride and sodium iodide),
x) Contacting the compound with trimethylsilyl triflate (TMSOTf) and triethylamine (TEA);
xi) Contacting the compound with quinoline at elevated temperatures, e.g., greater than 150° C., such as, 180° C.; or
xii) Contacting the compound with LiI in ethyl acetate.

In certain embodiments, the conditions include contacting the compound with formic acid. In certain other embodiments, the conditions include contacting the compound with neat formic acid.

In certain embodiments, the conditions include contacting the compound with formic acid at a temperature between about room temperature (e.g., 25° C.) and 100° C. In certain embodiments, the conditions include contacting the compound with formic acid at a temperature between about room temperature (e.g., 25° C.) and 75° C. In certain embodiments, the conditions include contacting the compound with formic acid at a temperature between about 35° C. and 75° C. In certain embodiments, the conditions include contacting the compound with formic acid at a temperature between about 40° C. and 60° C. In certain embodiments, the conditions include contacting the compound with formic acid at a temperature between about 45° C. and 55° C.

In certain embodiments, the conditions include contacting the compound with neat formic acid at a temperature between about room temperature (e.g., 25° C.) and 100° C. In certain embodiments, the conditions include contacting the compound with neat formic acid at a temperature between about room temperature (e.g., 25° C.) and 75° C. In certain embodiments, the conditions include contacting the compound with neat formic acid at a temperature between about 35° C. and 75° C. In certain embodiments, the conditions include contacting the compound with neat formic acid at a temperature between about 40° C. and 60° C. In certain embodiments, the conditions include contacting the compound with neat formic acid at a temperature between about 45° C. and 55° C.

In any of the preceding embodiments using formic acid or neat formic acid, the compound can be heated at a desired temperature (e.g., between about 45° C. and 55° C.) for a period of time between about 15 seconds and 15 minutes. In certain embodiment, the heating is for between about 15 seconds and 10 minutes; or 15 seconds and 8 minutes; or 1 minute and 8 minutes; or 2 minutes and 8 minutes; or 3 minutes and 8 minutes; or 4 minutes and 6 minutes; or about 5 minutes. Following the termination of the desired time period for heating the compound, any solvents and/or acids can be removed from the reaction mixture by methods familiar to those skilled in the art, such as in vacuo removal or by purging the reaction mixture with an inert gas, such as Ar, He, or $N_2$.

In certain embodiments, the conditions include contacting the compound with trifluoroacetic acid. In certain other embodiments, the conditions include contacting the compound with trifluoroacetic acid in a solvent. In certain embodiments, the solvent is 1,2-dichloroethane.

In certain embodiments, the conditions include contacting the compound with trifluoroacetic acid and a scavenger, such as triethylsilane. In certain other embodiments, the conditions include contacting the compound with trifluoroacetic acid and triethylsilane in a solvent. In certain embodiments, the solvent is 1,2-dichloroethane.

In certain embodiments, the conditions include contacting the compound with trifluoroacetic acid and triethylsilane in 1,2-dichloroethane at a temperature between about room temperature (e.g., 25° C.) and 150° C. In certain embodiments, the conditions include contacting the compound with trifluoroacetic acid and triethylsilane in 1,2-dichloroethane at a temperature between about 50° C. and 150° C. In certain embodiments, the conditions include contacting the compound with trifluoroacetic acid and triethylsilane in 1,2-dichloroethane at a temperature between about 75° C. and 125° C. In certain embodiments, the conditions include contacting the compound with trifluoroacetic acid and triethylsilane in 1,2-dichloroethane at a temperature between about 90° C. and 110° C.

In any of the preceding embodiments using trifluoroacetic acid and optionally triethylsilane, the compound can be heated at a desired temperature (e.g., between about 90° C. and 10° C.) for a period of time between about 15 seconds and 15 minutes. In certain embodiment, the heating is for between about 1 minute and 15 minutes; or about 1 minute and 12 minutes; or 5 minute and 15 minutes; or 5 minutes and 12 minutes; or 7 minutes and 12 minutes; or 9 minutes and 11 minutes; or about 10 minutes. Following the termination of the desired time period for heating the compound, any solvents and/or acids can be removed from the reaction mixture by methods familiar to those skilled in the art, such as in vacuo removal or by purging the reaction mixture with an inert gas, such as Ar or $N_2$.

In certain embodiments, each R is an optionally substituted benzyl group. In certain other embodiments, each R is a benzyl group. In other embodiments, each R is a substituted benzyl group.

When R is an optionally substituted benzyl group (e.g., unsubstituted benzyl), suitable deprotection conditions include, but are not limited to, hydrogenolysis conditions (e.g., $H_2$ and Pd/C) or catalytic hydrogen transfer using ammonium formate and Pd/C. Other hydrogenation catalysts may be used as are familiar to those skilled in the art.

In certain embodiments, alternative hydrogen sources may be used including, but not limited to ammonium formate, sodium formate, or formic acid with triethylamine. In certain embodiments, the hydrogen source is ammonium formate.

The hydrogenation may be undertake in a suitable solvent, selected from, but not limited to, ethanol, tetrahydrofuran, water, or phosphate buffered saline, or a mixture thereof.

For example, in certain embodiments, the deprotection can be setup in a cartridge where the Pd/C catalyst is loaded in a layer or distributed in inert material, then, the halogenated or radiolabeled sample (e.g., containing —F or —$^{18}$F) dissolved in a solvent (such as ethanol), is further dissolved in ammonium formate and flushed through the cartridge to yield deprotected material without the need for further purification.

In any of the preceding embodiments using Pd/C as a catalyst for deprotection, 5-10 wt % Pd/C can be used. In certain embodiments, 10 wt % Pd/C is used. About 0.01 to about 0.40 molar equivalents of Pd/C to the compound being deprotected can be used. In certain embodiments, about 0.01 to about 0.30 molar equivalents are used. In other embodiments, about 0.01 to about 0.20 molar equivalents; or 0.01 to about 0.10 molar equivalents; about 0.05 to about 0.40 molar equivalents; or about 0.05 to about 0.30 molar equivalents; or about 0.05 to about 0.20 0.01 to about 0.2 molar equivalents; or about 0.05 to about 0.10 molar equivalents; or about 0.075 to about 0.40 molar equivalents; or about 0.075 to about 0.30; or about 0.075 to about 0.20 molar equivalents; or about 0.075 to about 0.10 molar equivalents are used.

Further, in any of the preceding embodiments using Pd/C as a catalyst for deprotection, less than about 20% of the $^{18}$F label is removed from the compound during the deprotection step. That is, in going removing the benzyl groups, the yield of the reaction step is greater than about 80%.

In other embodiments, less than about 10% of the $^{18}$F label is removed from the compound during the deprotection step (greater than about 90% yield). In other embodiments, less than about 5% of the $^{18}$F label is removed from the compound during the deprotection step (greater than about 95% yield). In other embodiments, less than about 3% of the $^{18}$F label is removed from the compound during the deprotection step (greater than about 97% yield). In other embodiments, less than about 2% of the $^{18}$F label is removed from the compound during the deprotection step (greater than about 98% yield). In other embodiments, less than about 1% of the $^{18}$F label is removed from the compound during the deprotection step (greater than about 99% yield). In other embodiments, essentially none of the $^{18}$F label is removed from the compound during the deprotection step (essentially quantitative yield).

In other embodiments, the deprotection can be completed in less than about 30 minutes. For example, the deprotection step can be completed in less than about 20 minutes, or about 15 minutes, or about 10 minutes. In yet other embodiments, the deprotection can be completed in between about 1 minute and about 30 minutes; or about 1 minute and about 20 minutes; or about 1 minute and about 15 minutes; or about 1 minute and about 10 minutes; or about 5 minutes and about 30 minutes; or about 5 minutes and about 20 minutes; or about 5 minutes and about 15 minutes; or about 5 minutes and about 10 minutes.

In some embodiments, a compound of formula (Ia):

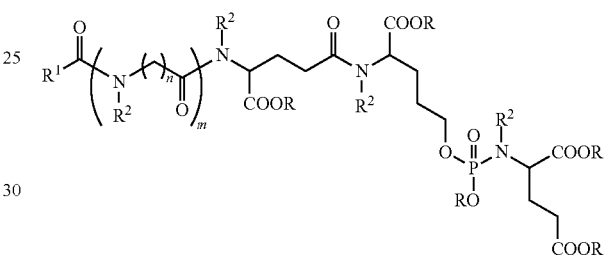

(Ia)

or a pharmaceutically acceptable salt thereof, wherein the definitions of $R^1$, m, n, $R^2$, and R are defined above for the compound of formula (I), and include compounds in which $R^1$ is any one of (1a)-(1kk), m is any one of (2a)-(2o), each n is independently any one of (3a)-(3x), each $R^2$ is independently any of (4a)-(4v), and each R is independently any one of (5a)-(5w), wherein at least one R is hydrogen, is prepared by a method comprising:

deprotecting a compound of the formula (Ia),
or a pharmaceutically acceptable salt thereof, wherein the definitions of $R^1$, m, n, $R^2$, and R are defined above for the compound of formula (I), and include compounds in which $R^1$ is any one of (1a)-(1kk), m is any one of (2a)-(2o), each n is independently any one of (3a)-(3x), each $R^2$ is independently any of (4a)-(4v), and each R is independently any one of (5a)-(5w), wherein at least one R is a protecting group;

under conditions suitable for removing at least one of the protecting groups.

In some embodiments, a compound of formula (Ib):

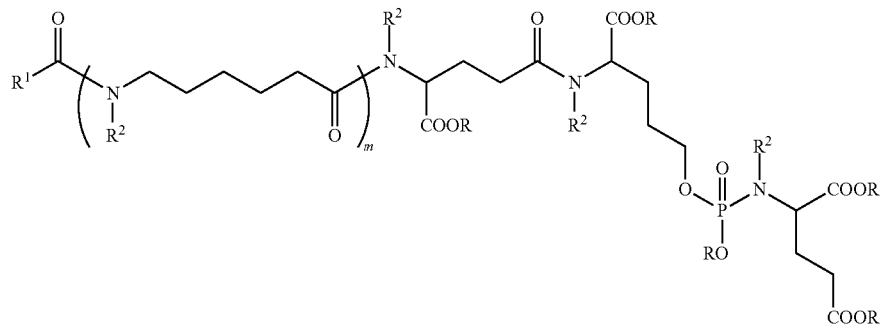

(Ib)

or a pharmaceutically acceptable salt thereof, wherein the definitions of $R^1$, m, $R^2$, and R are defined above for the compound of formula (I), and include compounds in which $R^1$ is any one of (1a)-(1kk), m is any one of (2a)-(2o), each $R^2$ is independently any of (4a)-(4v), and each R is independently any one of (5a)-(5w), wherein at least one R is hydrogen, is prepared by a method comprising:

deprotecting a compound of the formula (Ib), or a pharmaceutically acceptable salt thereof, wherein the definitions of $R^1$, m, $R^2$, and R are defined above for the compound of formula (I), and include compounds in which $R^1$ is any one of (1a)-(1kk), m is any one of (2a)-(2o), each $R^2$ is independently any of (4a)-(4v), and each R is independently any one of (5a)-(5w), wherein at least one R is a protecting group;

under conditions suitable for removing at least one of the protecting groups.

In some embodiments, the method is used to prepare compounds of formula (Ib) wherein m is 1, and each R and $R^2$ are hydrogen. In other embodiments, m is 2, and each R and $R^2$ are hydrogen.

In particular embodiments, the compound is

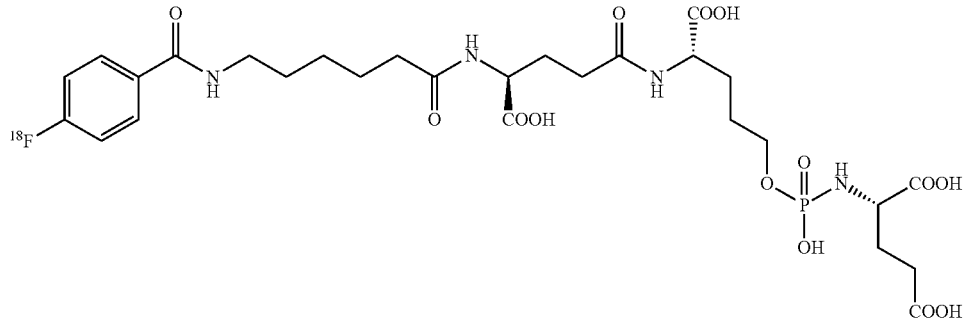

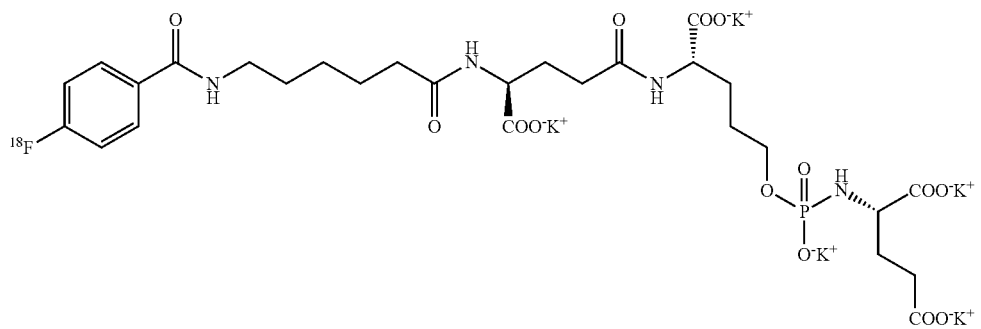

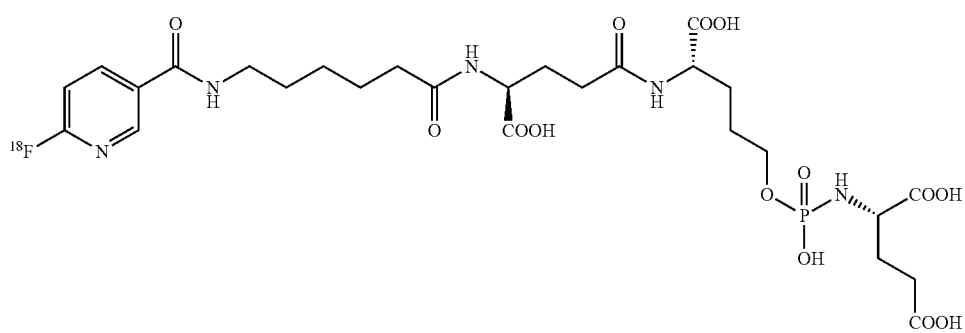

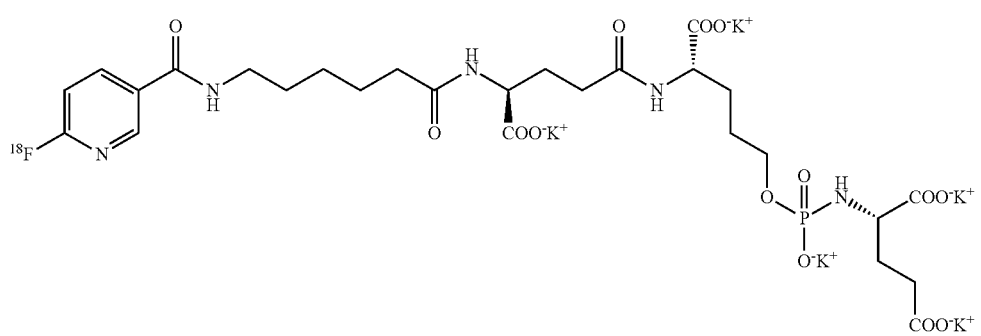

-continued
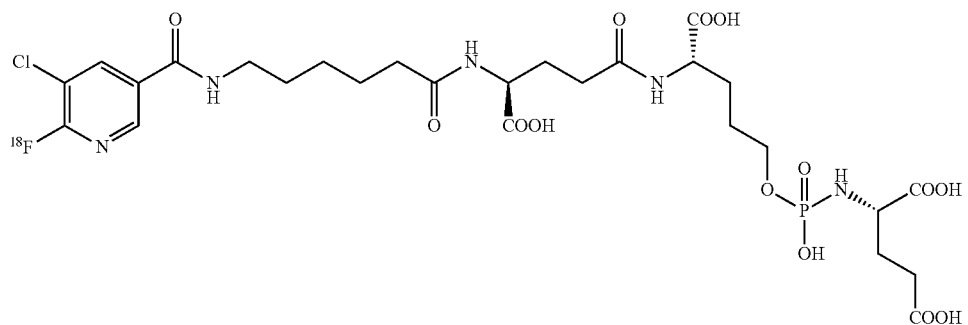
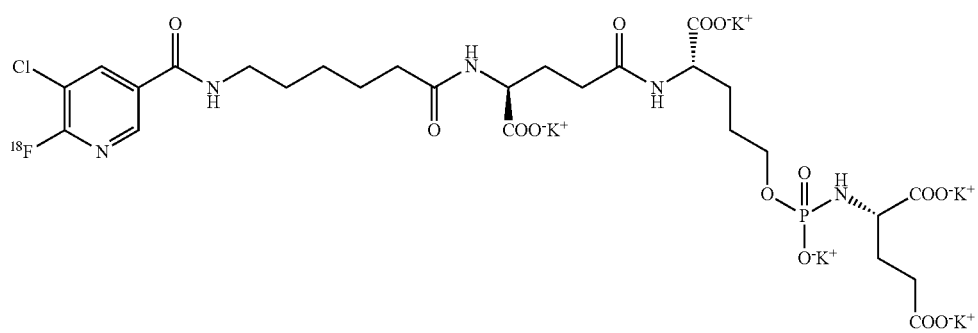
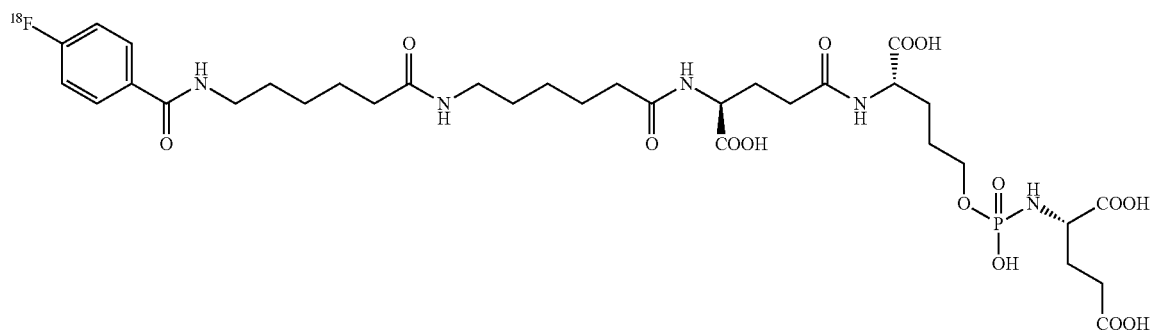
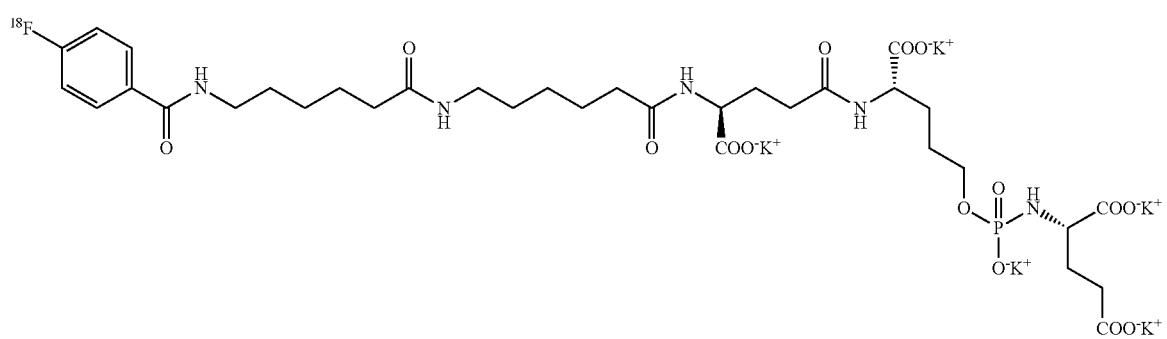
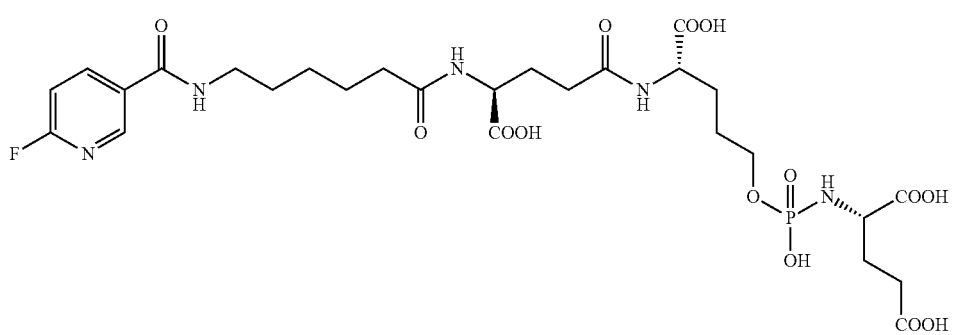

-continued
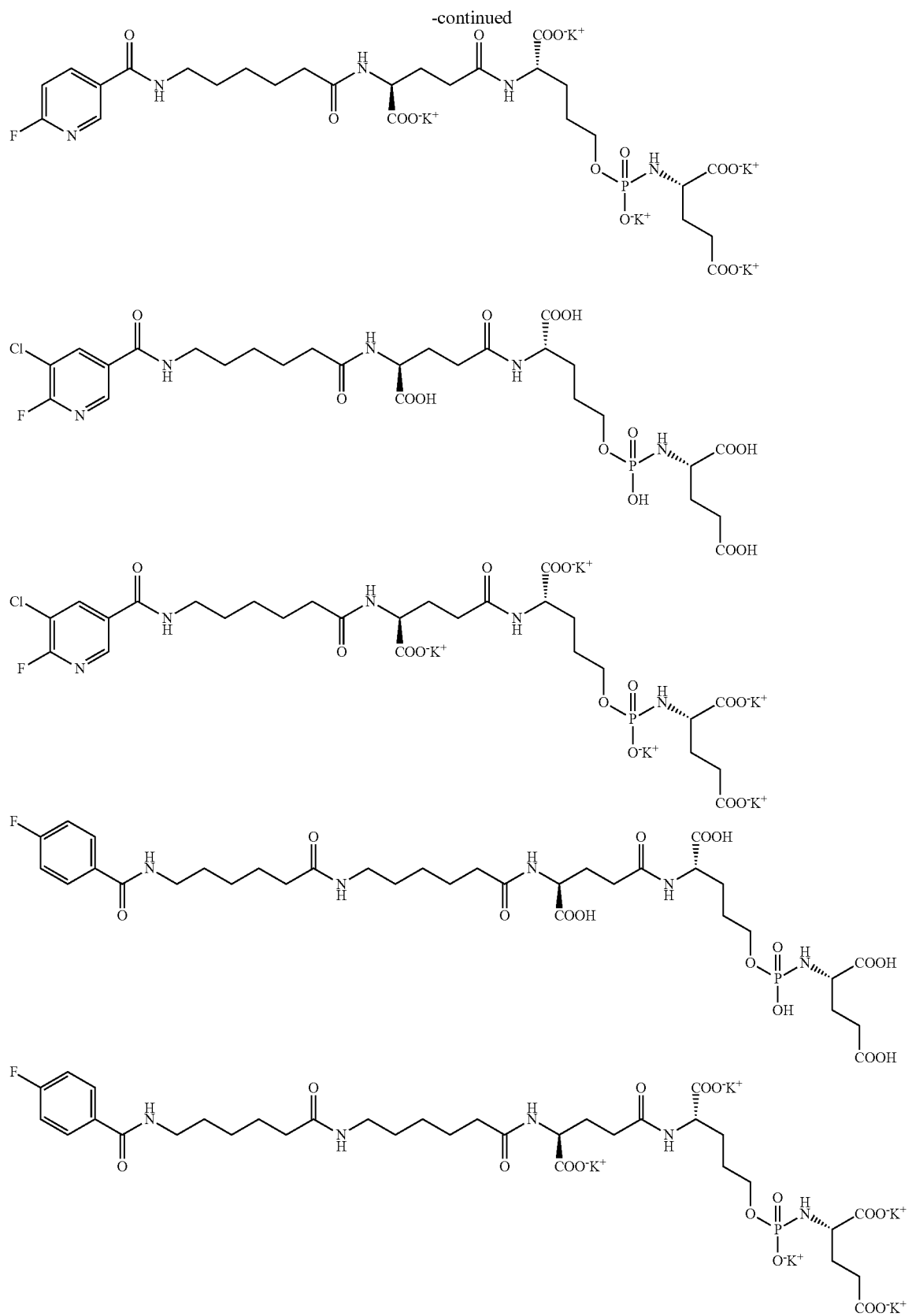
and other pharmaceutically acceptable salts thereof, such as, for example, sodium.
In each of the aspects and embodiments described above where L is a group of formula

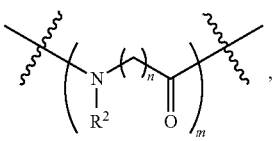, the invention also comprises the analog of that embodiment in which L is a linker comprising a moiety of the formula —NH—CH$_2$CH$_2$—(OCH$_2$CH$_2$—)$_y$—C(O)— y is 1, 2, 3, 4, 5, 6, 7, 8, 9, 10, 11 or 12.

In each of the aspects and embodiments described above when L is a group of formula

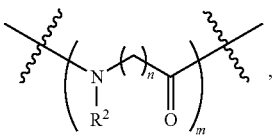, the invention also comprises the analog of that embodiment in which in each of the m monomers one of the n carbon atoms is optionally replaced with a 1,4-phenylene moiety, such as, for example and without limitation,

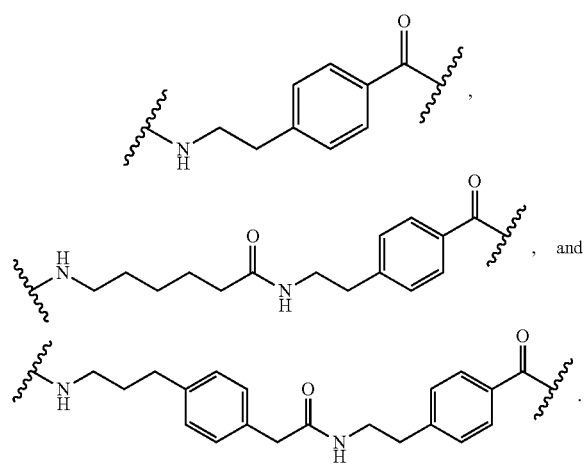, and

In each of the aspects and embodiments described above where L is a group of formula

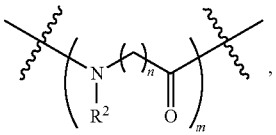, the invention also comprises the analog of that embodiment in which L is a linker in which in one to all of the m monomers are replaced with a moiety of the formula —NH (—CH$_2$CH$_2$—(OCH$_2$CH$_2$—)$_y$—C(O)—), wherein y is 1, 2, 3, 4, 5, 6, 7, 8, 9, 10, 11, or 12, provided that the linear length of the chain is less than 40 atoms. In these embodiments, one of the n carbon atoms of each of the moieties is optionally replaced with a 1,4-phenylene moiety, as described above. So, for example, if there were two such moieties, one or both could have a carbon atom replaced with a 1,4-phenylene moiety.

For the purposes of determining the linear chain length, each 1,4-phenylene moiety is counted as 4 atoms.

For the avoidance of confusion, "linear length of the chain" refers to the number of atoms in the chain and is further defined by the following examples. For example, linker L of formula

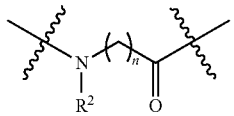

in which m is 2 and each n is 6, the linear chain length is 16 atoms. As another example, linker L of formula

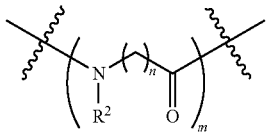

in which m is 3, one of the m monomers is a moiety of the formula —NH(—CH$_2$CH$_2$—(OCH$_2$CH$_2$—)$_y$—C(O)—), wherein y is 2, and in the other of the m monomers one n is 6 and one n is 4, (e.g., 4N(R$^2$)—(CH$_2$)$_6$—C(O)—N(R$^2$)—(CH$_2$)$_4$—C(O)—NR$^2$—CH$_2$CH$_2$—(OCH$_2$CH$_2$—)$_2$—C(O))—, has a linear length of 24 atoms. And as another example, linker L of formula

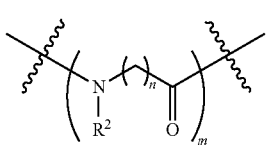

in which m is 3, the n carbon atoms of one of the m monomers is a moiety of the formula (—CH$_2$CH$_2$—(OCH$_2$CH$_2$—)$_y$) wherein y is 2, in the other of the m monomers one n is 4 and the other n is 6 in which one of the carbon atoms is replaced with a 1,4-phenylene moiety (e.g., —((N(R$^2$)—(CH$_2$)$_4$—C(O))—(N(R$^2$)—(CH$_2$)$_5$—(C$_6$H$_6$)—C(O)—NR$^2$—CH$_2$CH$_2$—(OCH$_2$CH$_2$—)$_2$—C(O))—), the linear chain length is 27 atoms.

In an another aspect of the invention, L in the compounds of all the previously described embodiments is a linker of the formula —X—Y—X—, —X—Z—X—, —X—Z—Y—, —X—X—X—, —Y—Y—Y—, —Z—Z—Z— or Y—Z—Y;

wherein X is a moiety of the formula

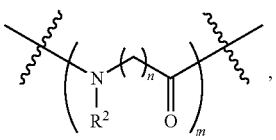

wherein
m is 1, 2, 3, or 4; and
each n is independently 1, 2, 3, 4, 5, 6, 7, 8, 9, 10, 11 or 12; and
Y is a moiety of the formula —CH$_2$CH$_2$—(OCH$_2$CH$_2$—)$_y$, wherein
y is 1, 2, 3, 4, 5, 6, 7, 8, 9, 10, 11 or 12; and
Z is a moiety of the formula

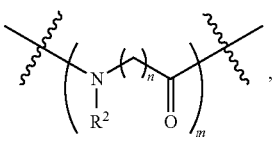

Standard and routine methods can be used to make compounds with the foregoing linkers.

Advantages of Direct $^{18}$F Labeling of PSMA Inhibitors.

The compounds described in the examples herein comprise a radiolabeled pendant group connected to the parent phosphoramidate structure (PMSA inhibitor or fragment thereof) via a linker of the formula:

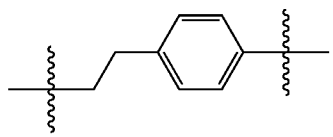

where the linker is connected to the pendent group through an amide bond. Although examples of structures of such pendant groups alone (not attached through to the parent phosphoramidate structure through an amide-bound linker) can be found in the literature as substrates for fluoride substitution ($^{18}$F or $^{19}$F), few examples have a linker connecting a phosphoramidate parent structure and the pendant group through a linker connected to the pendant group through an amide bond. The reactivity of fluoride with pendant groups alone or without an amide-bound linker does not allow one to predict if the same results would be obtained when the amide-bound linker is present on the pendant group. In fact, we have found that in some cases, the literature precedent for fluoride reaction with a pendant group alone did not correlate to our results when that pendant group was attached through an amide bond to a model peptide mimic.

Protecting groups on the PSMA inhibitor, such as benzyl and t-butyl groups, can be later removed after the incorporation of the radiolabel ($^{18}$F) on a pendant group. Furthermore, once the radiolabel has been incorporated into a pendant group attached to a PSMA inhibitor precursor, a final deprotection step can remove all the protecting groups on the PSMA inhibitor in a single step (e.g., t-butyl or benzyl esters).

For maximal utility as a labeled probe for PET, (1) the deprotection reaction is preferably rapid, e.g., occurring within a fraction of the half-life of the radionuclide on the pendant group (e.g., t$_{1/2}$≈110 min. for $^{18}$F); and (2) the conditions of deprotection should not result in the loss of the radiolabel on the pendant group The compounds herein can be deprotected, for example, using catalytic hydrogen transfer. Conventional hydrogenolysis with H$_2$ gas and Pd/C is known to result in dehalogenation on aromatic rings. In fact we have observed this with pendant groups substituted with F on model compounds. However, we have found conditions for catalytic hydrogen transfers in which defluorination is minimized and the reaction is complete within 20 min, and as little as 6 min without the loss of F.

Defluorination can be minimized and/or avoided by controlling the amount of catalyst (Pd/C) used in the deprotection step. In model experiments,

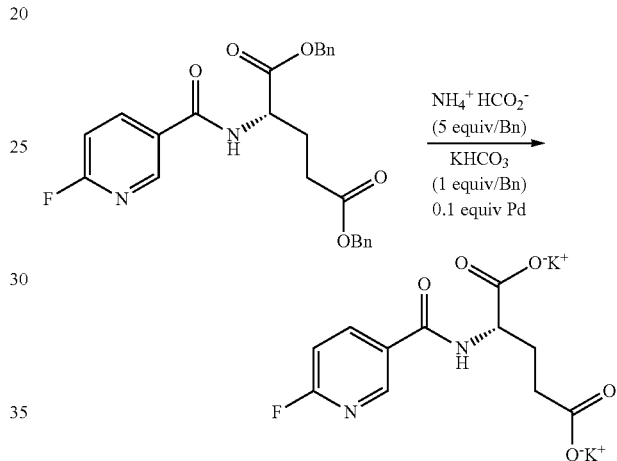

with the fluoro-nicotinamide derivative of glutamate dibenzyl ester we found that with 0.1 molar equivalents of Pd (using 10% Pd/C) the benzyl groups were deprotected within 10 minutes and no defluorination was observed. However, using 0.4 equivalents of Pd, the deprotection of the benzyl esters was complete within 3 minutes but 10% defluorination was observed.

Such optimized yields allows for the use of less of each starting material (i.e., the PSMA inhibitor having a leaving group) and the $^{18}$F anion source, while still providing a final radiolabeled product in high yield.

By utilizing the methods described herein the time and chemical and chromatographic steps involved after labeling can be shortened by a step as compared to methods using the fluorine-18 labeled N-succinimidyl benzoate (SFB) as described in Lapi, S. E., et al., J. Nucl. Med. 2009, 50(12), 2042.

Imaging Methods

In another aspect, the present invention comprises methods for detecting and/or identifying cells presenting PSMA comprising contacting a cell suspected of presenting PSMA with a compound as discussed above, or a composition comprising the compound.

In one embodiment, the methods are suitable for imaging studies of PSMA inhibitors, for example, by studying competitive binding of non-radiolabeled inhibitors.

In still another embodiment, the methods are suitable for imaging of cancer, tumor or neoplasm. In a further embodiment, the cancer is selected from eye or ocular cancer, rectal cancer, colon cancer, cervical cancer, prostate cancer, breast cancer and bladder cancer, oral cancer, benign and malignant tumors, stomach cancer, liver cancer, pancreatic cancer, lung cancer, corpus uteri, ovary cancer, prostate cancer, testicular cancer, renal cancer, brain cancer (e.g., gliomas), throat cancer, skin melanoma, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, neurofibromatosis, tuberous sclerosis, hemangiomas, and lymphangiogenesis.

The methods are suitable for imaging any physiological process or feature in which PSMA is involved. Typically, imaging methods are suitable for identification of areas of tissues or targets which express high concentrations of PSMA. Typical applications include imaging glutamateric neurotransmission, presynaptic glutamatergic neurotransmission, malignant tumors or cancers that express PSMA, prostate cancer (including metastasized prostate cancer), and angiogenesis. Essentially all solid tumors express PSMA in the neovasculture. Therefore, present methods can be used to image nearly all solid tumors including lung, renal cell, glioblastoma, pancreas, bladder, sarcoma, angiosarcoma melanoma, breast, colon, germ cell, pheochromocytoma, esophageal and stomach. Also, certain benign lesions and tissues including endometrium, schwannoma and Barrett's esophagus can be imaged according to the present methods.

In certain embodiments, the radiolabeled compound is detected by positron emission tomography (PET).

In certain other embodiment, the radiolabeled compound is detected by positron emission tomography—computed tomography (PET/CT).

In one embodiment, the subject of the methods may be a human, rat, mouse, cat, dog, horse, sheep, cow, monkey, avian, or amphibian. In another embodiment, the cell is in vivo or in vitro. In certain embodiments, the cells being images or detected are in vivo.

Typical subjects to which compounds described herein may be administered will be mammals, particularly primates, especially humans. For veterinary applications, a wide variety of subjects will be suitable, e. g. livestock such as cattle, sheep, goats, cows, swine and the like; poultry such as chickens, ducks, geese, turkeys, and the like; and domesticated animals particularly pets such as dogs and cats. For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids and cell samples of the above subjects will be suitable for use such as mammalian, particularly primate such as human, blood, urine or tissue samples, or blood urine or tissue samples of the animals mentioned for veterinary applications.

In certain embodiments, a kit can be provided that contains from about 1 to about 30 mCi of the radionuclide-labeled imaging agent described above, in combination with a pharmaceutically acceptable carrier. The imaging agent and carrier may be provided in solution or in lyophilized form. When the imaging agent and carrier of the kit are in lyophilized form, the kit may optionally contain a sterile and physiologically acceptable reconstitution medium such as water, saline, buffered saline, and the like. The kit may provide a compound, as discussed above, in solution or in lyophilized form, and these kit components may optionally contain stabilizers such as NaCl, silicate, phosphate buffers, ascorbic acid, gentisic acid, and the like. Additional stabilization of kit components may be provided in this embodiment, for example, by providing the reducing agent in an oxidation-resistant form. Determination and optimization of such stabilizers and stabilization methods are well within the level of skill in the art.

In certain embodiments, a kit provides a non-radiolabeled precursor to be combined with a radiolabeled reagent on-site, such as Na[$^{18}$F] or K[$^{18}$F].

The radiolabeled compounds herein (i.e., imaging agents) may be used in accordance with the methods described herein by one of skill in the art. Images can be generated by virtue of differences in the spatial distribution of the imaging agents which accumulate at a site when contacted with PSMA. The spatial distribution may be measured using any means suitable for the particular label, for example, a PET apparatus. The extent of accumulation of the imaging agent may be quantified using known methods for quantifying radioactive emissions. A particularly useful imaging approach employs more than one imaging agent to perform simultaneous studies.

In general, a detectably effective amount of the imaging agent is administered to a subject. As used herein, "a detectably effective amount" of an imaging agent is an amount sufficient to yield an acceptable image using equipment which is available for clinical use. A detectably effective amount of an imaging agent may be administered in more than one injection. The detectably effective amount of the imaging agent can vary according to factors such as the degree of susceptibility of the individual, the age, sex, and weight of the individual, idiosyncratic responses of the individual, and the dosimetry. Detectably effective amounts of the imaging agent can also vary according to instrument and film-related factors. Optimization of such factors is well within the level of skill in the art.

The amount of imaging agent used for diagnostic purposes and the duration of the imaging study will depend upon the radionuclide used to label the agent, the body mass of the patient, the nature and severity of the condition being treated, the nature of therapeutic treatments which the patient has undergone, and on the idiosyncratic responses of the patient. Ultimately, the attending physician will decide the amount of imaging agent to administer to each individual patient and the duration of the imaging study. In certain embodiments, a safe and sufficient amount of the compounds herein can be in the range of from about 0.01 mg to about 200 mg per dose.

Definitions

The compounds herein described may have one or more charged atoms. For example, the compounds may be zwitterionic, but may be neutral overall. Other embodiments may have one or more charged groups, depending on the pH and other factors. In these embodiments, the compound may be associated with a suitable counter-ion. It is well known in the art how to prepare salts or exchange counter-ions. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Counter-ions may be changed, for example, by ion-exchange techniques such as ion-exchange chromatography.

All zwitterions, salts and counter-ions are intended, unless the counter-ion or salt is specifically indicated. In certain embodiments, the salt or counter-ion may be pharmaceutically acceptable, for administration to a subject. Pharmaceutically acceptable salts are discussed later.

The term "protecting group" as used herein, is defined as above. In some embodiments, the "protecting group" is introduced to the phosphorous acid to provide an ester. These "protecting groups" include, but are not limited to, acetyl, benzolyl, p-methoxybenzyl ether and pivolyl.

In some embodiments, the "protecting group" is used to introduce an in vivo hydrolyzable ester, which is a pharmaceutically acceptable ester that can be hydrolyzed in the organism being treated, preferably a human or animal body, to produce the parent acid or alcohol. Suitable pharmaceutically acceptable esters for carboxylic and phosphorus acids include $C_{1-6}$-alkoxymethyl esters (e.g., methoxymethyl), $C_{1-6}$-alkanoyloxymethyl esters (e.g., for example pivaloyloxymethyl), phthalidyl esters, $C_{3-8}$-cycloalkoxycarbonyloxy$C_{1-6}$-alkyl esters (e.g., 1-cyclohexylcarbonyloxyethyl); 1,3-dioxolen-2-onylmethyl esters (e.g., 5-methyl-1,3-dioxolen-2-onylmethyl; and $C_{1-6}$-alkoxycarbonyloxyethyl esters (e.g., 1-methoxycarbonyloxyethyl) and may be formed at any appropriate carboxylic or phosphorus acid group in the compounds of this invention.

An in vivo hydrolyzable ester of a compound of the invention containing a hydroxy group (e.g., phosphorous acid) includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolyzable ester forming groups for hydroxy include alkanoyl, benzoyl, phenylacetyl and substituted benzoyl and phenylacetyl, alkoxycarbonyl (to give alkyl carbonate esters), dialkylcarbamoyl and N—(N,N-dialkylaminoethyl)-N-alkylcarbamoyl (to give carbamates), N,N-dialkylaminoacetyl and carboxyacetyl. Examples of substituents on benzoyl include morpholino and piperazino linked from a ring nitrogen atom via a methylene group to the 3- or 4-position of the benzoyl ring. A suitable value for an in vivo hydrolyzable amide of a compound of the invention containing a carboxy group is, for example, a N—$C_{1-6}$-alkyl or N,N-di-$C_{1-6}$-alkyl amide such as N-methyl, N-ethyl, N-propyl, N,N-dimethyl, N-ethyl-N-methyl or N,N-diethyl amide.

In other embodiments, compounds of the invention comprising at least one hydrolyzable ester can be used as "prodrugs". The term "prodrug" is intended to represent covalently bonded carriers, which are capable of releasing the active ingredient when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of the invention include compounds wherein an amino, hydroxy, carboxylic or a similar group is modified. Examples of prodrugs include, but are not limited to esters (e.g., acetate, formate, and benzoate), carbamates (e.g., N,N-dimethylaminocarbonyl), amides (e.g., trifluoroacetylamino, acetylamino, and the like), and the like. A complete discussion of prodrugs is found in Huttunen, K. M. and Rautio *J. Current Topics in Medicinal Chemistry*, 2011, 11, 2265-2287 and Stella, V. J. et al. (2007). *Prodrugs: Challenges and Awards Part* 1. New York: Springer. The disclosure of both references is herein incorporated by reference in its entirety.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" is intended to mean an unsaturated straight or branched chain aliphatic group with one or more carbon-carbon double bonds, having from 2 to 12 carbon atoms, preferably 2-8 carbon atoms, and more preferably 2-6 carbon atoms. Preferred alkenyl groups include, without limitation, ethenyl, propenyl, butenyl, pentenyl, and hexenyl.

The term "haloalkyl" as used herein, means an alkyl group, as defined herein, substituted with one or more (e.g., 1, 2, 3, 4, 5, 6, 7, 8, or 9) halogen groups (i.e., F, Cl, Br, and/or I). Examples of haloalkyl groups include, but are not limited to fluoromethyl, difluoromethyl, trifluoromethyl, chloromethyl, dichloromethyl, trichloromethyl, and n-nonafluorobutyl.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" PSMA with a compound includes the administration of a compound described herein to an individual or patient, such as a human, as well as, for example, introducing a compound into a sample containing a cellular or purified preparation containing PSMA. When the moieties are two reactive chemical species, "contacting" involves the interaction of two moieties for the purpose of chemical reaction (i.e., bond breaking and forming) For example, "contacting" a compound described herein that comprises a nucleophilic group (e.g., an amine) with a compound described herein that comprises an electrophilic group (e.g., a leaving group bound to a phenyl ring or a carbonyl) would result in the displacement of the leaving group and the formation of a new bond between the nucleophile and the atom previously bound to the leaving group.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, trifluoromethanesulfonic (i.e., triflic), toluenesulfonic, methanesulfonic, methyl sulfonate, nitric, benzoic, citric, tartaric, maleic, hydroiodic, alkanoic such as acetic, HOOC—$(CH_2)_n$—COOH where n is 0-4, and the like. "Pharmaceutically acceptable salts" also include, for example, salts formed by the quaternization (e.g., alkylation) of a suitable site in the compound itself, such as methylation of a dimethylamine to form a trimethylammonium group. In such cases, the counterion can be, for example, but not limited to, chloride, phosphate, hydrogen phosphate, bromide, sulfate, hydrogen sulfate, sulfinate, formate, trifluoromethanesulfonate (i.e., triflate), toluenesulfonate, methanesulfonate, methyl sulfonate, nitrate, benzoate, citrate, tartarate, maleate, iodide, acetate, and the like. Non-toxic pharmaceutical base addition salts include salts of bases such as sodium, potassium, calcium, ammonium, and the like. In certain embodiments, the pharmaceutically acceptable salt is a potassium salt. Those skilled in the art will recognize a wide variety of non-toxic pharmaceutically acceptable addition salts.

Pharmaceutical compositions suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Compositions can be administered, for example, by intravenous infusion, orally, topically, intraperitoneally, intravesically or intrathecally.

In certain embodiments, a "pharmaceutically acceptable carrier" refers to a biocompatible solution, having due regard to sterility, p[Eta], isotonicity, stability, and the like and can include any and all solvents, diluents (including sterile saline, Sodium Chloride Injection, Ringer's Injection, Dextrose Injection, Dextrose and Sodium Chloride Injection, Lactated Ringer's Injection and other aqueous buffer solutions), dispersion media, coatings, antibacterial and antifungal agents, isotonic agents, and the like. The pharmaceutically acceptable carrier may also contain stabilizers, preservatives, antioxidants, or other additives, which are well known to one of skill in the art, or other vehicle as known in the art.

EXAMPLES

Example 1

Synthesis of CTT1298 K Salt

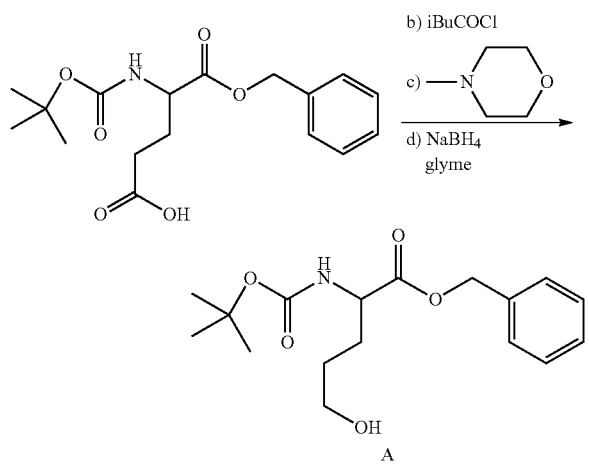

Compound A—
Boc-Glu(OBn) (1 g, 1 equiv) and N-Methylmorpholine (3.55 mmol, 1.2 equiv) were dissolved in 3 mL glyme and stirred at −15 C. iso-Butyloxychloride (2.96 mmol, 1 equiv) was then added and stirred for an additional 15 min. The resulting white precipitate was filtered off and NaBH4 (4.44 mmol, 1.5 equiv) was added to the filterate along with 4 mL of water and stirred for 15 min. The reaction mixture was dissolved in EtOAc and extracted three times with brine. The organic layer was dried over $Mg_2SO_4$ and rotavapped at 40° C. Pure product was obtained on drying (0.726 g, 76%). Characterization confirmed formation of Compound A (Bergman, Y. Tetrahedron asymmetry, 19 (2008), 2861-63).

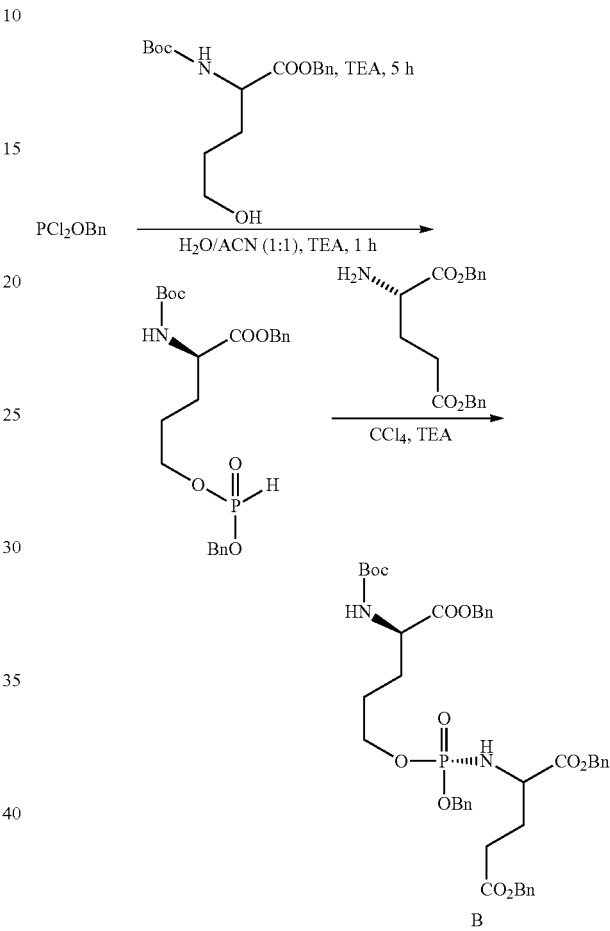

Compound B—
In a flame dried 100 mL flask, 10 mL dry DCM was taken, argon flushed and cooled over dried ice. $PCl_2OBn$ (2.31 mM, 1.5 equiv) and triethyamine (1.855 mM, 1.2 equiv) was added and stirred. A (1.56 mM, 1 equiv) was dissolved in 10 mL of DCM and added to the reaction mixture in parts. After complete addition, dry ice was replaced with ice bath and stirred for 5 h. 1:1 mixture of water: ACN was added and stirred for additional 1 h. Reaction mixture was concentrated, dissolved in EtOAc and washed with 10% HCl, 10% $NaHCO_3$ and brine solution. Organic layer was dried, concentrated down to remove solvent and dried overnight. Crude phosphite was dissolved in 10 mL dry ACN, argon flushed, cooled on ice and 5 mL of $CCl_4$ was added. $NH_2$-Glu(OBn)$_2$ (1.546 mM, 1 equiv) and TEA (4.638 mM, 3.2 equiv) was dissolved in 10 mL ACN and added to the phosphite in parts and stirred for 5 h. The reaction mixture was concentrated and purified using C18 column chromatography using 80:20 MeOH:water as the mobile phase. Compound B was obtained as pale yellow oil (36.7% yield).
$^1$HNMR (300 MHz, CDCl$_3$): δ 2.04 (s, 9H), 2.05-2.06 (m, 3H), 2.07 (m, 2H), 2.09 (m, 2H), 3.48-3.52 (m, 1H), 3.91 (t, 2H), 4.94 (m, 2H), 5.07 (m, 2H), 7.30-7.31 (m, 20H). $^{13}$C NMR (300 MHz, CDCl$_3$): 628.5, 28.9, 30.0, 53.8, 53.9, 66.6, 66.7, 67.2, 67.5, 76.9, 77.3, 77.7, 135.5, 154.8, 172.61, 172.65. $^{31}$P NMR (300 MHz, CDCl$_3$): δ 8.41, 8.44. ESI mass spectroscopy (M+H): calculated X, found X for $C_{43}H_{51}N_2O_{11}P^+$.

dissolved in 2 mL dry DCM, argon flushed and cooled over ice bath. 1 mL of dry TFA was added and stirred for 15 min. DCM was then evaporated off, reaction mixture dissolved in ethyl acetate and washed with 10% NaHCO$_3$ (till pH neutralized), brine and organic layer dried on anhydrous Na$_2$SO$_4$. It was then redissolved in 2 mL dry DMF added to the flask with the pre-activated acid and stirred overnight

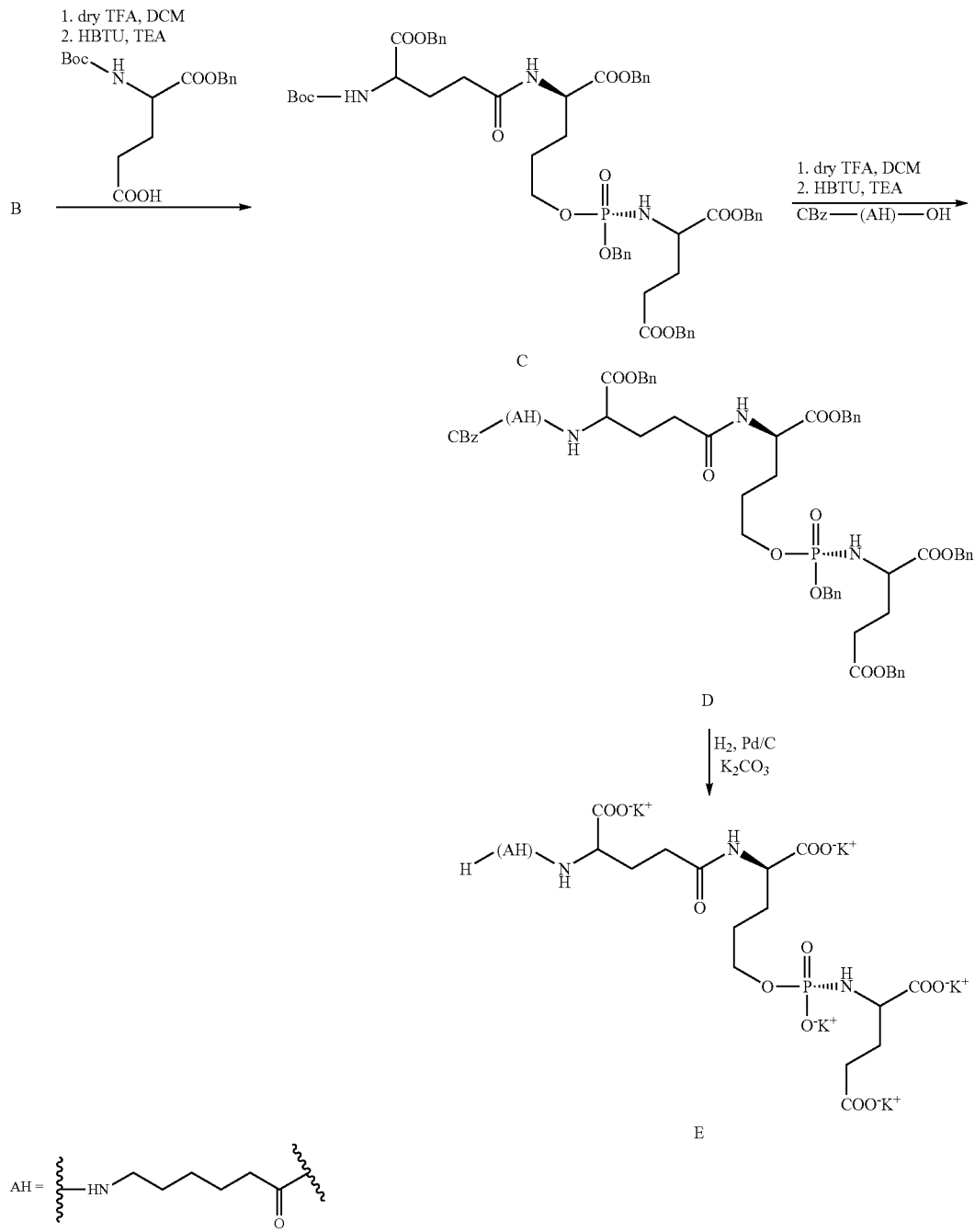

Compound C—

Boc-Glu(OBn) (0.6 g, 1 equiv) was dissolved in 3 mL of dry DMF in a flame dried flask and argon flushed. HBTU (1.95 mmol, 1.1 equiv.) and triethylamine (1.95 mmol, 1.1 equiv.) was added and stirred for 30 minutes for pre-activation of the carboxylic acid. In a separate flask, B was under argon. The reaction mixture was dissolved in ethyl acetate, and washed with 10% NaHCO$_3$ and brine. Organic layer dried over Na$_2$SO$_4$ and dried under vacuum. Purification was carried out using reversed phase C18 chromatography with 80% MeOH-water as the mobile phase. Compound C was isolated in 29% yield. $^1$HNMR (300 MHz, CDCl$_3$): δ 1.41 (s, 9H), 2.59-2.69 (m, 4H), 1.85-1.91 (m, 2H), 2.06-2.15 (m, 2H), 2.25-2.30 (m, 2H), 2.36-2.41 (m, 2H), 3.59 (m, 1H), 3.93 (t, 2H), 4.29 (m, 1H), 4.53 (m, 1H), 4.91-5.00 (m, 2H), 5.04-5.14 (m, 8H), 5.49 (d, 1H, —NH), 6.63 (d, 1H, —NH), 6.74 (d, 1H, —NH), 7.28-7.32 (m, 25H). $^{13}$C NMR (300 MHz, CDCl$_3$): δ 28.5, 28.9, 30.0, 53.8, 53.9, 66.6, 66.7, 67.2, 67.5, 76.9, 77.3, 77.7, 135.5, 154.8, 172.61, 172.65. $^{31}$P NMR (300 MHz, CDCl$_3$): δ 8.48. ESI mass spectroscopy (M+Na): calculated 1021.08, found 1044.4 for C$_{55}$H$_{64}$N$_3$O$_{14}$P$^+$.

Compound D—

The preparation and purification of Compound D was carried out similar to that of Compound C. CBz-AH-OH (AH=aminohexanoic acid) (0.1 g, 0.264 mmol) was pre-activated with HBTU (0.29 mmol, 1.1 equiv.) and TEA (0.29 mmol, 1.1 equiv.). Compound C was treated with a mixture of dry TFA/DCM like in the above case for deprotection of N-terminal Boc- group and then added to the flask with activated CBz-AH-OH. Purification was carried out using reversed phase C18 chromatography with 80% MeOH-water as the mobile phase. Compound D was isolated in 49% yield. $^1$HNMR (300 MHz, CDCl$_3$): δ 1.36-1.39 (m, 2H), 1.57-1.65 (m, 8H), 1.83 (m, 2H), 2.08 (m, 4H), 2.18-2.27 (m, 4H), 2.37 (m, 2H), 3.38 (m, 1H), 3.64 (m, 1H), 3.88 (t, 2H), 4.49 (m, 1H), 4.91-4.94 (m, 2H), 5.03-5.11 (m, 8H), 6.78 (d, 1H, —NH), 6.85 (d, 1H, —NH), 6.92 (d, 1H, —NH), 7.00-7.05 (t, 2H), 7.25-7.30 (m, 25H), 7.78-7.82 (dd, 2H). $^{13}$C NMR (300 MHz, CDCl$_3$): 628.5, 28.9, 30.0, 53.8, 53.9, 66.6, 66.7, 67.2, 67.5, 76.9, 77.3, 77.7, 135.5, 154.8, 172.61, 172.65. $^{31}$P NMR (300 MHz, CDCl$_3$): δ 8.38, 8.41. ESI mass spectroscopy (M+Na): calculated 1021.08, found 1044.4 for C$_{55}$H$_{64}$N$_3$O$_{14}$P$^+$.

CTT1298 K Salt (E)—

To a solution of a Compound D (0.160 g, 0.124 mmol) in THF (1 ml), was added 10% Pd/C (16 mg), K$_2$CO$_3$ (0.044 mg, 0.318 mmol) and H$_2$O (1 ml). The mixture was stirred vigorously, purged with argon(g) and then charged with H$_2$(g) under balloon pressure overnight at room temperature. The solution was filtered through a 0.2 mm PTFE micropore filtration disk (Whatman). The solvent was removed in vacuo to yield a white solid, CTT1298 K Salt in 87% yield.

Example 2

Synthesis of CTT1057 K Salt (G)

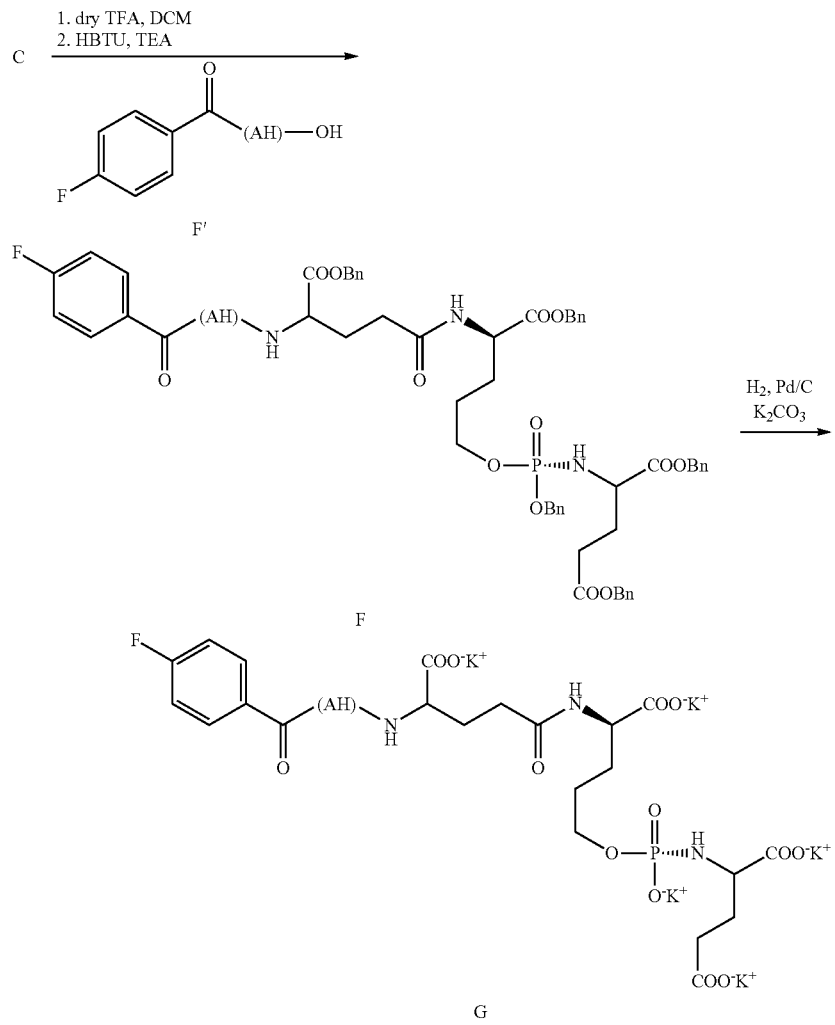

The Boc group was removed from Compound C with dry TFA/DCM mixture and then reacted with p-fluorobenzamidoaminohexanoic acid (F')(0.150 mg, 0.592 mmol), preactivated with HBTU (0.651 mmol, 1.1 equiv) and TEA (0.651 mmol, 1.1 equiv). Purification was carried out using reversed phase C18 chromatography with 80% MeOH-water as the mobile phase. Compound F was isolated in 29% yield. $^1$HNMR (300 MHz, CDCl$_3$): δ 1.36-1.39 (m, 2H), 1.57-1.65 (m, 8H), 1.83 (m, 2H), 2.08 (m, 4H), 2.18-2.27 (m, 4H), 2.37 (m, 2H), 3.38 (m, 1H), 3.64 (m, 1H), 3.88 (t, 2H), 4.49 (m, 1H), 4.91-4.94 (m, 2H), 5.03-5.11 (m, 8H), 6.78 (d, 1H, —NH), 6.85 (d, 1H, —NH), 6.92 (d, 1H, —NH), 7.00-7.05 (t, 2H), 7.25-7.30 (m, 25H), 7.78-7.82 (dd, 2H). $^{13}$C NMR (300 MHz, CDCl$_3$): 628.5, 28.9, 30.0, 53.8, 53.9, 66.6, 66.7, 67.2, 67.5, 76.9, 77.3, 77.7, 135.5, 154.8, 172.61, 172.65. $^{31}$P NMR (300 MHz, CDCl$_3$): δ 8.38, 8.41. ESI mass spectroscopy (M+Na): calculated 1021.08, found 1044.4 for C$_{55}$H$_{64}$N$_3$O$_{14}$P$^+$.

The synthesis for Compound G was carried using the procedure used for synthesis of Compound D. To a solution of Compound F (0.070 g, 0.061 mmol) in THF (1 ml), was added 10% Pd/C (7 mg), K$_2$CO$_3$ (0.021 mg, 0.156 mmol) and H$_2$O (1 ml). CTT1057 K Salt (G) was isolated in 94% yield. $^1$HNMR (300 MHz, D$_2$O): δ 1.18 (m, 4 h), 1.42 (m, 8H), 1.68 (m, 4H), 1.90 (m, 4 h), 2.11 (m, 4H), 3.20 (t, 4 h), 3.56 (m, 1H), 3.85 (m, 4 h), 3.91 (m, 4 h), 6.97-7.06 (m, 4 h), 7.52-7.57 (m, 4 h). $^{31}$P NMR (300 MHz, D$_2$O): δ 8.44. HR mass spectroscopy: calculated 820.31, found 820.4 (M+H), 858.9 (M+K) for C$_{28}$H$_{40}$FN$_4$O$_{14}$P$^+$.

Example 3

Synthesis of CTT1299 K Salt (I)

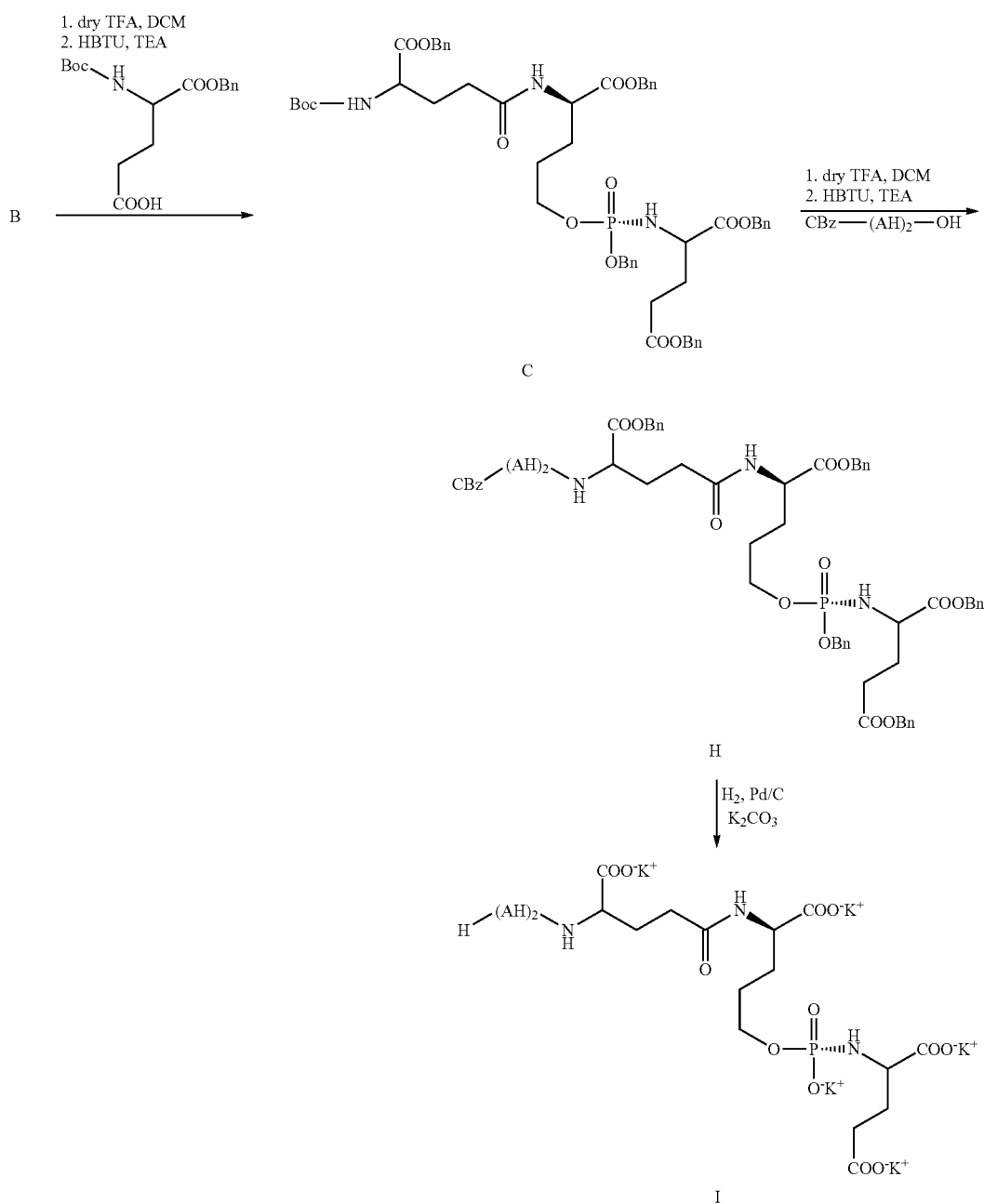

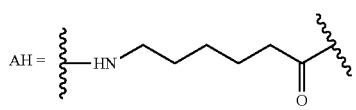

Compound H—

CBz-AH2-acid (AH=aminohexanoic acid) (0.1 g, 0.264 mmol) was pre-activated with HBTU (0.29 mmol, 1.1 equiv.) and TEA (0.29 mmol, 1.1 equiv.). Compound C was treated with a mixture of dry TFA/DCM like in the above case for deprotection of N-terminal Boc- group and then added to the flask with activated CBz-AH2-acid. Purification was carried out using reversed phase C18 chromatography with 80% MeOH-water as the mobile phase. Compound H was isolated in 49% yield. $^1$HNMR (300 MHz, CDCl$_3$): δ 1.28-1.30 (m, 4H), 1.41-1.46 (m, 4H), 1.56-1.61 (m, 6H), 1.86-1.89 (m, 2H), 2.09-2.27 (m, 10H), 2.37-2.39 (m, 2H), 3.12-3.18 (m, 4H), 3.74 (m, 1H), 3.89 (m, 2H), 4.51 (m, 2H), 4.91-4.96 (m, 2H), 5.05-5.11 (m, 10H), 5.95 (d, 1H, —NH), 6.98 (d, 1H, —NH), 7.03 (d, 1H, —NH), 7.27-7.31 (m, 27H). $^{31}$P NMR (300 MHz, CDCl$_3$): δ 8.47. ESI mass spectroscopy: calculated 1281.4, found 1282.4 (M+H), 1305.6 (M+Na) for $C_{70}H_{84}N_5O_{16}P^+$.

CTT1299 K Salt (I)—

To a solution of a benzyl ester protected phosphoramidate (H) (0.160 g, 0.124 mmol) in THF (1 ml), was added 10% Pd/C (16 mg), K$_2$CO$_3$ (0.044 mg, 0.318 mmol) and H$_2$O (1 ml). The mixture was stirred vigorously, purged with argon (g) and then charged with H$_2$(g) under balloon pressure overnight at room temperature. The solution was filtered through a 0.2 mm PTFE micropore filtration disk (Whatman). The solvent was removed in vacuo to yield a white solid, Compound I in 87% yield. $^1$HNMR (300 MHz, D$_2$O): δ 1.14-1.19 (m, 2H), 1.36 (m, 4H), 1.38-1.50 (m, 10H), 1.59-1.68 (m, 2H), 1.89 (m, 2H), 1.99-2.19 (m, 8H), 2.86 (t, 2H), 3.34 (m, 1H), 3.56 (dd, 1H), 3.94 (m, 3H). $^{31}$P NMR (300 MHz, D$_2$O): δ 8.43. HR mass spectroscopy: calculated 698.30, found 698.35 (M+H) for $C_{27}H_{49}N_5O_{14}P^+$.

Example 4

Synthesis of CTT1059 K Salt (J)

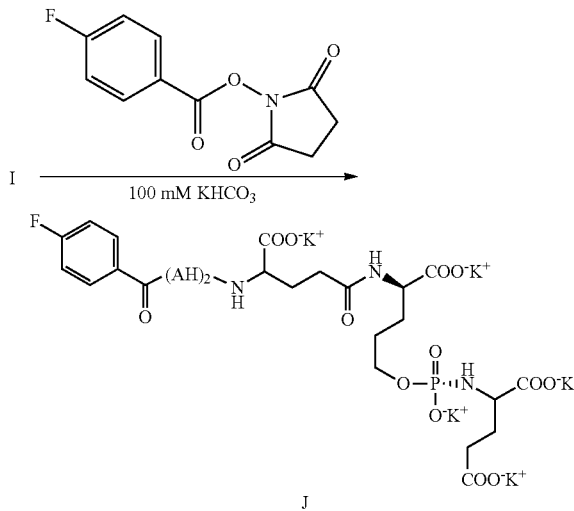

CTT1059 K Salt (J)—

A solution of I (0.028 g, 0.003 mmol, 1.5 equiv) was made in 5000 µL of 100 mmol KHCO$_3$ and p-fluorobenzoic acid succinimidyl ester (0.005 g, 1 equiv) in 400 µL THF was added and stirred for 5 h. The unreacted I was scavenged by stirring with 5 mg Si-Isocyanate resin (SiliCycle, Inc., Quebec, Canada) overnight at room temperature. The solution was subsequently centrifuged (7800 rcf, 10 min) and the supernatant was lyophilized in a 2 mL microcentrifuge tube. The unreacted and/or hydrolyzed SFB was removed by successively triturating the lyophilized solid with 1 mL portions of DMSO and centrifuging the mixture (16,200 rcf, 1 min) after each wash; this process was repeated 10 times. The resulting solid was dried in vacuo providing the desired 4-fluorobenzamido-phosphoramidate J in quantitative yield. $^1$HNMR (300 MHz, D$_2$O): δ 1.09-1.19 (m, 2H), 1.16-1.24 (m, 6H), 1.30-1.35 (m, 2H), 1.41-1.45 (m, 5H), 1.61-1.68 (m, 5H), 1.99-2.07 (m, 6H), 2.14-2.21 (m, 2H), 2.91-2.95 (m, 2H), 3.16-3.21 (m, 2H), 3.25-3.33 (m, 2H), 3.54-3.56 (m, 2H), 3.87-3.96 (m, 2H), 7.02-7.08 (m, 2H), 7.56-7.61 (m, 2H). $^{31}$P NMR (300 MHz, D$_2$O): δ 8.43. HR mass spectroscopy: calculated 820.38, found 820.43 (M+H) and 858.40 (M+K) for $C_{34}H_{51}N_5FO_{15}P^+$.

Example 5

Synthesis of [181]CTT1059 K Salt (K)

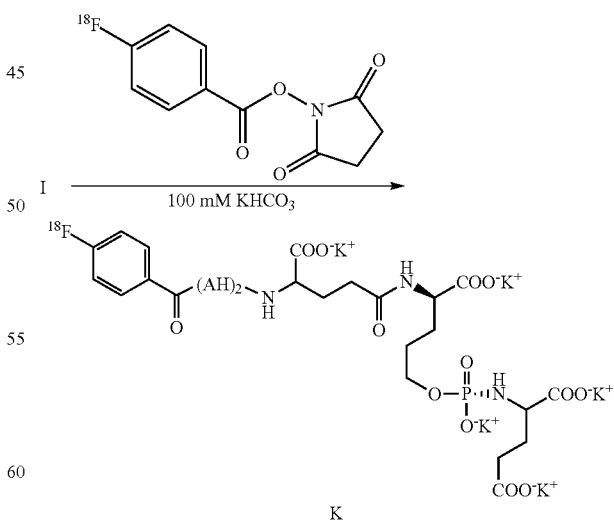

[18F]CTT1059 K Salt (K) was synthesized by a procedure similar to the synthesis of Compound J, except p-$^{18}$fluorobenzoic acid succinimidyl ester was used in the place of p-fluorobenzoic acid succinimidyl ester.

Example 6

Synthesis of [18F]CTT1057 K Salt (L)

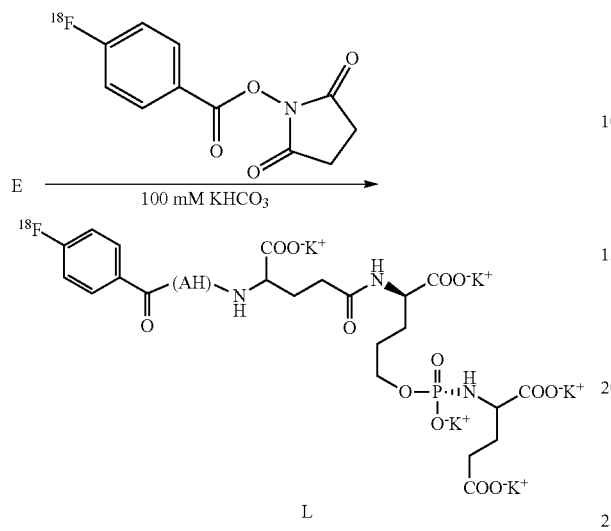

[18F]CTT1057 K Salt (L) was synthesized by a procedure similar to the synthesis of Compound J, except Compound E was used in place of Compound I, and p-[18]fluorobenzoic acid succinimidyl ester was used in the place of p-fluorobenzoic acid succinimidyl ester.

Example 7

Acid Stability of 2-(3-Hydroxypropyl)-Glycine Based Compounds

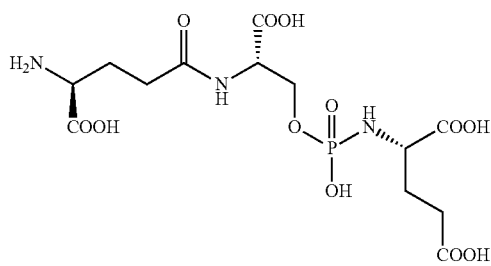

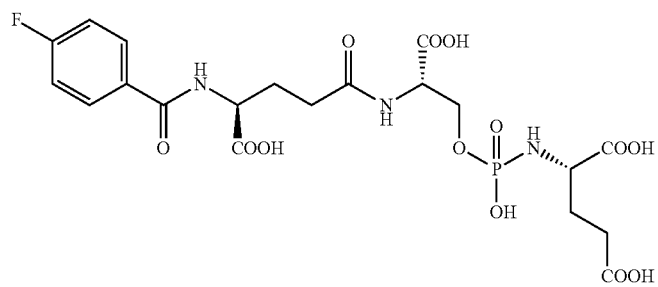

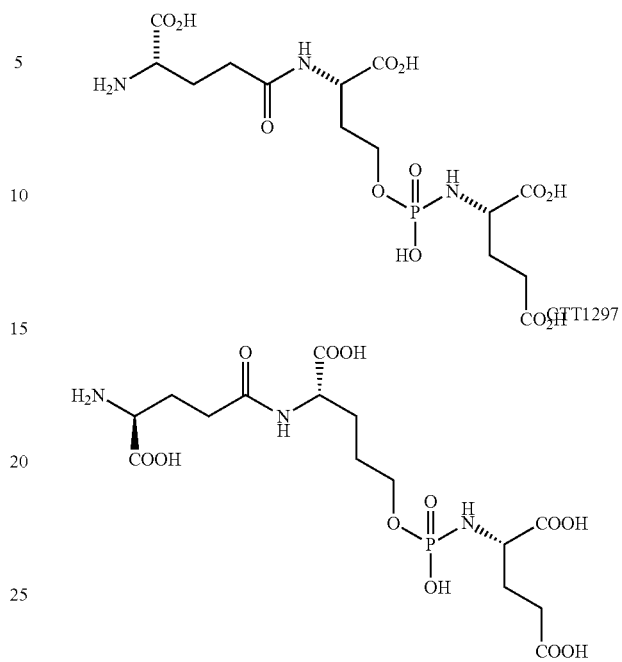

Acid stability studies performed on CTT1054, CTT1000, and CTT1297 determined that CTT1297 has enhanced acid and base stability over CTT1054 and CTT1000. Replacing the serine residue in CTT1054 with a homoserine (CTT1000) or 2-(3-hydroxypropyl)-glycine (CTT1297) residue was expected to make CTT1297 and CTT1000 less prone to beta-elimination of the phosphate group. However, the dramatically enhanced acid stability of CTT1297 over CTT1054 and even CTT1000 was not expected. CTT1297 is stable for 8 hours at pH 3, where CTT1054 decomposes at pH 6 and CTT1000 begins to decompose at pH 4.5. $^{31}$P NMR data acquired over 8 hours for CTT1054 (pH 6) and CTT1297 (pH 4, 3, and 2), and CTT1000 (pH 4.5) are shown in FIGS. 1-7.

The procedures for determining pH stability by $^{31}$P NMR are detailed as follows. The sample (~4 mg) was dissolved buffer (~1 mL of a 1 M solution) resulting in an approximately 5 mM solution of the analyte. The pH was adjusted as necessary (e.g., with HCl) and that time was defined as t=0. An initial $^{31}$P NMR spectra was obtained (t~0.5 h) and acquired each hour (1-8 h) The external reference for $^{31}$P NMR was triphenylphosphine oxide (27 ppm).

Example 8

Binding Interactions in PSMA—Crystal Structures

-continued

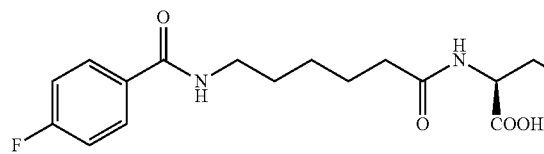
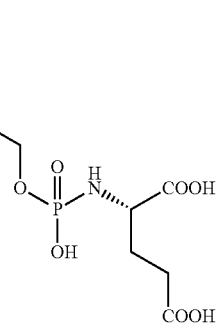

CTT1057

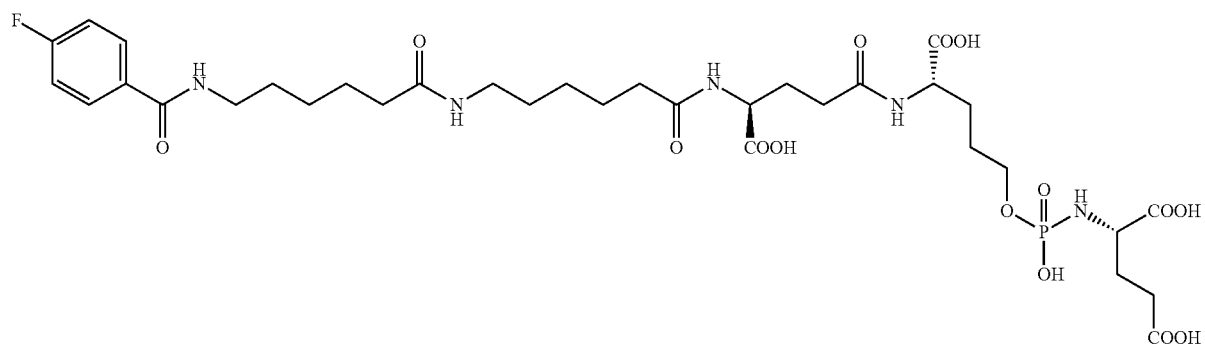

CTT1059

Figure 8:
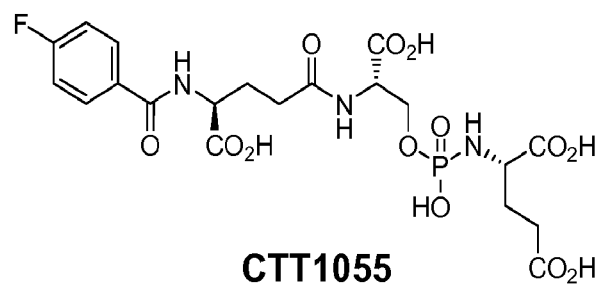
FIG. 8 shows an X-ray crystal structure of CTT1055 co-crystalized in the extracellular domain of PSMA. There is no presence of an induced arene binding site. Red indicates areas of high oxygen density, blue indicates areas of high nitrogen density and green indicates areas of high hydrogen density.
Figure 8:
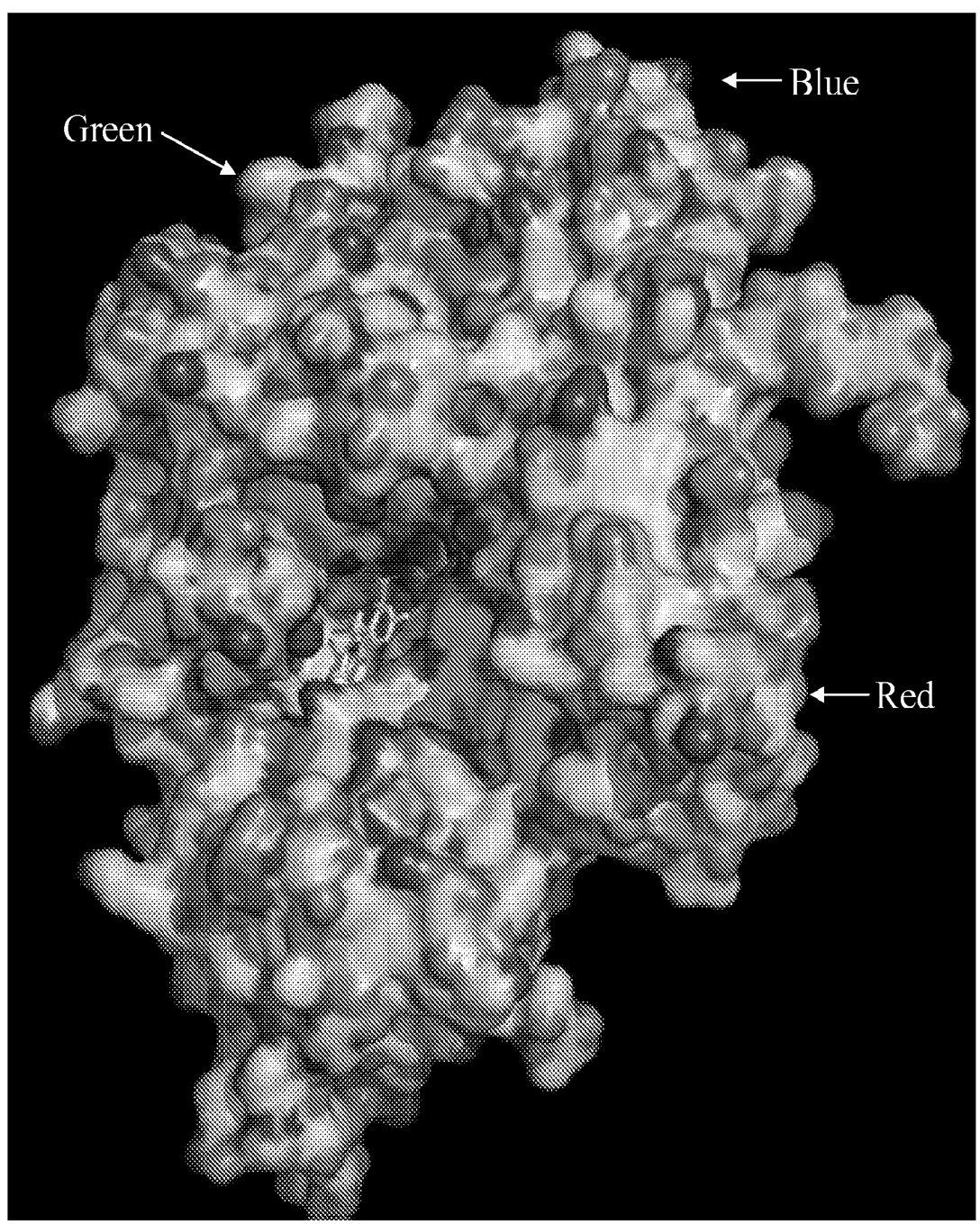
Figure 9:
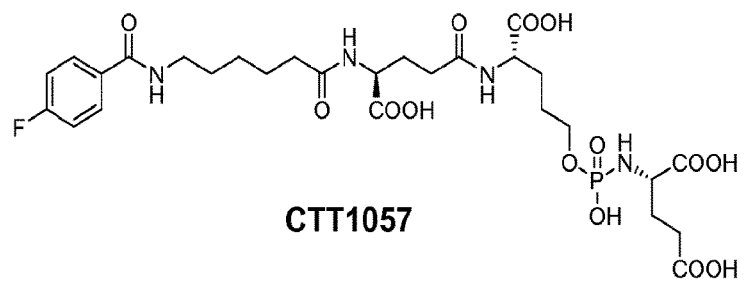
FIG. 9 shows an X-ray crystal structure of CTT1057 co-crystalized in the extracellular domain of PSMA. The arene binding site is induced by the fluorobenzamide group of CTT1057. Red indicates areas of high oxygen density, blue indicates areas of high nitrogen density and green indicates areas of high hydrogen density.
Figure 9:
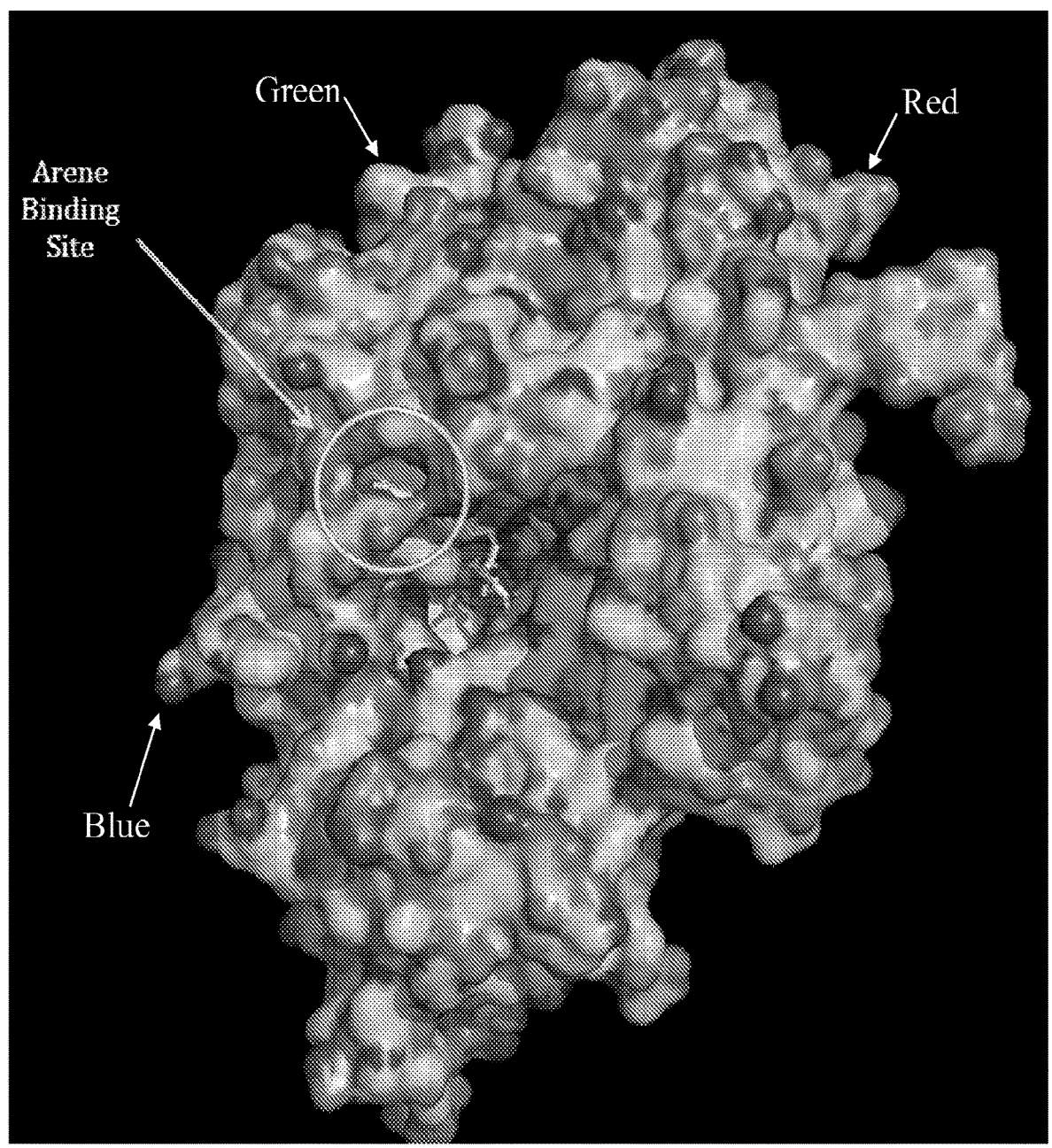

X-ray crystal structures of CTT1055 and CTT1057 co-crystallized with the extracelluar domain of PSMA were obtained, and revealed unexpected additional binding interactions for CTT1057. Specifically, it was discovered that the aminohexanoic acid linker in CTT1057 allows the p-fluorobenzamide group to induce an additional binding interaction with the recently identified remote arene binding site (Zhang, A. X., et al., *A remote arene-binding site on prostate specific membrane antigen revealed by antibody-recruiting small molecules*. J. Am. Chem. Soc., 2010, 132(36): p. 12711-6.). Zhang and co-workers reported the arene binding site to be induced with a dinitrophenyl ring linked to the substrate recognizing a compound with triazole-oxyethylene linkers of various length. It was not predictable from Zhang compounds, in which the dinitrophenyl interacted with the remote arene binding site, whether a compound presenting a flurophenyl moiety (e.g., CTT1057) would similarly interact with the remote arene binding site. There are stark steric and electronic differences between the dinitrophenyl ring used by Zhang and the p-fluorobenzamide of the compounds of the present invention. In addition, it was not predicted that length, configuration and interactive properties of the triazole-oxyethylene linkers used by Zhang and co-workers could be achieved with an aliphatic linker such as the aminohexanoic acid found in CTT1057. Crystal structures of CTT1055 and CTT1057 bound in PSMA are shown in FIGS. 8 and 9 to illustrate the different modes of binding.

Figure 13:
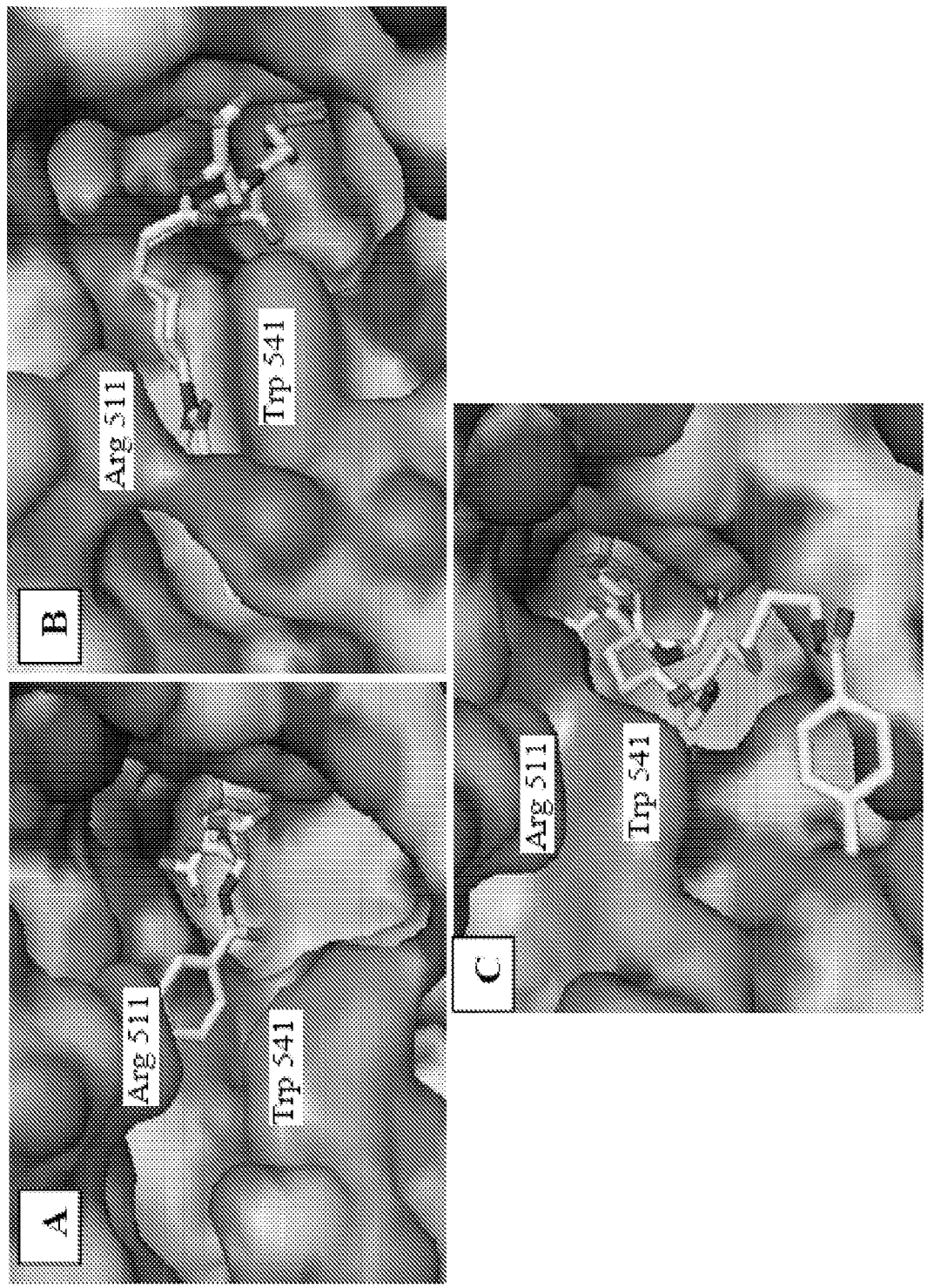
FIG. 13 shows crystal structures of A) CTT1056; B) CTT1057; and C) CTT1059 with PSMA. Arene-binding patch containing Arg511 and Trp541 residues are labeled as "Arg511" and "Trp541" respectively.

There are slight differences in the positioning between the AH linker and P1 carboxylate in CTT1057 compared to CTT1056 and CTT1059. While the P1 carboxylate of CTT1056 and CTT1059 interact directly with both Arg534 and Arg536, the corresponding part in CTT1057 is shifted by approximately 1.1 Å (for the carbon atom of the P1 carboxylate), engaging NH1 of Arg536 only (3.1 Å) (FIG. 13).

The most important and prominent difference in positioning of the inhibitor distal components are found in the lipophilic aminohexanoic linker and the fluoro-phenyl ring. For CTT1056, the distance between the linker to the distal ring is approximately 13 Å. The distal fluoro-benzoyl group is positioned parallel to the guanidinium group of the Arg463 at the distance of approximately 4.0 Å with weak i-cation interactions in the arene binding site as seen in CTT1057 (FIG. 13, A). For CTT1057, the terminal fluoro-benzoyl functionality is wedged into the arene-binding cleft located at the "entrance lid" of the enzyme that is shaped by the side chains of Trp541 and Arg511 on sides and by the Arg463 side-chain at the bottom. The plane of the fluoro-benzoyl ring is virtually parallel to both indole and guanidinium groups of Trp541 and Arg511, respectively, and both these residues contribute to inhibitor binding (FIG. 13, B). Finally, in the case of CTT1059 with the longest linker (approximately 28 Å) the distal part of the inhibitor is not seen in the electron density at all (FIG. 13, C).

Example 9

In Vitro and In Vivo Performance

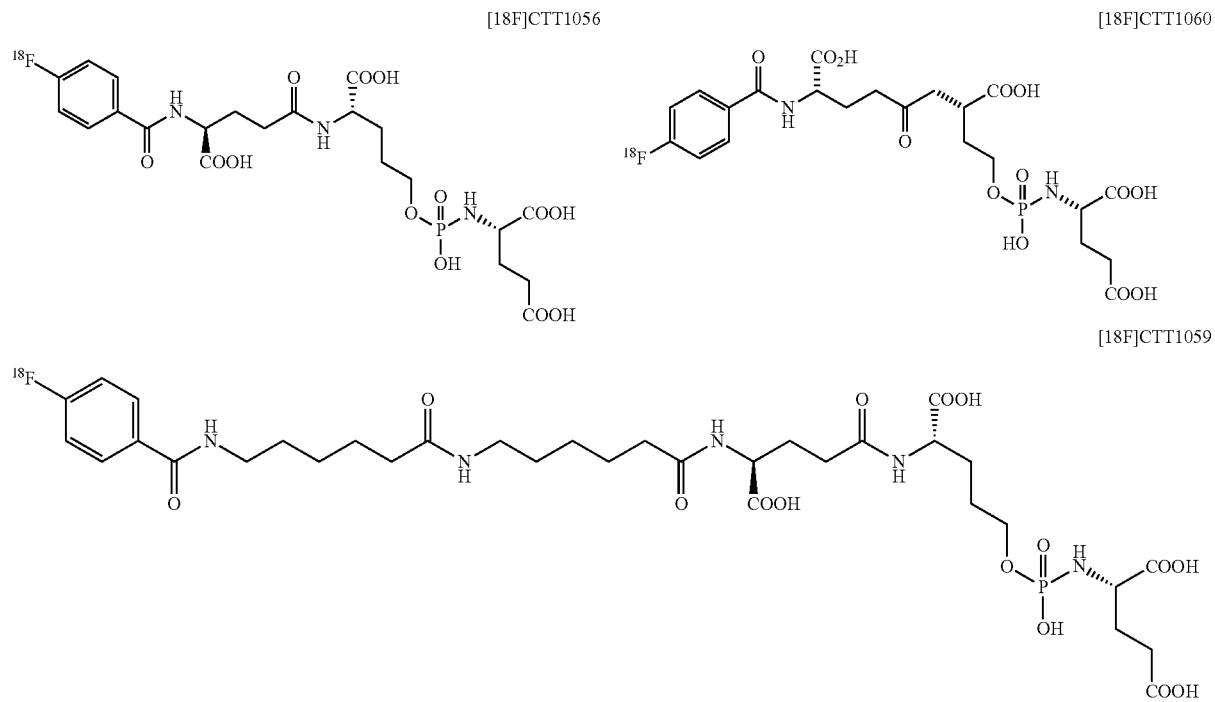

Figure 10:
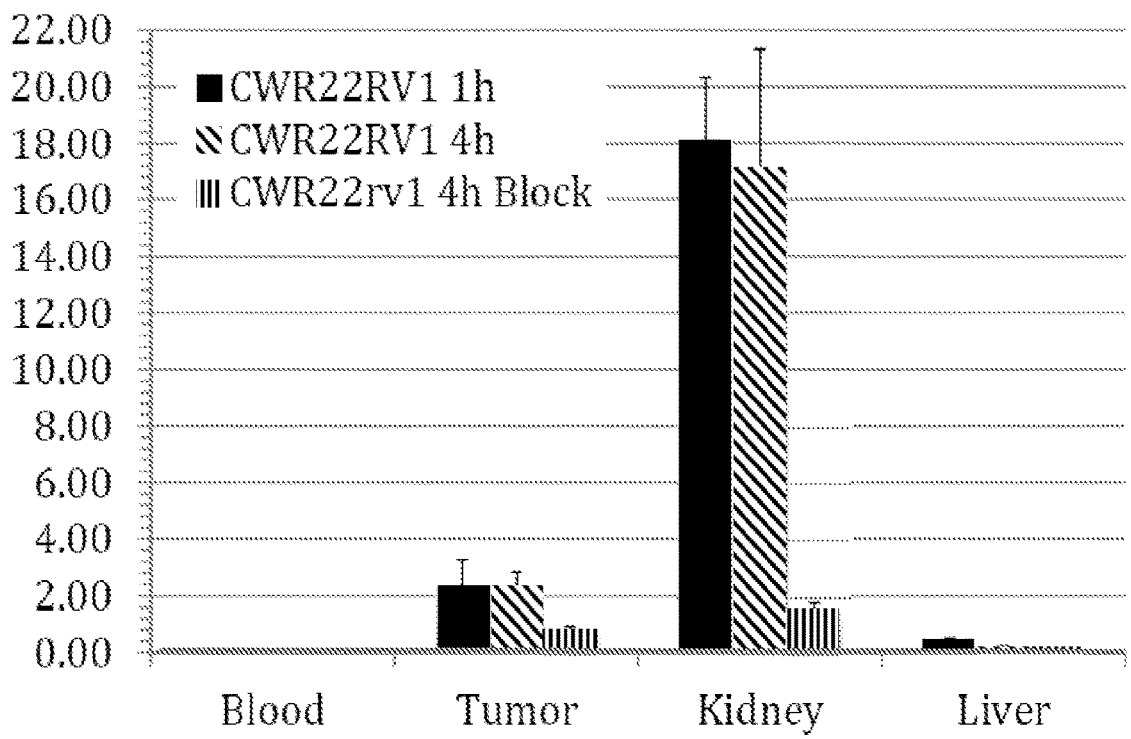
FIG. 10 shows biodistribution of A) CTT1057, and B) CTT1059 in a mouse model with CWR22RV1 cell xenograft tumors.
Figure 10:
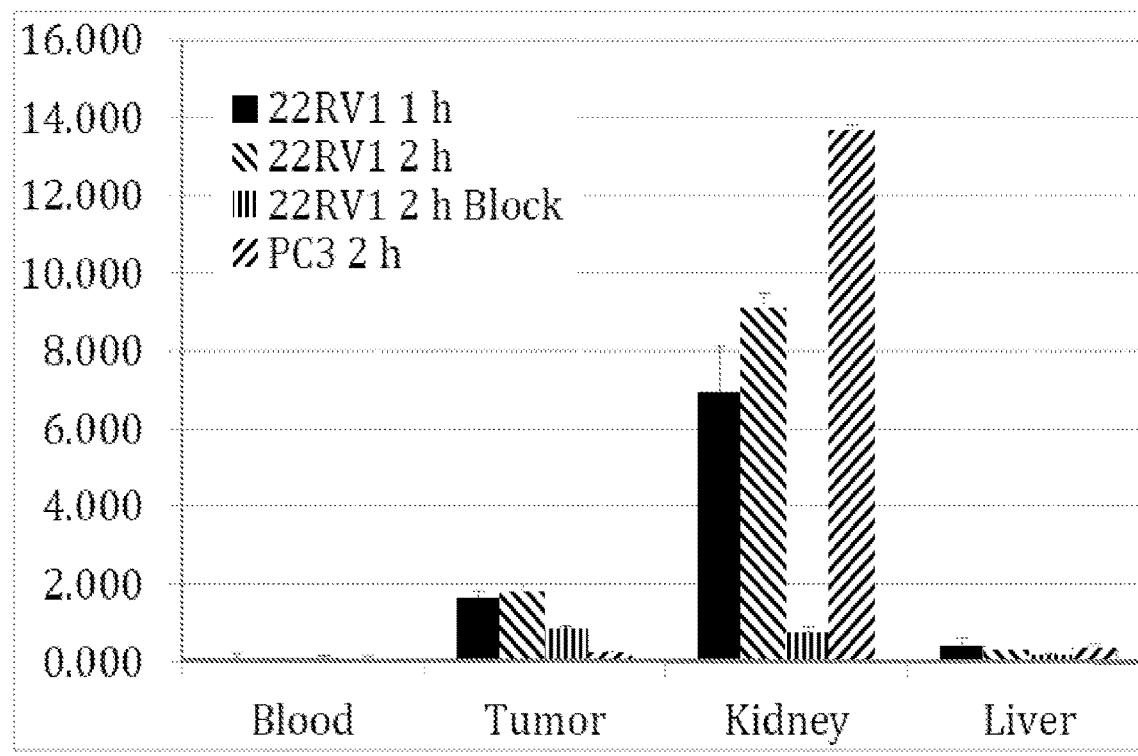
Figure 11:
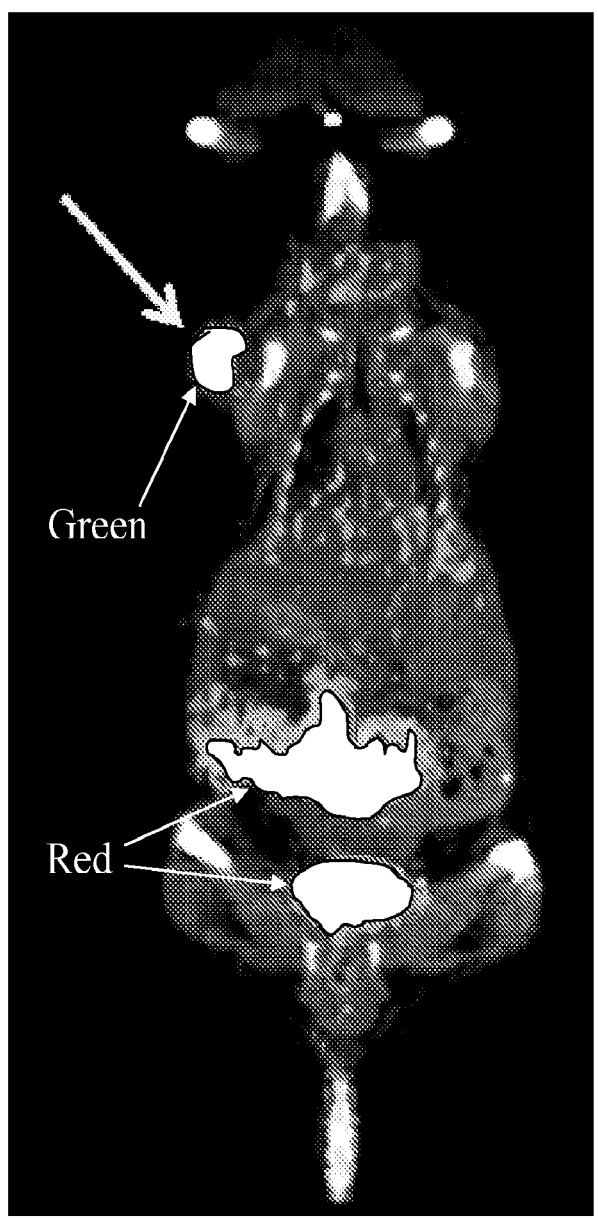
FIG. 11 shows a PET imaging scan of CWR22RV1 tumor xenograft 2 hours after injection with CTT1056. The arrow indicates the tumor location. Red indicates areas of high uptake of the radiolabeled agents, green indicates medium uptake, and blue indicates areas of low uptake.
Figure 12:
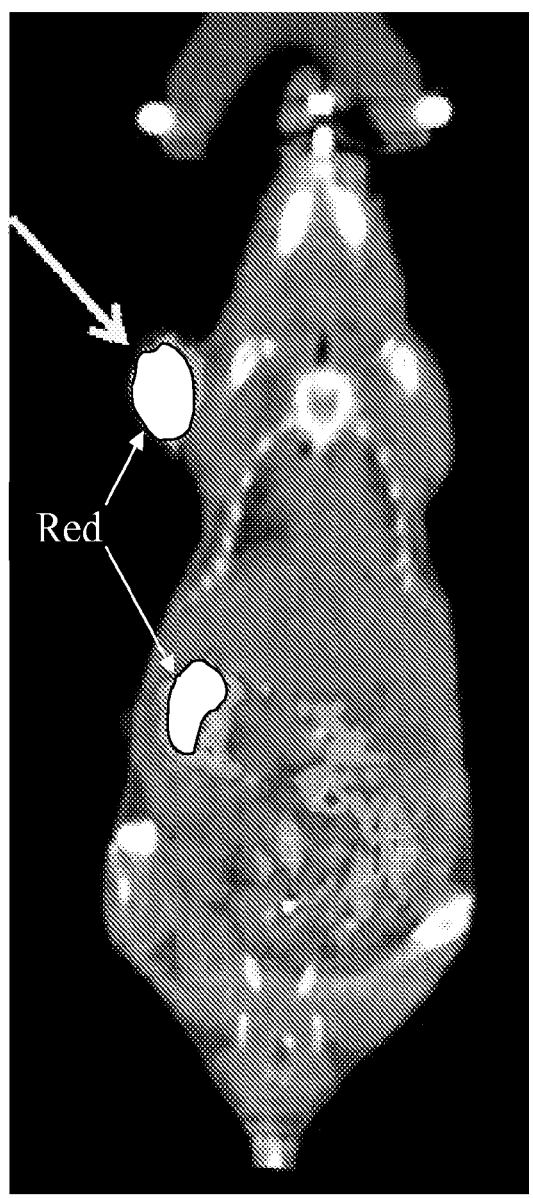
FIG. 12 shows a PET imaging scan of CWR22RV1 tumor xenograft 5 hours after injection with CTT1057. The arrow indicates the tumor location. Red indicates areas of high uptake of the radiolabeled agents, green indicates medium uptake, and blue indicates areas of low uptake.

The in vitro and in vivo performance of the PET imaging agents containing a 2-(3-hydroxypropyl)-glycine residue ([18F]CTT1056, [18F]CTT1057, and [18F]CTT1059) were determined and compared against PET imaging agents containing a homoserine residue ([18F]CTT1055 and [18F]CTT1060). PET imaging and biodistribution experiments were preformed according the procedures of *PSMA-targeted SPECT agents: Mode of Binding effect on in vitro Performance*. Nedrow-Byers, J. R.; Moore, A. L.; Ganguly, T.; Hopkins, M. R.; Fulton, M. D.; Benny, P. D.; Berkman, C. E. The Prostate. 2012 (in press, PMID: 22911263, doi: 10.1002/pros.22575). While all compounds exhibited irreversible modes of binding consistent for this class of compounds and demonstrated similar $IC_{50}$ values, enhanced tumor:blood ratios were observed for the 2-(3-hydroxypropyl)-glycine containing agents (Table 1). [18F]CTT1055 and [18F]CTT1060 imaging and biodistribution results were obtained using LNCaP tumor xenografts in mouse models while [18F]CTT1056, [18F]CTT1057, and [18F]CTT1059 imaging and biodistribution results were obtained using CWR22RV1 tumor xenografts in mouse models. PSMA expression in CWR22RV1 xenografts was reported to be considerably lower compared to LNCaP xenografts (Regino, C. A., et al., *Preclinical evaluation of a monoclonal antibody (3C6) specific for prostate-specific membrane antigen*. Curr Radiopharm, 2009. 2(1): p. 9-17.). Therefore it was expected that tumor uptake values in CWR22RV1 xenografts would be lower than uptake values for LNCaP xenografts. Despite the lower PSMA expression in the 22RV1 xenografts, the collective results reveal excellent biodistribution (FIGS. 10A and 10B) and PET images of tumor xenografts (CWR22RV1 cells) for [18F]CTT1057 and [18F]CTT1059 (FIGS. 11 and 12, respectively) compared to $1^{st}$ and $2^{nd}$ generation agents [18F]CTT1055 and [18F]CTT1060, respectively.

TABLE 1

Comparison of PET imaging agents.

| Compound | $IC_{50}$ (nM) | Tumor uptake (% ID/g) 1 h | Tumor uptake (% ID/g) 2 h | Tumor uptake (% ID/g) 4 h | Tumor: Blood 1 h | Tumor: Blood 2 h | Tumor: Blood 4 h |
|---|---|---|---|---|---|---|---|
| [18F]CTT1055 * | 0.7 irreversible | | 1.24 | | | 9:1 | |
| [18F]CTT1060 * | 0.8 irreversible | 2.00 | | | 8:1 | | |
| [18F]CTT1056 | 1.3 irreversible | 1.55 | 1.68 | | 8:1 | 21:1 | |
| [18F]CTT1057 | 0.4 irreversible | 2.35 | | 2.33 | 22:1 | | 265:1 |

TABLE 1-continued

Comparison of PET imaging agents.

| Compound | IC$_{50}$ (nM) | Tumor uptake (% ID/g) 1 h | Tumor uptake (% ID/g) 2 h | Tumor uptake (% ID/g) 4 h | Tumor: Blood 1 h | Tumor: Blood 2 h | Tumor: Blood 4 h |
|---|---|---|---|---|---|---|---|
| [18F]CTT1059 | 0.9 irreversible | 1.6 | 1.8 | | 23:1 | 99:1 | |

* Tumor uptake and biodistribution data obtained using LNCaP tumor xenografts. Data for [18F]CTT1056, [18F]CTT1057 and [18F]CTT1059 obtained using CWR22RV1 tumor xenografts.

Example 10

In Vitro Cell Uptake and Internalization of CTT1059

Cell uptake and internalization was measured for CTT1059 according to procedures of *PSMA-targeted SPECT agents: Mode of Binding effect on in vitro Performance*. Nedrow-Byers, J. R.; Moore, A. L.; Ganguly, T.; Hopkins, M. R.; Fulton, M. D.; Benny, P. D.; Berkman, C. E. The Prostate. 2012 (in press, PMID: 22911263, doi: 10.1002/pros.22575). Results are in Table 2.

TABLE 2

In Vitro Cell Uptake and Internalization of CTT1059.

| | 1 h | 2 h |
|---|---|---|
| Average % Uptake | | |
| LNCaP | 7.8% | 14.4% |
| 22RV1 | 2.8% | 3.7% |
| Average % Internalization | | |
| LNCaP | 32% | 48% |
| 22RV1 | 56% | 32% |
| Cell Viability | | |
| LNCaP | 95% | 91% |
| 22RV1 | 93% | 90% |

Example 11

In Vitro Uptake and Internalization Study

Compounds [18F]CTT1056, [18F]CTT1057 and [18F]CTT1059 demonstrated specificity for PSMA as uptake was observed in CWR22Rv1 (PSMA+) cells but not in PC3 (PSMA-) cells. As early as 1 h post-incubation, [18F]CTT1059 exhibited statistically significant higher uptake compared to [18F]CTT1056 and [18F]CTT1057 by student t-test with P values of <0.0001, and [18F]CTT1057 uptake was also statistically higher than [18F]CTT1056 with P value of 0.0012. The same trend was observed at 2 h with P values of <0.0001, <0.0001 and 0.0002; respectively. The activity measured in CWR22Rv1 cells or internalization of [18F]CTT1056, [18F]CTT1057 and [18F]CTT1059 at 1 h were 80.7%, 81.4% and 84.9% respectively, and at 2 h were 94.2%, 84.2% and 91.3% respectively (Table 3). [18F]CTT1056, [18F]CTT1057 and [18F]CTT1059 were internalized in a similar rate within 1 h of incubation in CWR22Rv1 with no statistically significant difference. However, at 2 h the internalization rate became more significant between [18F]CTT1056 and [18F]CTT1057 (P<0.0001) as well as between [18F]CTT1057 and [18F]CTT1059 (P=0.0002) but a lesser degree between [18F]CTT1056 and [18F]CTT1059 (P=0.014).

TABLE 3

Cell uptake data in PSMA+ CWR22Rv1 and PSMA- PC3 cell lines and internalization data in PSMA+ CWR22Rv1 cell lines for [18F]CTT1056, [18F]CTT1057 and [18F]CTT1059 at 1 h and 2 h.

| | [18F]CTT1056 | | [18F]CTT1057 | | [18F]CTT1059 | |
|---|---|---|---|---|---|---|
| Uptake | 1 h | 2 h | 1 h | 2 h | 1 h | 2 h |
| CW22RV1 | 0.39 ± 0.06 | 0.70 ± 0.45 | 0.56 ± 0.05 | 2.28 ± 0.12 | 2.28 ± 0.14 | 4.23 ± 0.64 |
| PC3 | 0.18 ± 0.13 | 0.07 ± 0.02 | 0.04 ± 0.01 | 0.08 ± 0.02 | 0.14 ± 0.04 | 0.15 ± 0.01 |
| Internalization | | | | | | |
| Internalized | 80.68 ± 1.76 | 94.15 ± 2.05 | 81.4 ± 2.7 | 84.2 ± 2.3 | 84.87 ± 3.88 | 91.31 ± 0.94 |
| Bound | 19.32 ± 1.76 | 5.85 ± 2.05 | 18.6 ± 2.7 | 15.8 ± 2.3 | 15.13 ± 3.88 | 8.69 ± 0.94 |

Example 12

In Vivo Imaging and Biodistribution

Figure 14:
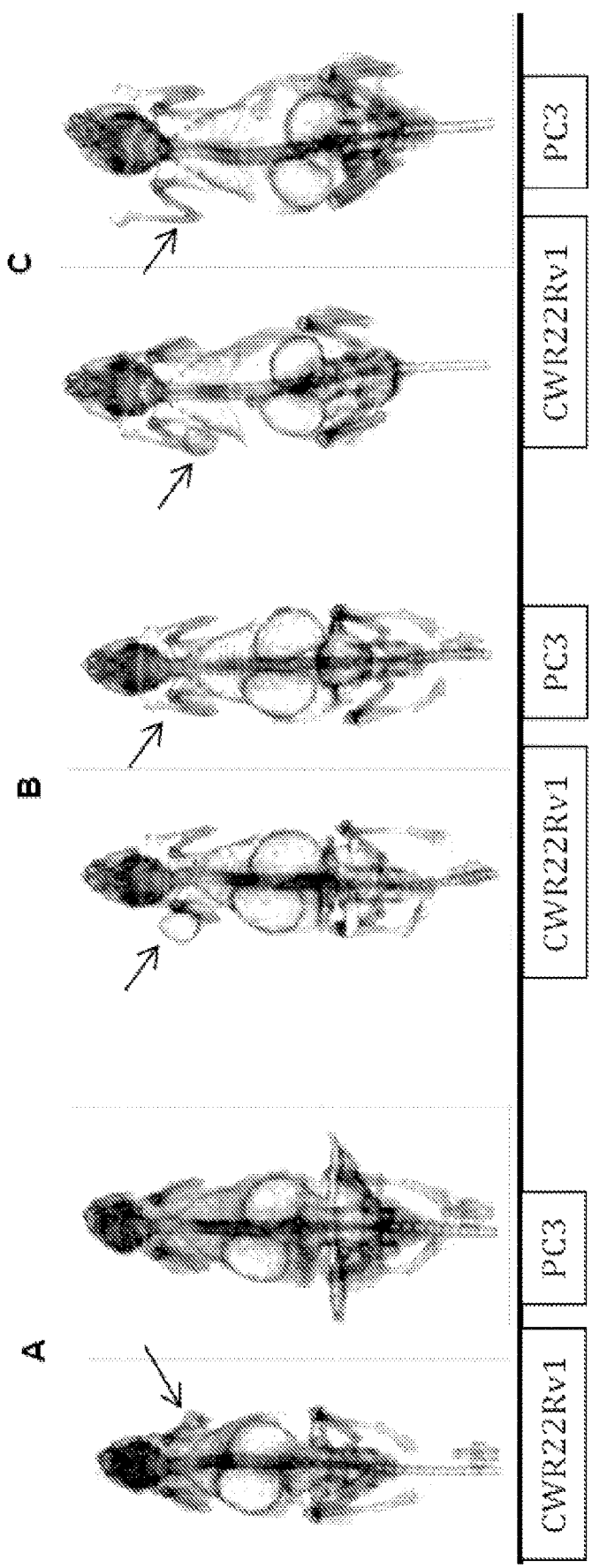
FIG. 14 shows 3D MicroPET/CT images at 2 h post injection of male nude mice bearing CWR22Rv1 and PC3 tumor xenografts respectively A) [18F]CTT1056; B) [18F]CTT1057; and C) [18F]CTT1059. Arrows indicate tumor placement.

Uptake of [18F]CTT1056, [18F]CTT1057 and [18F]CTT1059 at 1 h post-injection in CWR22Rv1 (PSMA+) tumor were 1.54±0.40, 3.16±0.39 and 2.92±0.30% ID/g with a tumor-to-blood ratio of 10, 20 and 24 respectively. At 2 h post-injection, the tumor accumulations were 1.57±0.50, 1.65±0.32 and 1.86±0.14% ID/g with a tumor-to-blood ratio of 26, 64 and 70, respectively. The kidney uptake of [18F]CTT1056, [18F]CTT1057 and [18F]CTT1059 at 1 h post-injection were 8.94±2.93, 24.38±3.72 and 5.87±0.67% ID/g respectively, and at 2 h were 9.97±2.81, 21.54±6.12 and 7.13±1.45% ID/g respectively. For the PC3 (PSMA-) xenograft mouse models, tumor uptake was similar to background/non target organ uptake while the uptake in kidneys for [18F]CTT1056, [18F]CTT1057 and [18F]CTT1059 at 2 h post injection were 5.64±2.41, 18.98±4.75 and 4.44±1.03% ID/g respectively, As shown in the microPET/CT images (FIG. 14), there was tumor uptake of [18F]CTT1056, [18F]CTT1057 and [18F]CTT1059 tracers in the CWR22Rv1 (PSMA+) cells at 2 h post-injection but not in the PC3 (PSMA-) tumors. While there was the expected uptake in the kidneys with all compounds, minimal uptake was seen in all other organs.

TABLE 4

Biodistribution of [18F]CTT1056, [18F]CTT1057 and [18F]CTT1059 as determined by radioactivity assays in PSMA+ CWR22Rv1 tumor-bearing mice (n = 4 in each group). Tissues were harvested at 1 h and 2 h post injection. Uptake values are expressed as % ID/g of tissue

| | [18F]CTT1056 | | | [18F]CTT1057 | | | [18F]CTT1059 | | |
|---|---|---|---|---|---|---|---|---|---|
| | CWR22Rv1 | | PC3 | CWR22Rv1 | | PC3 | CWR22Rv1 | | PC3 |
| Tissue | 1 h | 2 h | 2 h | 1 h | 2 h | 2 h | 1 h | 2 h | 2 h |
| Blood | 0.15 ± 0.07 | 0.07 ± 0.02 | 0.08 ± 0.04 | 0.17 ± 0.05 | 0.04 ± 0.02 | 0.05 ± 0.02 | 0.12 ± 0.03 | 0.03 ± 0.01 | 0.02 ± 0.01 |
| Heart | 0.75 ± 0.32 | 0.50 ± 0.05 | 0.36 ± 0.21 | 0.34 ± 0.11 | 0.17 ± 0.06 | 0.21 ± 0.07 | 0.23 ± 0.05 | 0.06 ± 0.01 | 0.07 ± 0.03 |
| Lung | 0.65 ± 0.34 | 0.43 ± 0.11 | 0.29 ± 0.09 | 0.43 ± 0.09 | 0.21 ± 0.10 | 0.27 ± 0.08 | 0.25 ± 0.07 | 0.11 ± 0.04 | 0.09 ± 0.02 |
| Liver | 0.83 ± 0.23 | 0.5 ± 0.11 | 0.44 ± 0.27 | 0.49 ± 0.11 | 0.29 ± 0.08 | 0.28 ± 0.05 | 0.49 ± 0.07 | 0.25 ± 0.04 | 0.25 ± 0.04 |
| Kidneys | 8.94 ± 2.93 | 9.97 ± 2.81 | 5.46 ± 2.41 | 24.38 ± 3.72 | 21.54 ± 6.12 | 18.98 ± 4.75 | 5.87 ± 0.67 | 7.13 ± 1.45 | 4.44 ± 1.03 |
| Spleen | 1.18 ± 0.08 | 0.87 ± 0.16 | 0.76 ± 0.35 | 1.02 ± 0.04 | 0.84 ± 0.30 | 1.38 ± 1.05 | 0.32 ± 0.12 | 0.19 ± 0.03 | 0.14 ± 0.03 |
| Bone | 0.46 ± 0.04 | 0.5 ± 0.42 | 0.24 ± 0.06 | 0.38 ± 0.09 | 0.23 ± 0.15 | 0.17 ± 0.04 | 0.45 ± 0.12 | 0.21 ± 0.11 | 0.14 ± 0.04 |
| Muscle | 0.29 ± 0.09 | 0.19 ± 0.01 | 0.17 ± 0.04 | 0.12 ± 0.04 | 0.10 ± 0.06 | 0.06 ± 0.01 | 0.15 ± 0.04 | 0.08 ± 0.02 | 0.03 ± 0.01 |
| Tumor | 1.54 ± 0.40 | 1.57 ± 0.45 | 0.40 ± 0.17 | 3.16 ± 0.39 | 1.65 ± 0.32 | 0.38 ± 0.03 | 2.92 ± 0.30 | 1.86 ± 0.14 | 0.27 ± 0.07 |
| Tumor: Blood | 9.88 ± 5.21 | 25.61 ± 14.99 | N/A | 20.01 ± 9.06 | 63.60 ± 18.08 | N/A | 24.21 ± 3.21 | 69.60 ± 15.72 | N/A |

Example 13

In Vitro Uptake and Internalization

The western blot analysis confirmed about 5-fold greater PSMA expression in the LNCaP cells as compared to the CWR22Rv1 cells. GADPH served as a protein loading control. (Section-4 in Supplementary material). This difference in PSMA expression levels between the two cell lines was also mirrored in the cell uptake values of [$^{18}$F]CTT1057 in these cell lines. Increasing uptake in the PSMA(+), LNCaP and CWR22Rv1 cells was observed over 4 h incubation with [$^{18}$F]CTT1057 (Table 5). The percent uptake in LNCaP cells showed about 1.5-fold increase from 1 to 4 h while that in the CWR22Rv1 cells showed a 2-fold increased uptake at 4 h versus 1 h. At 4 h, the LNCaP cells showed 8.74% uptake, five times greater than that in the CWR22Rv1 cells (1.32%) at the same time point. The PC3 cells exhibited little or no uptake of at 1 and 4 h.

The internalization of [$^{18}$F]CTT1057 in LNCaP cells at 1 h was 93% of the activity associated with the cells and 92% at 4 h (Table 5). The CWR22Rv1 cells, which have been used as tumor xenografts for in vivo imaging and biodistribution, showed 81% internalization at 1 h and 91% at 4 h. These results suggest that internalization of the radiotracer is rapid and nearly complete within 1 h.

TABLE 5

Cell uptake and internalization data for [$^{18}$F]CTT1057 in PSMA(+) and PSMA(−) cell lines

| | Uptake | | Internalization | |
|---|---|---|---|---|
| Cell Line | 1 h$^a$ | 4 h$^a$ | 1 h$^a$ | 4 h$^a$ |
| CWR22RV1 | 0.56 ± 0.05 | 1.32 ± 0.52 | 81.4 ± 2.7† | 90.7 ± 2.7† |
| LNCaP | 5.51 ± 0.77 | 8.74 ± 2.67 | 92.9 ± 0.7* | 92.1 ± 0.7* |
| PC3 | 0.04 ± 0.01 | 0.04 ± 0.01 | ND | ND |

$^a$n = 3; mean ± standard deviation

Example 14

Ex Vivo Imaging and Biodistribution

Figure 15:
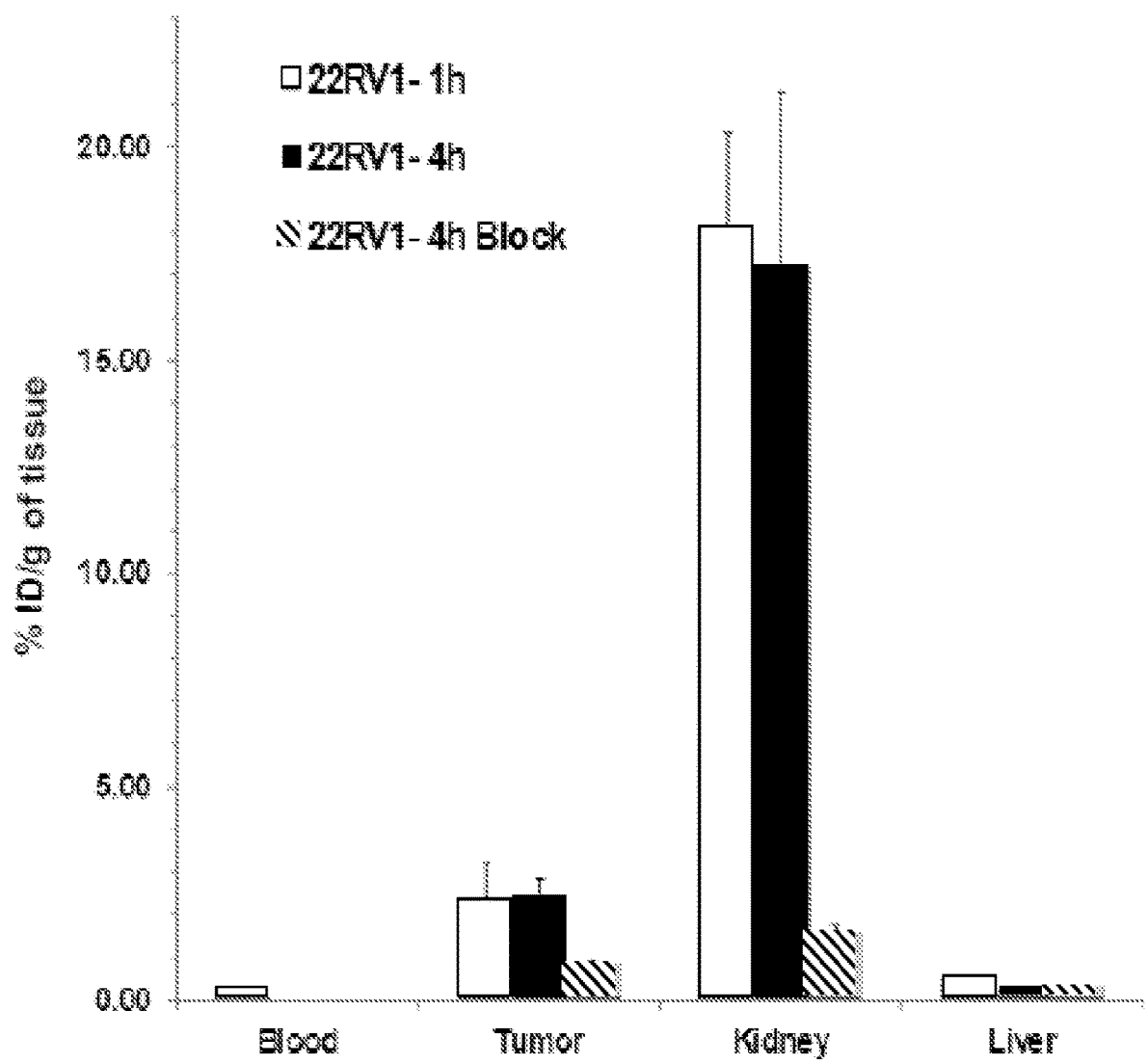
FIG. 15 shows ex vivo biodistribution of [18F]CTT1057.

Ex vivo biodistribution data confirmed the imaging findings (FIG. 15). There was rapid uptake of the tracer in the PSMA positive tumor within the first hour with significant clearance from the blood and other non-PSMA tissues over the 4 h study. At 1 h post-injection, the PSMA(+) tumor accumulation was 2.35±0.91% ID/g with a tumor-to-blood ratio of 22:1. At 4 h post-injection, the tumor accumulation remained at 2.33±0.50% ID/g while 10-fold clearance from the blood provided a tumor-to-blood ratio of 265:1. The kidneys showed expected high uptake and retention of the tracer with 18.12±2.21% ID/g and 17.17±4.13% ID/g at 1 and 4 h, respectively. The limited bone uptake indicated that the tracer was stable to metabolic defluorination. The specificity of [$^{18}$F]CTT1057 for PSMA was demonstrated by the competition study with the deprotected analog of Compound C injected an hour prior to the administration of [$^{18}$F] CTT1057. Upon blocking, the tumor and kidney uptake were significantly decreased by 67% (p=0.0010) and 91% (p=0.0003), respectively.

We claim:

1. A compound of the formula:

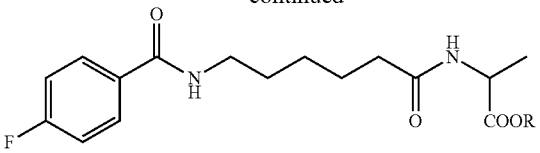

-continued

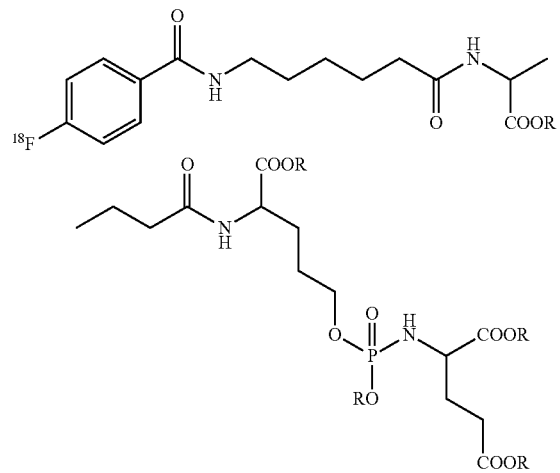

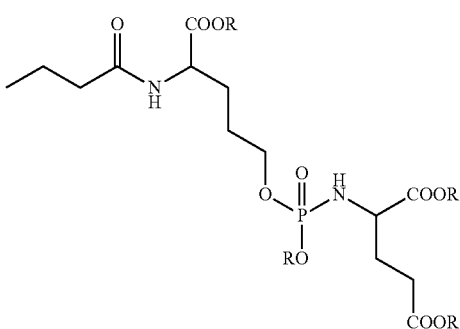

or a pharmaceutically acceptable salt thereof, wherein each R is independently hydrogen or a protecting group.

2. The compound of claim 1, wherein the compound is of the formula:

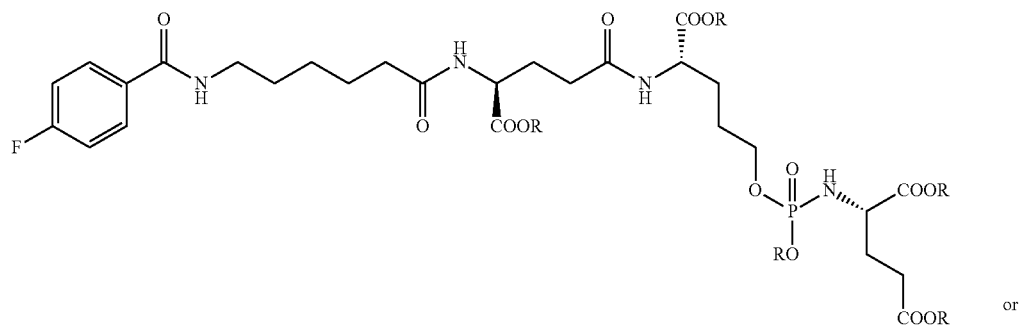

or

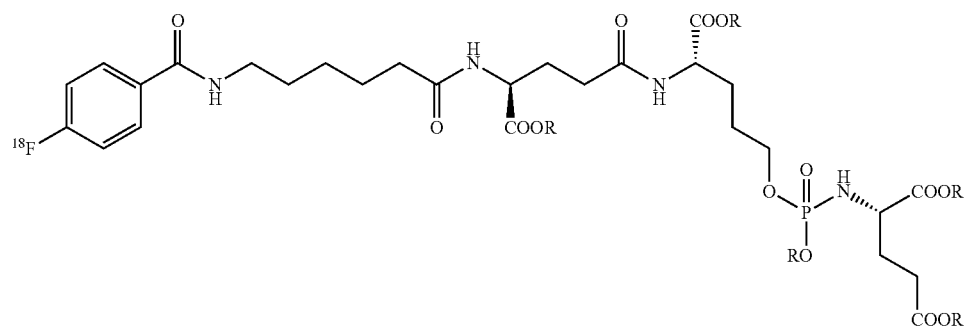

or a pharmaceutically acceptable salt thereof.

3. A composition comprising a compound of claim 1, or a pharmaceutically acceptable salt thereof, together with a pharmaceutically acceptable carrier, excipient, and/or diluent.

4. A compound which is:

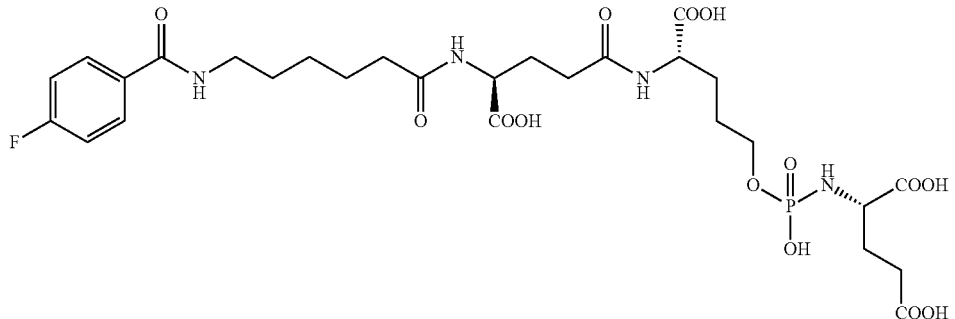 [SMILES: O=C(O)CC[C@H](NP(=O)(O)OCCC[C@H](NC(=O)CC[C@H](NC(=O)CCCCCNC(=O)c1ccc(F)cc1)C(=O)O)C(=O)O)C(=O)O]

or a pharmaceutically acceptable salt thereof.

5. The compound of claim 1, wherein R is benzyl or tert-butyl.

6. A salt of a compound of claim 4, wherein the salt is:

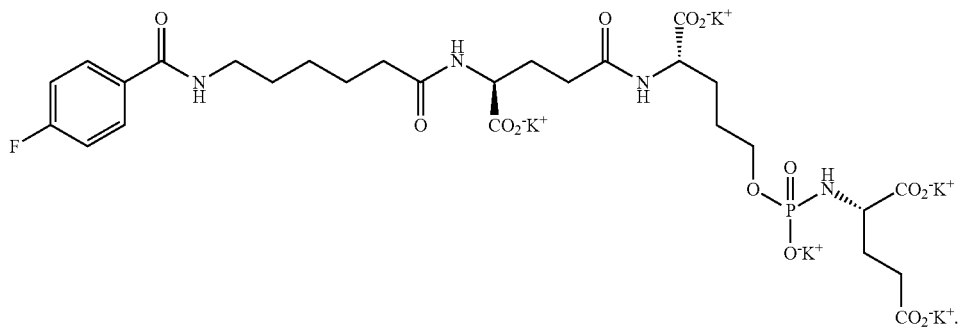

7. A salt of a compound of claim 4, wherein the salt is:

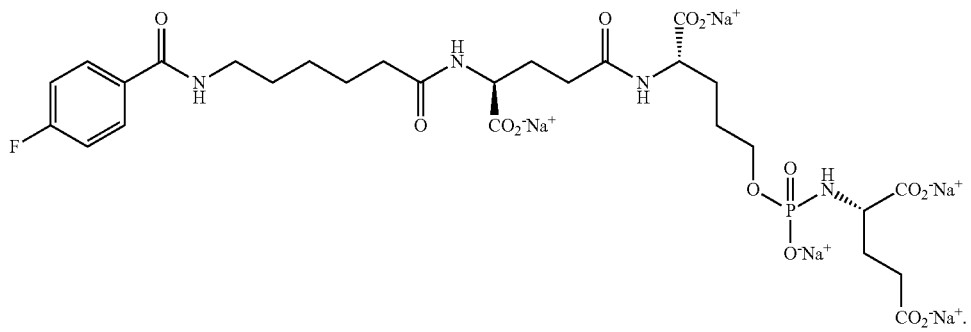

8. A pharmaceutical composition comprising a salt of a compound of claim 4, together with a pharmaceutically acceptable carrier, excipient, and/or diluent, wherein the salt is:

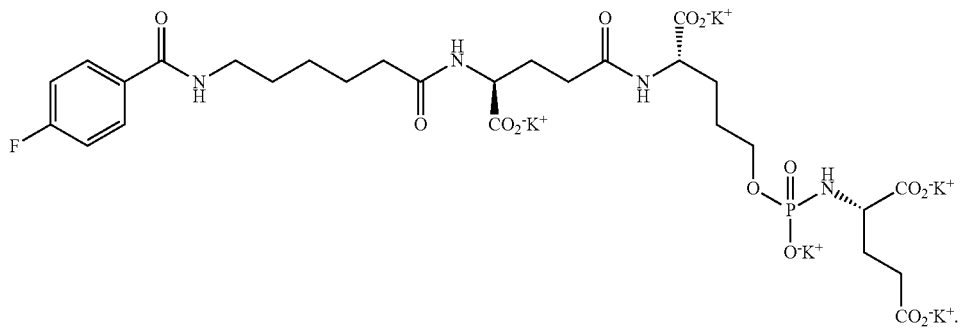

9. A pharmaceutical composition comprising a salt of a compound of claim 4, together with a pharmaceutically acceptable carrier, excipient, and/or diluent wherein the salt is:

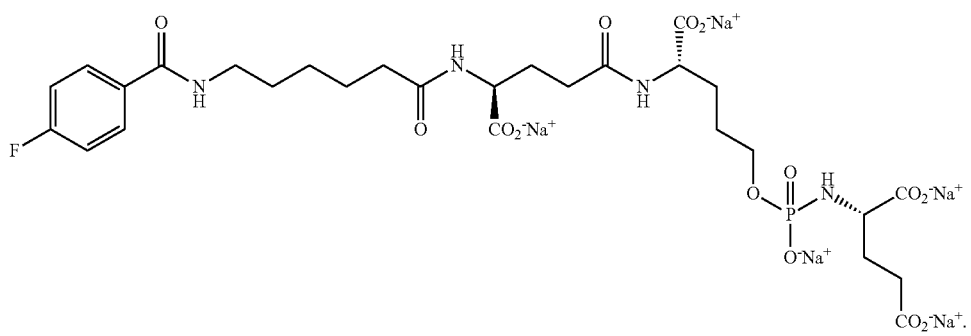

10. A pharmaceutical composition according to claim 8, wherein the pharmaceutically acceptable carrier, excipient, and/or diluent comprises sterile saline.

11. A pharmaceutical composition according to claim 9, wherein the pharmaceutically acceptable carrier, excipient, and/or diluent comprises sterile saline.

12. A compound which is

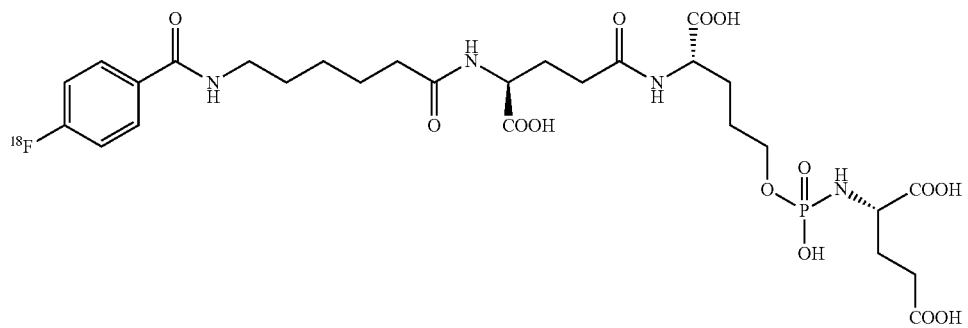 [SMILES: O=C(O)CC[C@H](NP(=O)(O)OCCC[C@H](NC(=O)CC[C@H](NC(=O)CCCCCNC(=O)c1ccc([18F])cc1)C(=O)O)C(=O)O)C(=O)O]

or a pharmaceutically acceptable salt thereof.

13. A salt of a compound of claim 12, wherein the salt is:

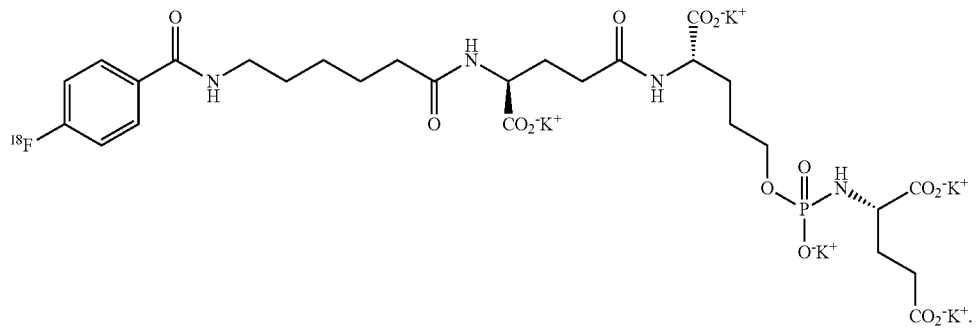

14. A salt of a compound of claim 12 wherein the salt is:

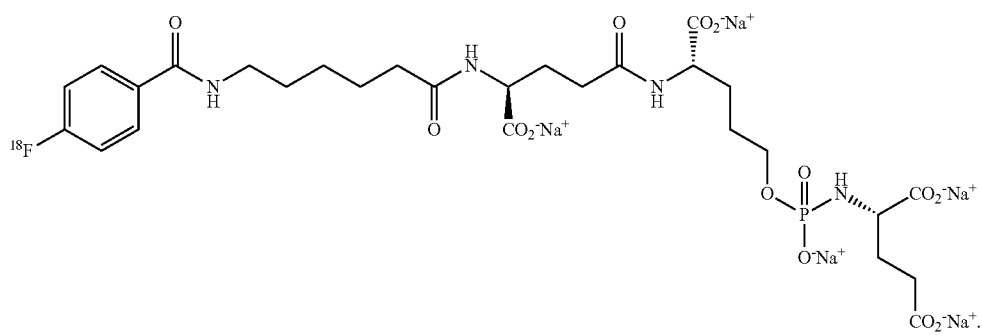

15. A pharmaceutical composition comprising a salt of a compound of claim 12, together with a pharmaceutically acceptable carrier, excipient, and/or diluent, wherein the salt is:

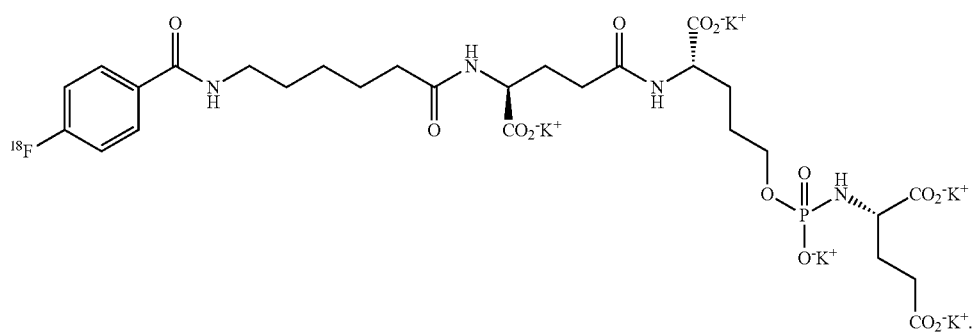

16. A pharmaceutical composition comprising a salt of a compound of claim 12, together with a pharmaceutically acceptable carrier, excipient, and/or diluent wherein the salt is:

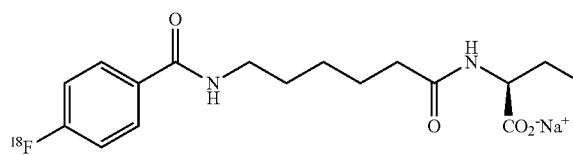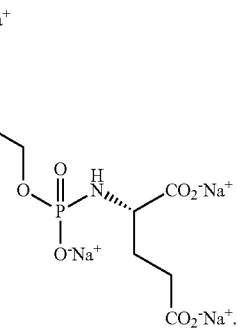
17. A pharmaceutical composition according to claim 15, wherein the pharmaceutically acceptable carrier, excipient, and/or diluent comprises sterile saline.
18. A pharmaceutical composition according to claim 16, wherein the pharmaceutically acceptable carrier, excipient, and/or diluent comprises sterile saline.
* * * * *